(12) United States Patent
Minna et al.

(10) Patent No.: US 7,781,413 B2
(45) Date of Patent: Aug. 24, 2010

(54) SEMA3B INHIBITS TUMOR GROWTH AND INDUCES APOPTOSIS IN CANCER CELLS

(75) Inventors: John Minna, Dallas, TX (US); Yoshio Tomizawa, Takasaki (JP); Yoshitaka Sekido, Nagoya (JP); Michael Lerman, Rockville, MD (US)

(73) Assignee: Board of Regents, The University of Texas System, Austin, TX (US)

( * ) Notice: Subject to any disclaimer, the term of this patent is extended or adjusted under 35 U.S.C. 154(b) by 1402 days.

(21) Appl. No.: 10/285,351

(22) Filed: Oct. 31, 2002

(65) Prior Publication Data

US 2003/0166557 A1    Sep. 4, 2003

Related U.S. Application Data

(60) Provisional application No. 60/335,783, filed on Oct. 31, 2001.

(51) Int. Cl.
*A61K 31/713* (2006.01)
(52) U.S. Cl. .............. 514/44 R; 536/23.5; 530/350; 514/2; 435/320.1; 435/375
(58) Field of Classification Search .......... 435/375, 435/69.1, 320.1; 530/350; 536/23.5; 514/44, 514/2
See application file for complete search history.

(56) References Cited

U.S. PATENT DOCUMENTS

| 6,013,781 A | 1/2000 | Goodman et al. ........ 536/23.1 |
| 6,054,293 A | 4/2000 | Tessier-Lavigne et al. . 435/69.1 |
| 6,171,798 B1 | 1/2001 | Levine et al. .............. 435/6 |

FOREIGN PATENT DOCUMENTS

| WO | WO 99/47671 | 9/1999 |
| WO | WO 01/38491 | 5/2001 |
| WO | WO 01/51518 | 7/2001 |

OTHER PUBLICATIONS

Skolnick et al. (Trends in Biotechnology 2000; 18: 34-39).*
Bowie et al. (Science 257: 1306-1310, 1990).*
Burgess et al. (Journal of Cell Biology 1990; 111: 2129-2138).*
Lazar et al. (Molecular and Cellular Biology, 1988, 8: 1247-1252).*
Takada et al. (Mol. Endocrinol. 2000; 14 (5): 733-740).*
Guo et al. (Proc. Natl. Acad. Sci. USA. Jun. 22, 2004; 101 (25): 9205-9210).*
Roche et al. (Clin. Lung Cancer. Nov. 2001; 3 (2): 145-150).*
Janmaat et al. (Clin. Cancer Res. Jun. 2003; 9: 2316-2326).*
Hsieh et al. (Exp. Cell Res. 1999; 249: 109-115).*
Shafer et al. (Int. J. Oncol. Aug. 2003; 23 (2): 389-400).*
Choi et al. (Exp. Mol. Med. Mar. 2000; 32 (1): 23-28).*
Burbee et al., "Epigenetic inactivation of RASSF1A in lung and breast cancers and malignant phenotype supression," *J. Natl. Cancer Inst.* 93, 691-699, 2001.
Christensen et al., "Transcription of a novel mouse semaphorin gene, M-semaH, correlates with the metastatic ability of mouse tumor cell lines," *Cancer Res.*, 58:1238-1244, 1998.
Dammann et al., "Epigenetic inactivation of a RAS association domain family protein from the lung tumour suppressor locus 3p21.3," *Nat. Genet.*, 25, 315-319, 2000.
GenBank Accession No. NM_004636, Aug. 6, 2003.
GenBank Accession No. NM_009153, Aug. 21, 2003.
GenBank Accession No. Q13214, Sep. 15, 2003.
GenBank Accession No. U28369, Jan. 25, 1999.
GenBank Accession No. U73167, Feb. 4, 1998.
GenBank Accession No. XM_003266, Oct. 16, 2001.
GenBank Accession No. XM_041505, Oct. 16, 2001.
GenBank Accession No. XM_041506, Oct. 16, 2001.
Lerman and Minna, "The 630-kb lung cancer homozygous deletion region on human chromosome 3p21.3: identification and evaluation of the resident candidate tumor suppressor genes," *Cancer Res.*, 60:6116-6133, 2000.
Martin-Satue and Blanco, "Identification of semaphorin E gene expression in metastatic human lung adenocarcinoma cells by mRNA differencial display," *J. Surg. Oncol.*, 72, 18-23, 1999.
Nakamura et al., "Molecular basis of semaphorin-mediated axon guidance," J. Neurobiol., 44:219-29, 2000.
Raper, Curr."Semaphorins and their receptors in vertebrates and invertebrates" *Opin. Neurobiol* , 10: 88-94, 2000.
Sekido et al , "Human semaphorins A(V) and IV reside in the 3p21.3 small cell lung cancer deletion region and demonstrate distinct expression patterns," *Proc Natl. Acad. Sci. USA*, 93:4120-4125, 1996.
Tamagnone and Comoglio, "Signaling by semaphorin receptors: cell guidance and beyond," *Trends Cel Biol.*, 10: 377-83, 2000.
Todd et al., "An 80 Kb P1 clone from chromosome 3p21.3 suppresses tumor growth in vivo," *Oncogen*, 13, 2387-96, 1996.
Tomizawa et al., "Inhibition of lung cancer cell growth and induction of apoptosis after reexpression of 3p21.3 candidate tumor suppressor gene *SEMA3B*," *Proc. Natl. Acad. Sci. USA*, 98:12954, 2001.
Tse, "Human *Semaphorin 3B (SEMA3B)* located at chromosome 3p21.3 suppresses tumor formation in an adenocarcinoma cell line," *Cancer Res.*, 62:542, 2002.
Wei et al., "Construction of a 600-kilobase cosmid clone contig and generation of a transcriptional map surrounding the lung cancer tumor suppressor gene (TSG) locus on human chromosome 3p21.3: progress toward the isolation of a lung cancer TSG," *Cancer Res.*, 56(7):1487-1492, 1996.
Yamada et al., "Identification of semaphorin E as a non-MDR drug resistance gene of human cancers," *Proc. Natl. Acad. Sci. USA*, 94:14713-14718, 1997.

* cited by examiner

*Primary Examiner*—Stephen L Rawlings
(74) *Attorney, Agent, or Firm*—Fulbright & Jaworski, LLP

(57) ABSTRACT

The present invention identifies the semaphorin polypeptide SEMA3B as a tumor suppressor. This molecule can inhibit tumor growth and induce apoptosis of tumor cells when produced internally in a cancer cell via gene transfer, or when applied extracellularly. These observations permit new methods for treatment and diagnosis of cancer.

11 Claims, 14 Drawing Sheets

SEMA3B INHIBITS TUMOR GROWTH AND INDUCES APOPTOSIS IN CANCER CELLS

The present application claims benefit of priority to U.S. Provisional Application Ser. No. 60/335,783, filed Oct. 31, 2001, the entire contents of which are hereby incorporated by reference.

The government owns rights in the present invention pursuant to grant numbers CA71618 and CA70907 from the National Institutes of Health.

BACKGROUND OF THE INVENTION

1. Field of the Invention

The present invention relates generally to the fields of molecular biology, genetics and oncology. More particularly, it concerns semaphorin 3B and its use in cancer therapy and diagnosis.

2. Description of Related Art

The semaphorin family is comprised of secreted and membrane associated proteins that contribute to axonal path finding during neural development by repulsing axons, inhibiting growth cone extension and causing collapse of growth cones (Nakamura et al., 2000; Raper, 2000; Tamagnone and Comoglio, 2000). The SEMA3 family members encode secreted proteins that signal through binding to neuropilin receptors (NP) interacting with plexins (Nakamura et al., 2000; Raper, 2000; Tamagnone and Comoglio, 2000). Several semaphorins are expressed in adult non-neuronal tissues suggesting other functions. For example, SEMA3A inhibited the motility of aortic endothelial cells expressing NP1, disrupted the formation of lamellipodia, induced depolymerization of F-actin (Miao et al., 1999), and inhibited branching morphogenesis in the fetal mouse lung (Ito et al., 2000). However, the roles of SEMA3B and SEMA3F in non-neuronal cells and human cancer are unknown.

Loss of heterozygosity of chromosome 3p sequences is a critical event in the pathogenesis of lung and other cancers and directed a tumor suppressor gene (TSG) search to this region. Multiple distinct 3p regions are involved in human lung cancer pathogenesis including one at 3p21.3, where the inventors identified 19 candidate TSGs were identified. This defined 3p21.3 region undergoes allele loss in ~80% of primary lung cancers and ~40% of preneoplastic or normal epithelial samples of smoking damaged lung, marking it as one of the first sites involved (Wistuba et al., 2000). Two of the 19 genes are semaphorin family members (SEMA3B and SEMA3F) lying ~70 kb apart (Sekido et al., 1996). In assessing the TSG candidacy of SEMA3B and SEMA3F, only a few mutations were found, but loss of expression of SEMA3B mRNA was common, occurring in ~80% of lung cancers.

On the other hand, the inventors and others have found no SEMA3F mutations, and loss of SEMA3F expression in 18%, of these same lung cancers (Sekido et al., 1996; Xiang et al., 1996). However, recent immunohistochemical studies of lung cancers, found reduction of SEMA3F expression in higher stages of lung cancer, and a change in SEMA3F localization from the membrane to the cytoplasm compared to normal lung epithelium (Brambilla et al., 2000). In addition, functional studies using a P1 clone containing SEMA3F (and potentially SEMA3B) showed tumor suppressive effect for mouse A9 fibrosarcoma cells (Todd et al., 1996). Recent studies have implicated tumor acquired promoter hypermethylation as a mechanism of inactivation of mRNA expression of TSGs in the pathogenesis of several human cancers (Baylin et al., 1998). In fact, the inventors and others have found that one isoform at the RASSF1 locus, RASSF1A, located ~60 kb centromeric of SEMA3B, underwent tumor acquired promoter methylation, leading to inactivated expression in lung and breast tumors (Dammann et al., 2000; Burbee et al., 2001).

Thus, although the 3p region has been implicated in cancer development and progression, it is not completely clear which genes in this region are involved. Thus, further information on these issues is needed.

SUMMARY OF THE INVENTION

Thus, in accordance with the present invention, there is provided a method for inhibiting the proliferation of a cancer cell comprising contacting the cell with a semaphorin3B (SEMA3B) polypeptide. The cancer cell may be killed, in particular, through apoptotic cell death. The cancer cell may be a breast cancer cell, a lung cancer cell, a prostate cancer cell, a ovarian cancer cell, a brain cancer cell, a liver cancer cell, a prostate cancer cell, a cervical cancer cell, a colon cancer cell, a renal cancer cell, a skin cancer cell, a head & neck cancer cell, a bone cancer cell, an esophageal cancer cell, a bladder cancer cell, a uterine cancer cell, a lymphatic cancer cell, a stomach cancer cell, a pancreatic cancer cell or a testicular cancer cell. The cancer cell may express a mutant SEMA3B polypeptide, or may fail to express wild-type SEMA3B. The method may further comprise treating the cell with one or more additional anti-proliferative treatments.

The polypeptide may be obtained from media of cultured cells and applied to the surface of the cell. The cultured cells may comprise an expression construct comprising a nucleic acid segment encoding SEMA3B under the control of promoter heterologous to the nucleic acid segment encoding SEMA3B. The polypeptide may be produced from an expression construct comprising a nucleic acid segment encoding SEMA3B under the control of promoter heterologous to the nucleic acid segment encoding SEMA3B, wherein the expression construct has been introduced into the cancer cell. The expression construct may be a viral expression construct, such as adenovirus, retrovirus, adeno-associated virus, herpesvirus, vaccinia virus and polyoma virus. The expression construct may be a non-viral expression construct, for example, a non-viral expression construct encapsulated in a liposome. The promoter may be constitutive, inducible or tissue preferential. The expression construct may further comprise an origin of replication, a polyadenylation signal or a selectable marker gene.

In another embodiment, there is provided conditioned media prepared according to the process comprising (a) obtaining a cell that secretes semaphorin3B (SEMA3B) polypeptide, (b) culturing the cell in a suitable container holding media; and (c) obtaining conditioned media from the container. The cell may comprise an expression construct comprising a nucleic acid segment encoding SEMA3B under the control of promoter heterologous to the nucleic acid segment encoding SEMA3B. The promoter may be a constitutive or inducible promoter. The culturing may be performed for about 12 to about 96 hr. The media may have low serum content or be serum free.

In yet another embodiment, there is provided a method of treating a subject with cancer comprising (a) providing a composition comprising a semaphorin3B (SEMA3B) polypeptide, and (b) administering the composition to the subject. The composition may be delivered systemically, regionally to a discrete tumor mass, locally to a discrete tumor mass, or directly to a discrete tumor mass, e.g., by direct intratumoral injection. The discrete tumor mass may be removed surgically, and the composition may then be delivered to the resected tumor bed. Oral delivery and administration by inhalation also are contemplated. The composition may be delivered in a single dose, in multiple doses, or continuously infused over a period of time exceeding one hour. The subject may be a human subject.

One or more cancer cells may be killed, for example, by undergoing apoptotic cell death. The cancer may be breast cancer, lung cancer, prostate cancer, ovarian cancer, brain cancer, liver cancer, prostate cancer, cervical cancer, colon cancer, renal cancer, skin cancer, head & neck cancer, bone cancer, esophageal cancer, bladder cancer, uterine cancer, lymphatic cancer, stomach cancer, pancreatic cancer or testicular cancer. The cancer may express a mutant SEMA3B polypeptide, or fail to express wild-type SEMA3B. The polypeptide may substantially purified away from other proteinaceous materials, or purified to homogeneity.

The method may further comprise administering to the patient a second cancer therapy, such as surgery, chemotherapy, radiotherapy, gene therapy, immune therapy or hormonal therapy. The second cancer therapy may be provided before composition, after composition, or at the same time as composition. The second cancer therapy may be provided more than once.

In still yet another embodiment, there is provided a method of treating a subject with cancer comprising (a) providing a composition comprising an expression construct comprising a nucleic acid segment encoding SEMA3B under the control of promoter active in cancer cells of the subject, and (b) administering the composition to the subject. The composition may be delivered systemically, regionally to a discrete tumor mass, locally to a discrete tumor mass, or directly to a discrete tumor mass, e.g., by direct intratumoral injection. The discrete tumor mass may be removed surgically, and the composition may then be delivered to the resected tumor bed. The composition may be delivered in a single dose, in multiple doses, or continuously infused over a period of time exceeding one hour. The subject may be a human subject.

The expression construct may be a viral expression construct, such as adenovirus, retrovirus, adeno-associated virus, herpesvirus, vaccinia virus and polyoma virus. The expression construct may be a non-viral expression construct, for example, a non-viral expression construct encapsulated in a liposome. The promoter may be constitutive, inducible or tissue preferential. The expression construct may further comprise an origin of replication, a polyadenylation signal or a selectable marker gene.

One or more cancer cells may be killed, for example, by undergoing apoptotic cell death. The cancer may be breast cancer, lung cancer, prostate cancer, ovarian cancer, brain cancer, liver cancer, prostate cancer, cervical cancer, colon cancer, renal cancer, skin cancer, head & neck cancer, bone cancer, esophageal cancer, bladder cancer, uterine cancer, lymphatic cancer, stomach cancer, pancreatic cancer or testicular cancer. The cancer may express a mutant SEMA3B polypeptide, or fail to express wild-type SEMA3B. The polypeptide may substantially purified away from other proteinaceous materials, or purified to homogeneity.

The method may further comprise administering to the patient a second cancer therapy, such as surgery, chemotherapy, radiotherapy, gene therapy, immune therapy or hormonal therapy. The second cancer therapy may be provided before composition, after composition, or at the same time as composition. The second cancer therapy may be provided more than once.

In a further embodiment, there is provided a method for predicting or diagnosing cancer comprising (a) obtaining a tissue or fluid sample from a subject, and (b) determining whether a SEMA3B polypeptide or nucleic acid is mutant or wild-type, wherein the identification of a SEMA3B mutant in the sample indicates that subject either has, or is at risk of developing, cancer. Determining may comprise an immunoassay targeting the polypeptide, or hybridization of a probe to a nucleic acid, e.g., by sequencing. The cancer may be breast cancer, lung cancer, prostate cancer, ovarian cancer, brain cancer, liver cancer, prostate cancer, cervical cancer, colon cancer, renal cancer, skin cancer, head & neck cancer, bone cancer, esophageal cancer, bladder cancer, uterine cancer, lymphatic cancer, stomach cancer, pancreatic cancer or testicular cancer. The fluid sample may be blood, sputum, bronchial washings, biopsy aspirate or ductal lavage.

In still a further embodiment, there is provided a method for predicting or diagnosing cancer comprising (a) obtaining a sample from a subject suspected of containing a semaphorin3B (SEMA3B) polypeptide, and (b) determining the amount of SEMA3B in the sample, wherein a decrease in the amount SEMA3B polypeptide in the sample, as compared to a similar sample from a non-cancerous subject, indicates that subject either has, or is at risk of developing, cancer. The method may comprise a quantitative immunoassay, such as a Western blot or ELISA. The method may also comprise quantitative RT-PCR or Northern blot. The cancer may be breast cancer, lung cancer, prostate cancer, ovarian cancer, brain cancer, liver cancer, prostate cancer, cervical cancer, colon cancer, renal cancer, skin cancer, head & neck cancer, bone cancer, esophageal cancer, bladder cancer, uterine cancer, lymphatic cancer, stomach cancer, pancreatic cancer or testicular cancer. The sample may be a tissue sample or a fluid sample, such as blood, sputum, bronchial washings, biopsy aspirate or ductal lavage.

In still yet a further embodiment, there is provided a method for predicting or diagnosing cancer comprising (a) obtaining a sample from a subject that contains genomic DNA, and (b) determining loss of heterozygosity for the SEMA3B allele in genomic DNA from the sample, wherein a loss of heterozygosity in DNA from the sample indicates that subject either has, or is at risk of developing, cancer. The cancer may be breast cancer, lung cancer, prostate cancer, ovarian cancer, brain cancer, liver cancer, prostate cancer, cervical cancer, colon cancer, renal cancer, skin cancer, head & neck cancer, bone cancer, esophageal cancer, bladder cancer, uterine cancer, lymphatic cancer, stomach cancer, pancreatic cancer or testicular cancer. The sample may be a tissue sample or a fluid sample, e.g., blood, sputum, bronchial washings, biopsy aspirate or ductal lavage. The loss of heterozygosity may be determined by PCR.

In an additional embodiment, there is provided a method for predicting or diagnosing cancer comprising (a) obtaining a sample from a subject that contains a SEMA3B nucleic acid, and (b) determining the presence or absence of a loss of function mutation in the nucleic acid from the sample, wherein the presence of a loss of function mutation in the nucleic acid indicates that subject either has, or is at risk of developing, cancer. The cancer may be breast cancer, lung cancer, prostate cancer, ovarian cancer, brain cancer, liver cancer, prostate cancer, cervical cancer, colon cancer, renal cancer, skin cancer, head & neck cancer, bone cancer, esophageal cancer, bladder cancer, uterine cancer, lymphatic cancer, stomach cancer, pancreatic cancer or testicular cancer. The may be RNA or DNA, e.g., germ line DNA. The RNA may be converted to DNA. The sample may be a tissue sample or a fluid sample, e.g., blood, sputum, bronchial washings, biopsy aspirate or ductal lavage.

In yet an additional embodiment, there is provided a method for predicting or diagnosing cancer comprising (a)

obtaining a sample from a subject that contains genomic DNA sequences encoding a SEMA3B promoter region, and (b) determining the presence or absence of CpG island methylation in the SEMA3B promoter region, wherein the presence of hypermethylation in the promoter indicates that subject either has, or is at risk of developing, cancer. The hypermethylation may be determined by sequencing of sodium bisulfite modified DNA. Hypermethylation may comprise complete methylation of more than one CpG island, including complete methylation of 2, 3, 4, 5, 6, 7 or 8 CpG islands. Hypermethylation also may comprise partial methylation of more than one CpG island, including partial methylation of 2, 3, 4, 5, 6, 7 or 8 CpG islands. The hypermethylation may comprise both partial methylation and complete methylation of CpG islands. The sample may be a tissue sample or a fluid sample, for example, blood, sputum, bronchial washings, biopsy aspirate or ductal lavage. The method may also be applied to a subject that has previously been diagnosed with cancer and received cancer therapy, and the presence of hypermethylation indicates that the subject is undergoing relapse or cancer progression.

In still an additional embodiment, there is provided a method for assessing a cancer therapy cancer comprising (a) obtaining a sample from a subject that contains genomic DNA sequences encoding a SEMA3B promoter region; and (b) determining the presence or absence of CpG island methylation in said SEMA3B promoter region, wherein the loss of hypermethylation in said promoter indicates that the cancer therapy has been effective.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 1A: Sequence of the region that was subjected to analysis. Positions of CpG sites are numbered 1-8. Primers used for amplification are indicated by arrows. Primers cited in Materials & Methods are designed to amplify the opposite strand as compared to the sequence shown in FIG. 1 (SEQ ID NO:6). FIG. 1B: Methylation status of each CpG sites (labeled 1-8 in FIG. 1A) determined by sequencing sodium bisulfite treated genomic DNA from tumor cells. White and black squares represent unmethylated and methylated CpGs, respectively. Partially filled squares represent partially methylated CpG.

FIG. 3A: Western blot analysis of NSCLC H1299 cells transfected with various SEMA3B plasmids. FIG. 3B: Western blot of H1299 cells transfected with SEMA3F. FIG. 3C and FIG. 3D: H1299 colony formation after transfection and G418 selection. In FIGS. 3A and 3B plasmids were transfected into $5 \times 10^5$ H1299 cells by lipofection, cells harvested 48 hr later, 50 µg total lysate Western blotted with anti-SEMA3B (FIG. 3A) and anti-SEMA3F antisera (FIG. 3B). FIG. 3C: colony formation after transfection and selection with G418 stained with methylene blue. Vector Control=pcDNA3; AS=pcDNA3 with wild-type SEMA3B in antisense direction, SEMA3BWT=SEMA3B wild type; SEMA3F=SEMA3F wild-type; R348C, D397H, T415I=SEMA3B constructs with indicated mutations introduced; p53=pcDNA3 with wild-type p53. FIG. 3D: Quantitation of the number of G418 selected H1299 colonies. The vector control was set at 100%. Data represent the mean±SD of five independent studies each done in triplicate plates; D561N data not shown.

FIG. 4A: $1 \times 10^4$ H1299 cells were seeded in 35 mm dishes. After 24 hr, empty vector control or pSEMA3B expression plasmids were transfected (~20-30% efficiency) and the number of cells counted 48 hr later. Data represent the mean+SD of five independent studies. FIG. 4B: The terminal deoxynucleotidyl transferase-mediated dUTP nick end labeling (TUNEL) assay 24 hr after H1299 cells were transfected with a SEMA3B plasmid. The TUNEL positive cells (~20%) are indicated by arrows. Vector control transfected cells (TUNEL positive <2%) are not shown. FIG. 4C: Fluorescence-activated cells sorting profiles of H1299 transfected with empty vector (control) or the SEMA3B expression plasmid. Cells were harvested 48 hr later, stained with propidium iodide, and analyzed using the flow cytometer. Horizontal and vertical axes represent DNA content and cell number respectively. The % of sub-G1 cells undergoing apoptosis is indicated. FIG. 4D: Caspase-3 activity in H1299 cells 20 hr after transfection with SEMA3B or p53 (positive control) expression plasmids. Data represent the mean+SD of three independent studies. p53 and SEMA3B transfected cells had significantly higher caspase 3 activity than vector controls while DEVD-fmk treated p53 and SEMA3B cells did not.

FIG. 5A: Each indicated plasmid was transfected into $5 \times 10^5$ COS-7 cells by lipofection. After 48 hr incubation, the conditioned media were collected and applied to $5 \times 10^3$ H1299 cells seeded in each well of 6-well plates. After 4 days, the cells in each indicated conditioned medium were photographed (FIG. 5A) (original magnification is ×40); or counted (FIG. 5B). The number of H1299 cells in the cultures treated with conditioned medium from empty vector controls were set at 100%. Data represent the mean+SD of three independent studies. SEMA3B transfected COS-7 cell conditioned medium gave significantly fewer numbers of H1299 cells compared to treatment with condition medium following transfection with the SEMA3B mutants (R348C, D397H, T415I, D561N) or the SEMA3B antisense (AS) constructs. FIG. 5C: Growth curve of H1299 NSCLC cells in the conditioned medium of COS-7 cells transfected with control or SEMA3B expression plasmids. At each indicated time point, cell viability was determined and represented as the degree of absorbance 540 nm using the MTT assay. The mean±SD absorbance (triplicate wells) for each time point is plotted as a function of the number of days after seeding.

DESCRIPTION OF ILLUSTRATIVE EMBODIMENTS

Figure 1A:
FIGS. 1A-1B.—Methylation analysis of SEMA3B.

A large number of polypeptides have been implicated in the development of cancer, or in its inhibition. Genes that promote cancer formation are often referred to as "oncogenes." Inhibitors of cancer include polypeptides described as "tumor suppressors." Genes encoding tumors suppressors (TSGs) are often mutated in cancerous cells, thereby reducing their cancer inhibitory effects. Other deleterious mutations result in decreased TSG expression.

Mutations in chromosome 3p sequences are common in lung and other cancers, leading researches to investigate the possibility that one or more TSGs reside in this region. The present invention demonstrates, for the first time, that SEMA3B is a TSG. The inventors show that one mechanism for loss of SEMA3B function is methylation of CpG motifs in the putative SEMA3B promoter region. In addition, following transfection and expression, wild-type SEMA3B induces growth inhibition of lung cancer cells. As further proof of SEMA3B's TSG status, lung cancer-associated SEMA3B missense mutations (located at codons 348, 397, 415 and 561) cause a loss of this tumor growth suppressive function. These sites are located in the semaphorin domain, which is necessary for semaphorin dimerization and biological activity (Nakamura et al., 2000; Raper, 2000; Tamagnone and Comoglio, 2000). Interestingly, the addition of a C-terminal FLAG tag also causes loss of this function, even though this adds a mere five amino acids to the wild-type SEMA3B sequence.

The mechanism of SEMA3B-induced apoptosis is unknown. Another secreted semaphorin, SEMA3A, induces apoptosis in sympathetic (Shirvan et al., 1999) and sensory neurons (Gagliardini and Fankhauser, 1999). Semaphorins contain a short sequence of homology to tarantula hanatoxin, and the sequence is required to induce of growth cone collapse in neuronal cells (Behar et al., 1999). However, growth suppression was not observed after transfection of mutant SEMA3B constructs retaining the hanatoxin sequence. The growth of several lung cancer cell lines but not normal bronchial epithelial cultures was suppressed by conditioned medium harvested from COS-7 cells transfected with wild-type SEMA3B. In contrast, conditioned medium from mutant SEMA3B-transfected COS-7 cells did not suppress growth. Further, anti-NP1 antibodies did not block SEMA3B-transfected COS-7 cell conditioned medium growth suppression. In addition, NSCLC NCI-H23 was resistant to over expression of SEMA3B but sensitive to SEMA3B transfected COS-7 conditioned medium. These findings would appear to support an indirect mechanism for SEMA3B function.

Bachelder et al. (2001) found vascular endothelial growth factor (VEGF) was an autocrine survival factor for NP expressing breast cancer cells, while SEMA3A competed with VEGF165 for binding to NP1 receptors and inhibited vascular endothelial cell motility suggesting a role in inhibiting angiogenesis (Miao et al., 1999). In fact, the different effects of SEMA3B on normal bronchial epithelial cells versus cancer cells may occur because normal cells are not dependent on survival factors such as VEGF, while lung cancer cells may require these factor(s). NP1 was expressed in all the lung cancers, and overexpression of NP1 itself may contribute to oncogenesis by enhancing angiogenesis, while a soluble NP1 receptor bound VEGF and inhibited tumorigenesis (Miao et al., 2000; Gagnon et al., 2000). Thus, one model to consider is that SEMA3B acts to antagonize VEGF acting through the NP1 receptors. Substantial data indicates that the complex of NP1 and Plexin 1 is the physiologic signal transducer for SEMA3A (Nakamura et al., 2000; Raper, 2000; Tamagnone and Comoglio, 2000). Therefore, plexins also need to be studied to understand the growth suppression and apoptosis induced in lung cancer by SEMA3B.

Several other reports have noted correlations between semaphorins, growth control, or cancer. In *C. elegans*, SEMA2A as a null mutant led to errant epidermal cell migrations and affected epidermal enclosure of the embryo (Roy et al., 200). In contrast to the tumor suppressing function of SEMA3B, SEMA3C and SEMA3E overexpressed in metastatic human and mouse tumors and SEMA3C led to cancer therapy drug resistance (Martin-Satue and Blanco, 1999; Yamada et al., 1997; Christensen et al., 1998). Thus, abnormalities of some semaphorin family genes may play a cooperative role in carcinogenesis, analogous to the role these genes play in the developing nervous system.

Thus, the present invention seeks to exploit the inventors' discovery by applying various forms of SEMA3B in therapeutic contexts. Both SEMA3B polypeptides and SEMA3B expression constructs may be utilized to inhibit cancer growth. In addition, alterations in SEMA3B function may prove useful in the diagnosis of cancer or its prediction. Finally, screening for agents that increase SEMA3B activity or expression may prove useful as cancer therapeutics. These and other embodiments are discussed in detail below.

I. SEMA3B Polypeptides

In certain embodiments, the present invention concerns compositions comprising a SEMA3B polypeptide as described herein. Other names that have been used to identify SEMA3B include sema5, SemA, semaV, and SEMAA. The full length SEMA3B human sequence is 750 residues in length (GenBank Accession No. U28369) (SEQ ID NO:1). SMART and PFAM programs identify a signal peptide (residues 1-25), a PFAM:SEMA domain (residues 55-497), and one IGc2 domain (residues 587-646). Interestingly, the PFAM:SEMA domain is also present in the extracellular part of the MET and RON oncoproteins belonging to the MET family of receptor tyrosine kinases (RTKs), as discovered by the PFAM program.

The present invention may utilize SEMA3B protein purified from a natural source or from recombinantly produced material. This material may use the 20 common amino acids in naturally synthesized proteins, or one or more modified or unusual amino acid, including but not limited to those shown on Table 1 below.

TABLE 1

Modified and Unusual Amino Acids

| Abbr. | Amino Acid |
|---|---|
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, pipendinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| AIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

In certain embodiments, the SEMA3B protein may be purified. Generally, "purified" will refer to a SEMA3B composition that has been subjected to fractionation to remove various other proteins, polypeptides, or peptides, and which composition substantially retains its tumor suppressing activity. Purification may be substantial, in which the SEMA3B polypeptide is the predominant species, or to homogeneity, which purification level would permit accurate degradative sequencing.

The term "an amino acid sequence essentially as set forth in SEQ ID NO:1" means that the sequence substantially corresponds to a portion of SEQ ID NO: 1 and has relatively few amino acids that are not identical to, or biologically functional equivalent of, the amino acids of SEQ ID NO: 1. The term "biologically functional equivalent" is well understood in the art and/or is further defined in detail herein. Accordingly, sequences that have between about 91% and/or about 99% of amino acids that are identical or functionally equivalent to the amino acids of SEQ ID NO: 1 will be sequences that are "essentially as set forth in SEQ ID NO: 1," provided the biological activity of the protein, in this case tumor suppression, is maintained.

II. SEMA3B Polynucleotides

The SEMA3B gene is composed of 17 exons spread over 8-10 kb of the human genome on chromosome 3. These exons code for a 3.4-kb mRNA expressed in several normal tissues including lung and testis. The messenger derived cDNA at GenBank Accession No. U28369 (SEQ ID NO:2), and the genomic sequence can be found at GenBank Accession No. U73167 (SEQ ID NO:3).

A. Polynucleotides

Important aspects of the present invention concern isolated nucleic acid segments —RNA or DNA—encoding SEMA3B. Such molecules permit the creation of as recombinant host cell that expresses SEMA3B polypeptides. As used herein, the term "nucleic acid" refers to a polymer of DNA, RNA or a derivative or mimic thereof, of two or more bases in length.

The term "oligonucleotide" refers to a polymer of DNA, RNA or a derivative or mimic thereof, of between about 3 and about 100 bases in length. The term "polynucleotide" refers to a polymer of DNA, RNA or a derivative or mimic thereof, of greater than about 100 bases in length. Thus, it will be understood that the term "nucleic acid" encompass the terms "oligonucleotide" and "polynucleotide." These definitions generally refer to at least one single-stranded molecule, but in specific embodiments will also encompass at least one double-stranded molecule. Within the scope of the invention, it is contemplated that the terms "oligonucleotide," "polynucleotide" and "nucleic acid" will generally refer to at least one polymer comprising one or more of the naturally occurring monomers found in DNA (A, G, T, C) or RNA (A, G, U, C).

The present invention concerns DNA segments isolatable from cancerous and non-cancerous cells alike, particularly human cells. In some cases, the segments may be free from total genomic DNA and be capable of expressing a SEMA3B polypeptide that has tumor suppressor activity. As used herein, the term "DNA segment" refers to a DNA molecule that has been isolated free of total genomic DNA. Included within the term "DNA segment" are DNA segments and smaller fragments of such oligonucleotides, as well as larger segments such as recombinant vectors, for example, plasmids, cosmids, phage, viruses, and the like.

The term "functionally equivalent codon" is used herein to refer to codons that encode the same amino acid, such as the six codons for arginine and serine, and also refers to codons that encode biologically equivalent amino acids. The codons are shown in preference of use from left to right, in Table 2. The most preferred codon for alanine is thus "GCC", and the least is "GCG" (see Table 2, below).

TABLE 2

Preferred Human DNA Codons

| Amino Acids | | | Codons |
|---|---|---|---|
| Alanine | Ala | A | GCC GCT GCA GCG |
| Cysteine | Cys | C | TGC TGT |
| Aspartic acid | Asp | D | GAC GAT |
| Glutamic acid | Glu | E | GAG GAA |

TABLE 2-continued

Preferred Human DNA Codons

| Amino Acids | | | Codons |
|---|---|---|---|
| Phenylalanine | Phe | F | TTC TTT |
| Glycine | Gly | G | GGC GGG GGA GGT |
| Histidine | His | H | CAC CAT |
| Isoleucine | Ile | I | ATC ATT ATA |
| Lysine | Lys | K | AAG AAA |
| Leucine | Leu | L | CTG CTC TTG CTT CTA TTA |
| Methionine | Met | M | ATG |
| Asparagine | Asn | N | AAC AAT |
| Proline | Pro | P | CCC CCT CCA CCG |
| Glutamine | Gln | Q | CAG CAA |
| Arginine | Arg | R | CGC AGG CGG AGA CGA CGT |
| Serine | Ser | S | AGC TCC TCT AGT TCA TCG |
| Threonine | Thr | T | ACC ACA ACT ACG |
| Valine | Val | V | GTG GTC GTT GTA |
| Tryptophan | Trp | W | TGG |
| Tyrosine | Tyr | Y | TAC TAT |

Sequences that are essentially the same as those set forth in SEQ ID NOS:2 and 3 may also be defined functionally as sequences that are capable of hybridizing to a nucleic acid segment containing the complement of SEQ ID NOS:2 and 3 under high stringency conditions. Suitable high stringency hybridization conditions will be well known to those of skill in the art, as disclosed herein. For example, hybridization at high temperature and/or low ionic strength is termed high stringency. High stringency is generally performed at 0.02 M to 0.15 M NaCl at a temperature range of 50° C. to 70° C.

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended protocol.

For example, nucleic acid fragments may be prepared that include a contiguous stretch of nucleotides identical to SEQ ID NOS:2 or 3, such as up to about 1,000,000, about 750,000, about 500,000, about 250,000, about 100,000, about 50,000, about 20,000, about 10,000, and about 5,000 base pairs in length. In certain cases, nucleotide segments of a million bases or more, including chromosome sized pieces of DNA, are contemplated as being useful.

The various probes or primers designed around the disclosed SEMA3B nucleotide sequences of the present invention may be of any useful length. By assigning numeric values to a sequence, for example, the first residue is 1, the second residue is 2, etc., an algorithm defining all primers can be proposed:

n to n+y where n is an integer from 1 to the last number of the sequence and/or y is the length of the primer minus one, where n+y does not exceed the last number of the sequence. Thus, for a 10-mer, the probes correspond to bases 1 to 10, 2 to 11, 3 to 12 . . . and/or so on. For a 15-mer, the probes correspond to bases 1 to 15, 2 to 16, 3 to 17 . . . and/or so on. For a 20-mer, the probes correspond to bases 1 to 20, 2 to 21, 3 to 22 . . . and/or so on.

Encompassed by the invention are short DNA segments of from about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 40, about 45, to about 50 bases in length.

In addition to the "standard" DNA and RNA nucleotide bases, modified bases are also contemplated for use in particular applications of the present invention. A table of exemplary, but not limiting, modified bases is provided herein below.

TABLE 3

Modified Bases

| Abbr. | Modified base description |
|---|---|
| ac4c | 4-acetylcytidine |
| chm5u | 5-(carboxyhydroxylmethyl)uridine |
| cm | 2'-O-methylcytidine |
| cmnm5s2u | 5-carboxymethylaminomethyl-2-thioridine |
| cmnm5u | 5-carboxymethylaminomethyluridine |
| d | Dihydrouridine |
| fm | 2'-O-methylpseudouridine |
| gal q | beta, D-galactosylqueosine |
| gm | 2'-O-methylguanosine |
| i | Inosine |
| i6a | N6-isopentenyladenosine |
| m1a | 1-methyladenosine |
| m1f | 1-methylpseudouridine |
| m1g | 1-methylguanosine |
| m1i | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| mam5u | 5-methylaminomethyluridine |
| mam5s2u | 5-methoxyaminomethyl-2-thiouridine |
| man q | beta,D-mannosylqueosine |
| mcm5s2u | 5-methoxycarbonylmethyl-2-thiouridine |
| mcm5u | 5-methoxycarbonylmethyluridine |
| mo5u | 5-methoxyuridine |
| ms2i6a | 2-methylthio-N6-isopentenyladenosine |
| ms2t6a | N-((9-beta-D-ribofuranosyl-2-methylthiopurine-6-yl)carbamoyl)threonine |
| mt6a | N-((9-beta-D-ribofuranosylpurine-6-yl)N-methyl-carbamoyl)threonine |
| mv | uridine-5-oxyacetic acid methylester |
| o5u | uridine-5-oxyacetic acid (v) |
| osyw | wybutoxosine |
| p | pseudouridine |
| q | queosine |
| s2c | 2-thiocytidine |
| s2t | 5-methyl-2-thiouridine |
| s2u | 2-thiouridine |
| s4u | 4-thiouridine |
| t | 5-methyluridine |
| t6a | N-((9-beta-D-ribofuranosylpurine-6-yl)carbamoyl)threonine |
| tm | 2'-O-methyl-5-methyluridine |
| um | 2'-O-methyluridine |
| yw | wybutosine |
| x | 3-(3-amino-3-carboxypropyl)uridine,(acp3)u |

B. Expression Constructs

In order to deliver SEMA3B sequences to cells, one may introduce a nucleic acid segment coding for SEMA3B into an expression vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence or "cassette" coding for at least part of a gene product capable of being transcribed and "regulatory" or "control" sequences, which refer to nucleic acid sequences necessary for the transcription and possibly translation of an operably linked coding sequence in a particular host cell. In addition to control sequences that govern transcription and translation, expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence. Together, an appropriate promoter or promoter/enhancer combination, and a gene of interest, comprise an expression cassette.

A promoter may be one naturally associated with a gene or sequence, as may be obtained by isolating the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Such promoters may be used to drive β-galactosidase or luciferase expression for use as a reporter gene. Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al., (2000), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Various promoters may be utilized in the context of the present invention to regulate the expression of a delivered SEMA3B gene. Of particular interest are tissue-specific promoters or elements, which permit tissue selective or preferential expression of SEMA3B. For example, a promoter that is preferentially active in cancer cells is hTERT.

2. Initiation Signals

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

3. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (Chandler et al., 1997).

4. Polyadenylation Signals

One may include a polyadenylation signal in the expression construct to effect proper polyadenylation of the transcript. The nature of the polyadenylation signal is not believed to be crucial to the successful practice of the invention, and/or any such sequence may be employed. Specific embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

5. Termination Signals

The vectors or constructs of the present invention may comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker. Examples of selectable and screenable markers are well known to one of skill in the art.

8. IRES

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (U.S. Pat. Nos. 5,925,565 and 5,935,819; PCT/US99/05781).

III. Polynucleotide Transfer

There are a number of ways in which SEMA3B expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986).

1. Adenovirus Expression Vectors

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus et al., 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

In one system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

Adenovirus vectors have been used in eukaryotic gene expression (Levrero et al., 1991; Gomez-Foix et al., 1992) and vaccine development (Grunhaus et al., 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

2. Retrovirus Expression Vectors

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

3. Herpesvirus Expression Vectors

Herpes simplex virus (HSV) has generated considerable interest in treating nervous system disorders due to its tropism for neuronal cells, but this vector also can be exploited for other tissues given its wide host range. Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al. (1995).

HSV, designated with subtypes 1 and 2, are enveloped viruses that are among the most common infectious agents encountered by humans, infecting millions of human subjects worldwide. The large, complex, double-stranded DNA genome encodes for dozens of different gene products, some of which derive from spliced transcripts. In addition to virion and envelope structural components, the virus encodes numerous other proteins including a protease, a ribonucleotides reductase, a DNA polymerase, a ssDNA binding protein, a helicase/primase, a DNA dependent ATPase, a dUTPase and others.

HSV genes form several groups whose expression is coordinately regulated and sequentially ordered in a cascade fashion (Honess and Roizman, 1974; Honess and Roizman 1975). The expression of α genes, the first set of genes to be expressed after infection, is enhanced by the virion protein number 16, or α-transinducing factor (Post et al., 1981; Batterson and Roizman, 1983). The expression of β genes requires functional α gene products, most notably ICP4, which is encoded by the α4 gene (DeLuca et al., 1985). γ genes, a heterogeneous group of genes encoding largely virion structural proteins, require the onset of viral DNA synthesis for optimal expression (Holland et al., 1980).

In line with the complexity of the genome, the life cycle of HSV is quite involved. In addition to the lytic cycle, which results in synthesis of virus particles and, eventually, cell death, the virus has the capability to enter a latent state in which the genome is maintained in neural ganglia until some as of yet undefined signal triggers a recurrence of the lytic cycle. A virulent variants of HSV have been developed and are readily available for use in gene therapy contexts (U.S. Pat. No. 5,672,344).

4. Adeno-Associated Virus Expression Vectors

Adeno-associated virus (AAV) has emerged as a potential alternative to the more commonly used retroviral and adenoviral vectors. While studies with retroviral and adenoviral mediated gene transfer raise concerns over potential oncogenic properties of the former, and immunogenic problems associated with the latter, AAV has not been associated with any such pathological indications.

In addition, AAV possesses several unique features that make it more desirable than the other vectors. Unlike retroviruses, AAV can infect non-dividing cells. Wild-type AAV has been characterized by integration, in a site-specific manner, into chromosome 19 of human cells (Kotin and Berns, 1989; Kotin et al., 1990; Kotin et al., 1991; Samulski et al., 1991). AAV also possesses anti-oncogenic properties (Ostrove et al., 1981; Berns and Giraud, 1996). Recombinant AAV genomes are constructed by molecularly cloning DNA sequences of interest between the AAV ITRs, eliminating the entire coding sequences of the wild-type AAV genome. The AAV vectors thus produced lack any of the coding sequences of wild-type AAV, yet retain the property of stable chromosomal integration and expression of the recombinant genes upon transduction both in vitro and in vivo (Berns, 1990; Berns and Bohensky, 1987; Kearns et al., 1996; Ponnazhagan et al., 1997). Until recently, AAV was believed to infect almost all cell types, and even cross species barriers. However, it now has been determined that AAV infection is receptor-mediated (Ponnazhagan et al., 1996; Mizukami et al., 1996).

AAV utilizes a linear, single-stranded DNA of about 4700 bases. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription. The sequence of AAV is provided in U.S. Pat. No. 5,252,479 (entire text of which is specifically incorporated herein by reference).

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

5. Vaccinia Virus Expression Vectors

Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome. The majority of essential genes appear to map within the central region, which is most highly conserved among poxviruses. Estimated open reading frames in vaccinia virus number from 150 to 200. Although both strands are coding, extensive overlap of reading frames is not common.

At least 25 kb can be inserted into the vaccinia virus genome (Smith and Moss, 1983). Prototypical vaccinia vectors contain transgenes inserted into the viral thymidine kinase gene via homologous recombination. Vectors are selected on the basis of a tk-phenotype. Inclusion of the untranslated leader sequence of encephalomyocarditis virus, the level of expression is higher than that of conventional vectors, with the transgenes accumulating at 10% or more of the infected cell's protein in 24 h (Elroy-Stein et al., 1989).

6. Gene Delivery Using Modified Viruses

A SEMA3B-encoding nucleic acid may be housed within a viral vector that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

7. Non-Viral Methods for Transfer of Expression Constructs

In certain embodiments, a plasmid vector is contemplated for use in transferring SEMA3B to cancer cells. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. pBR322, a plasmid derived from an *E. coli* species, is an example of on such vector. pBR322 contains genes for ampicillin and tetracycline resistance and thus provides easy means for identifying transformed cells. The pBR plasmid, or other microbial plasmids or phage must also contain, or be modified to contain, for example, promoters which can be used by the host cell for the expression of transgenes.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Several non-viral methods for the transfer of expression constructs into mammalian cells also are contemplated by the present invention. In one embodiment, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest also may be transferred in a similar manner in vivo and express the gene product.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection. Of particular interest are the methods and compositions disclosed in PCT/US00/14350, incorporated by reference herein.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993). Receptor-mediated gene targeting vehicles generally consist of two components: a cell receptor-specific ligand and a DNA-binding agent. In other embodiments, the delivery vehicle may comprise a ligand and a liposome.

IV. Recombinant Polypeptide Expression

The ability to produce biologically active SEMA3B polypeptide is an important aspect of the present invention. Development of mammalian cell culture for production of proteins has been greatly aided by the development in molecular biology of techniques for design and construction of vector systems highly efficient in mammalian cell cultures, a battery of useful selection markers, gene amplification schemes and a more comprehensive understanding of the biochemical and cellular mechanisms involved in procuring the final biologically-active molecule from the introduced vector. Such techniques and reagents are described elsewhere in this document.

The present invention can further take advantage of the biochemical and cellular capacities of cells to secrete SEMA3B, as well as of available bioreactor technology. Growing cells in a bioreactor allows for large scale production and secretion of complex, fully biologically-active SEMA3B polypeptides into the growth media. Thus, engineered cells can act as factories for the production of large amounts of SEMA3B.

A. Anchorage-Dependent Versus Non-Anchorage-Dependent Cultures

Animal and human cells can be propagated in vitro in two modes: as non-anchorage dependent cells growing freely in suspension throughout the bulk of the culture; or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. Large scale suspension culture based on microbial (bacterial and yeast) fermentation technology has clear advantages for the manufacturing of mammalian cell products. The processes are relatively simple to operate and straightforward to scale up. Homogeneous conditions can be provided in the reactor which allows for precise monitoring and control of temperature, dissolved oxygen, and pH, and ensure that representative samples of the culture can be taken.

However, suspension cultured cells cannot always be used in the production of biologicals. Suspension cultures are still considered to have tumorigenic potential and thus their use as substrates for production put limits on the use of the resulting products in human and veterinary applications (Petricciani, 1985; Larsson and Litwin, 1987). Viruses propagated in suspension cultures as opposed to anchorage-dependent cultures can sometimes cause rapid changes in viral markers, leading to reduced immunogenicity (Bahnemann, 1980). Finally, sometimes even recombinant cell lines can secrete considerably higher amounts of products when propagated as anchorage-dependent cultures as compared with the same cell line in suspension (Nilsson and Mosbach, 1987). For these reasons, different types of anchorage-dependent cells are used extensively in the production of different biological products.

B. Reactors and Processes for Suspension

Large scale suspension culture of mammalian cultures in stirred tanks may be undertaken. The instrumentation and controls for bioreactors can be adapted, along with the design of the fermentors, from related microbial applications. However, acknowledging the increased demand for contamination control in the slower growing mammalian cultures, improved aseptic designs must be implemented, improving dependability of these reactors. Instrumentation and controls are basically the same as found in other fermentors and include agitation, temperature, dissolved oxygen, and pH controls. More advanced probes and autoanalyzers for on-line and off-line measurements of turbidity (a function of particles present), capacitance (a function of viable cells present), glucose/lactate, carbonate/bicarbonate and carbon dioxide are available. Maximum cell densities obtainable in suspension cultures are relatively low at about $2-4\times10^6$ cells/ml of medium (which is less than 1 mg dry cell weight per ml), well below the numbers achieved in microbial fermentation.

Two suspension culture reactor designs are most widely used in the industry due to their simplicity and robustness of operation—the stirred reactor and the airlift reactor. The stirred reactor design has successfully been used on a scale of 8000 liter capacity for the production of interferon (Phillips et al., 1985; Mizrahi, 1983). Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcorner section of the reactor. The main advantage of this design is the simplicity and lack of need for mechanical mixing. Typically, the height-to-diameter ratio is 10:1. The airlift reactor scales up relatively easy, has good mass transfer of gasses and generates relatively low shear forces.

Most large-scale suspension cultures are operated as batch or fed-batch processes because they are the most straightforward to operate and scale up. However, continuous processes based on chemostat or perfusion principles are available.

A batch process is a closed system in which a typical growth profile is seen. A lag phase is followed by exponential, stationary and decline phases. In such a system, the environment is continuously changing as nutrients are depleted and metabolites accumulate. This makes analysis of factors influencing cell growth and productivity, and hence optimization of the process, a complex task. Productivity of a batch process may be increased by controlled feeding of key nutrients to prolong the growth cycle. Such a fed-batch process is still a closed system because cells, products and waste products are not removed.

In what is still a closed system, perfusion of fresh medium through the culture can be achieved by retaining the cells with a fine mesh spin filter and spinning to prevent clogging. Spin filter cultures can produce cell densities of approximately $5 \times 10^7$ cells/ml. A true open system and the simplest perfusion process is the chemostat in which there is an inflow of medium and an outflow of cells and products. Culture medium is fed to the reactor at a predetermined and constant rate which maintains the dilution rate of the culture at a value less than the maximum specific growth rate of the cells (to prevent washout of the cells mass from the reactor). Culture fluid containing cells and cell products and byproducts is removed at the same rate. These perfused systems are not in commercial use for production from mammalian cell culture.

C. Non-Perfused Attachment Systems

Traditionally, anchorage-dependent cell cultures are propagated on the bottom of small glass or plastic vessels. The restricted surface-to-volume ratio offered by classical and traditional techniques, suitable for the laboratory scale, has created a bottleneck in the production of cells and cell products on a large scale. In an attempt to provide systems that offer large accessible surfaces for cell growth in small culture volume, a number of techniques have been proposed: the roller bottle system, the stack plates propagator, the spiral film bottles, the hollow fiber system, the packed bed, the plate exchanger system, and the membrane tubing reel. Since these systems are non-homogeneous in their nature, and are sometimes based on multiple processes, they suffer from the following shortcomings—limited potential for scale-up, difficulties in taking cell samples, limited potential for measuring and controlling the system and difficulty in maintaining homogeneous environmental conditions throughout the culture.

Despite these drawbacks, a commonly used process of these systems is the roller bottle. Being little more than a large, differently shaped T-flask, simplicity of the system makes it very dependable and, hence, attractive. Fully automated robots are available that can handle thousands of roller bottles per day, thus eliminating the risk of contamination and inconsistency associated with the otherwise required intense human handling. With frequent media changes, roller bottle cultures can achieve cell densities of close to $0.5 \times 10^6$ cells/cm$^2$ (corresponding to $10^9$ cells/bottle or $10^7$ cells/ml of culture media).

D. Cultures on Microcarriers

In an effort to overcome the shortcomings of the traditional anchorage-dependent culture processes, van Wezel (1967) developed the concept of the microcarrier culturing systems. In this system, cells are propagated on the surface of small solid particles suspended in the growth medium by slow agitation. Cells attach to the microcarriers and grow gradually to confluency of the microcarrier surface. In fact, this large scale culture system upgrades the attachment dependent culture from a single disc process to a unit process in which both monolayer and suspension culture have been brought together. Thus, combining the necessary surface for as the cells grow with the advantages of the homogeneous suspension culture increases production.

The advantages of microcarrier cultures over most other anchorage-dependent, large-scale cultivation methods are several fold. First, microcarrier cultures offer a high surface-to-volume ratio (variable by changing the carrier concentration) which leads to high cell density yields and a potential for obtaining highly concentrated cell products. Cell yields are up to $1-2 \times 10^7$ cells/ml when cultures are propagated in a perfused reactor mode. Second, cells can be propagated in one unit process vessels instead of using many small low-productivity vessels (i.e., flasks or dishes). This results in far better utilization and a considerable saving of culture medium. Moreover, propagation in a single reactor leads to reduction in need for facility space and in the number of handling steps required per cell, thus reducing labor cost and risk of contamination. Third, the well-mixed and homogeneous microcarrier suspension culture makes it possible to monitor and control environmental conditions (e.g., pH, pO$_2$, and concentration of medium components), thus leading to more reproducible cell propagation and product recovery. Fourth, it is possible to take a representative sample for microscopic observation, chemical testing, or enumeration. Fifth, since microcarriers settle out of suspension easily, use of a fed-batch process or harvesting of cells can be done relatively easily. Sixth, the mode of the anchorage-dependent culture propagation on the microcarriers makes it possible to use this system for other cellular manipulations, such as cell transfer without the use of proteolytic enzymes, cocultivation of cells, transplantation into animals, and perfusion of the culture using decanters, columns, fluidized beds, or hollow fibers for microcarrier retainment. Seventh, microcarrier cultures are relatively easily scaled up using conventional equipment used for cultivation of microbial and animal cells in suspension.

E. Microencapsulation of Mammalian Cells

One method which has shown to be particularly useful for culturing mammalian cells is microencapsulation. The mammalian cells are retained inside a semipermeable hydrogel membrane. A porous membrane is formed around the cells permitting the exchange of nutrients, gases, and metabolic products with the bulk medium surrounding the capsule. Several methods have been developed that are gentle, rapid and non-toxic and where the resulting membrane is sufficiently porous and strong to sustain the growing cell mass throughout the term of the culture. These methods are all based on soluble alginate gelled by droplet contact with a calcium-containing solution. describes cells concentrated in an approximately 1% solution of sodium alginate which are forced through a small orifice, forming droplets, and breaking free into an approximately 1% calcium chloride solution. The droplets are then cast in a layer of polyamino acid that ionically bonds to the surface alginate. Finally the alginate is reliquefied by treating the droplet in a chelating agent to remove the calcium ions. Other methods use cells in a calcium solution to be dropped into an alginate solution, thus creating a hollow alginate sphere. A similar approach involves cells in a chitosan solution dropped into alginate, also creating hollow spheres.

Microencapsulated cells are easily propagated in stirred tank reactors and, with beads sizes in the range of 150-1500 µm in diameter, are easily retained in a perfused reactor using a fine-meshed screen. The ratio of capsule volume to total media volume can kept from as dense as 1:2 to 1:10. With intracapsular cell densities of up to $10^8$, the effective cell density in the culture is $1\text{-}5\times10^7$.

The advantages of microencapsulation over other processes include the protection from the deleterious effects of shear stresses which occur from sparging and agitation, the ability to easily retain beads for the purpose of using perfused systems, scale up is relatively straightforward and the ability to use the beads for implantation.

F. Perfused Attachment Systems

Perfusion refers to continuous flow at a steady rate, through or over a population of cells (of a physiological nutrient solution). It implies the retention of the cells within the culture unit as opposed to continuous-flow culture which washes the cells out with the withdrawn media (e.g., chemostat). The idea of perfusion has been known since the beginning of the century, and has been applied to keep small pieces of tissue viable for extended microscopic observation. The technique was initiated to mimic the cells milieu in vivo where cells are continuously supplied with blood, lymph, or other body fluids. Without perfusion, cells in culture go through alternating phases of being fed and starved, thus limiting full expression of their growth and metabolic potential. The current use of perfused culture is in response to the challenge of growing cells at high densities (i.e., $0.1\text{-}5\times10^8$ cells/ml). In order to increase densities beyond $2\text{-}4\times10^6$ cells/ml (or $2\times10^5$ cells/$cm^2$), the medium has to be constantly replaced with a fresh supply in order to make up for nutritional deficiencies and to remove toxic products. Perfusion allows for a far better control of the culture environment (pH, $pO_2$, nutrient levels, etc.) and is a means of significantly increasing the utilization of the surface area within a culture for cell attachment.

Microcarrier and microencapsulated cultures are readily adapted to perfused reactors but, as noted above, these culture methods lack the capacity to meet the demand for cell densities above $10^8$ cells/ml. Such densities will provide for the advantage of high product titer in the medium (facilitating downstream processing), a smaller culture system (lowering facility needs), and a better medium utilization (yielding savings in serum and other expensive additives). Supporting cells at high density requires extremely efficient perfusion techniques to prevent the development of non-homogeneity. This means the use of highly sophisticated procedures and apparati and has, until recently, been confined to a relatively small scale.

G. CelliGen™ Bioreactor System

The development of a perfused packed-bed reactor using a bed matrix of a non-woven fabric has provided a means for maintaining a perfusion culture at densities exceeding $10^8$ cells/ml of the bed volume (CelliGen™, New Brunswick Scientific, Edison, N.J.; Wang et al., 1992; Wang et al, 1993; Wang et al., 1994). Briefly described, this reactor comprises an improved reactor for culturing of both anchorage- and non-anchorage-dependent cells. The reactor is designed as a packed bed with a means to provide internal recirculation. Preferably, a fiber matrix carrier is placed in a basket within the reactor vessel. A top and bottom portion of the basket has holes, allowing the medium to flow through the basket. A specially designed impeller provides recirculation of the medium through the space occupied by the fiber matrix for assuring a uniform supply of nutrient and the removal of wastes. This simultaneously assures that a negligible amount of the total cell mass is suspended in the medium. The combination of the basket and the recirculation also provides a bubble-free flow of oxygenated medium through the fiber matrix. The fiber matrix is a non-woven fabric having a "pore" diameter of from 10 µm to 100 µm, providing for a high internal volume with pore volumes corresponding to 1 to 20 times the volumes of individual cells.

In comparison to other culturing systems, this approach offers several significant advantages. With a fiber matrix carrier, the cells are protected against mechanical stress from agitation and foaming. The free medium flow through the basket provides the cells with optimum regulated levels of oxygen, pH, and nutrients. Products can be continuously removed from the culture and the harvested products are free of cells and produced in low-protein medium which facilitates subsequent purification steps. Also, the unique design of this reactor system offers an easier way to scale up the reactor. Currently, sizes up to 30 liter are available. One hundred liter and 300 liter versions are in development and theoretical calculations support up to a 1000 liter reactor. This technology is explained in detail in WO 94/17178 (Freedman et al.), which is hereby incorporated by reference in its entirety.

A number of culturing parameters, used in conjunction the CelliGen™ system, have been demonstrated to play a role in increased production. For example, the CelliGen™ Plus reactor system, including the use of non-woven polyester fiber matrix (preferably, Fibra-Cel™) and centrifugal lift impeller (preferably, Fibra-Cel™) are system components that give improved yields. Also, several media formulations have been employed with improved performance. For example, use of serum free medium is preferred, as is the use of cholesterol rich lipid extract (0.01% to 0.10%, volume to volume), ascorbic acid (from between about 0.001 to 0.100 mM), glutamate (rather than 2 mM glutamine) at 2 to 20 mM, preferably 4 mM, alpha ketoglutarate (rather than 2 mM glutamine) at 2 to 20 mM, preferably 4 mM, and the absence of growth promoting factors.

H. CellCube™ Bioreactor System

The CellCube™ (Corning-Costar) module provides a large styrenic surface area for the immobilization and growth of substrate attached cells. It is an integrally encapsulated sterile single-use device that has a series of parallel culture plates joined to create thin, sealed laminar flow spaces between adjacent plates. The CellCube™ module has inlet and outlet ports that are diagonally opposite each other and help distribute the flow of media to the parallel plates. The medium is constantly recirculated from the module through an oxygenator and back to the cube. The external oxygenator provides a bubble free stream of oxygenated medium and allows for the additional control of the pH of the medium. With concurrent addition of fresh medium, medium with secreted product and wastes can be harvested continuously, retaining the cell population in the cube.

During the first few days of growth, the culture is generally satisfied by the media contained within the system after initial seeding. The amount of time between the initial seeding and the start of the media perfusion is dependent on the density of cells in the seeding inoculum and the cell growth rate. The measurement of nutrient concentration in the circulating media is a good indicator of the status of the culture. When establishing a procedure it may be necessary to monitor the nutrient composition at a variety of different perfusion rates to determine the most economical and productive operating parameters.

Cells within the system reach a higher density of solution (cells/ml) than in traditional culture systems. Many typically used basal media are designed to support $1\text{-}2\times10^6$ cells/ml/day. A typical CellCube™ run with an 21 000 $cm^2$ surface, contains approximately 1.2 liters of media within the module. The final cell density can exceed $2.5\times10^6$ cell/$cm^2$ or $5\times10^7$ cells/ml in the culture vessel. At confluence, depending on the cell line used, media required can vary anywhere form 4-16 module volumes per day.

The advantage of the CellCube™ system is that it to a large extent replicates the conditions the cells experience in T flask culture. This allows for very linear scale up of any culture that is successfully grown in flask culture without severe loss in per-cell performance.

V. Protein Purification

Protein purification techniques are well known to those of skill in the art. These techniques tend to involve the fractionation of the cellular milieu to separate SEMA3B from other components of the mixture. Having separated SEMA3B from gross impurities, the sample may be further purified using chromatographic and electrophoretic techniques to achieve more complete purification. Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

The term "purified," as used herein, is intended to refer to the state of a composition, isolatable from other components, wherein the composition is purified to any degree relative to its naturally-obtainable state. A purified SEMA3B protein therefore also refers to a protein or peptide, free from the environment in which it may naturally occur. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of SEMA3B antibodies that would be suitable for use in accordance with the present invention is discussed below.

VI. Antibody Production

It will be understood that polyclonal or monoclonal antibodies that bind to the SEMA3B and related proteins that are expressed in cancer cells will have utilities in several applications. These include the production of diagnostic kits for use in detecting and diagnosing cancer. Thus, the invention further provides antibodies against SEMA3B polypeptides or peptides. Means for preparing and characterizing antibodies are well known in the art (See, e.g., Antibodies: A Laboratory Manual, Cold Spring Harbor Laboratory, 1988; incorporated herein by reference).

A polyclonal antiserum is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep, goat, monkey cells also is possible. The use of rats may provide certain advantages (Goding, 1986, pp. 60-61), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens or lymph nodes. Spleen cells and lymph node cells are preferred, the former because they are a rich source of antibody-producing cells that are in the dividing plasmablast stage.

Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984; each incorporated herein by reference). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bu1; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like. The selected hybridomas would then be serially diluted and cloned into individual antibody-producing cell lines, which clones can then be propagated indefinitely to provide MAbs. The cell lines may be exploited for MAb production in two basic ways.

MAbs produced by either means may be further purified, if desired, using filtration, centrifugation and various chromatographic methods such as HPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobin preparations and U.S. Pat. No. 4,867,973 which describes antibody-therapeutic agent conjugates.

U.S. Pat. No. 5,565,332 describes methods for the production of antibodies, or antibody fragments, which have the same binding specificity as a parent antibody but which have increased human characteristics. Humanized antibodies may be obtained by chain shuffling, perhaps using phage display technology, in as much as such methods will be useful in the present invention the entire text of U.S. Pat. No. 5,565,332 is incorporated herein by reference.

VII. Screening Methods

The present invention further comprises methods for identifying modulators of the function of SEMA3B. These assays may comprise random screening of large libraries of candidate substances; alternatively, the assays may be used to focus on particular classes of compounds selected with an eye towards structural attributes that are believed to make them more likely to modulate the function of this molecule. By function, it is meant that one may assay for affects on tumor suppression by SEMA3B.

To identify a modulator, one generally will determine the function of SEMA3B in the presence and absence of the candidate substance, a modulator defined as any substance that alters function. For example, a method generally comprises:

(a) providing a candidate modulator;
(b) admixing the candidate modulator with an isolated compound or cell, or a suitable experimental animal;
(c) measuring one or more characteristics of the compound, cell or animal in step (c); and
(d) comparing the characteristic measured in step (c) with the characteristic of the compound, cell or animal in the absence of said candidate modulator,
wherein a difference between the measured characteristics indicates that said candidate modulator is, indeed, a modulator of the compound, cell or animal.

Such characteristics will include cell proliferation, colony formation, cell viability, cell morphology or other appropriate indicator.

It will, of course, be understood that all the screening methods of the present invention are useful in themselves notwithstanding the fact that effective candidates may not be found. The invention provides methods for screening for such candidates, not solely methods of finding them.

1. Modulators

As used herein the term "candidate modulator" refers to any molecule that may potentially inhibit or enhance SEMA3B activity. The candidate substance may be a protein or fragment thereof, a small molecule, or even a nucleic acid molecule. It may prove to be the case that the most useful pharmacological compounds will be compounds that are structurally related to SEMA3B, i.e., mimics. Using lead compounds to help develop improved compounds is known as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single-chain antibodies or expression constructs coding thereof), each of which would be specific for a given target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one which exerts its inhibitory or activating effect upstream, downstream or directly on SEMA3B. Regardless of the type of inhibitor or activator identified by the present screening methods, the effect of the inhibition or activator by such a compound results in an alteration in growth control as compared to that observed in the absence of the added candidate substance.

2. In Vitro Assays

A quick, inexpensive and easy assay to run is an in vitro assay. Such assays can be run quickly and in large numbers, thereby increasing the amount of information obtainable in a short period of time. A variety of vessels may be used to run the assays, including test tubes, plates, dishes and other surfaces such as dipsticks or beads. One example of a cell free assay is a binding assay. While not directly addressing function, the ability of a modulator to bind to a SEMA3B target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

3. In Cyto Assays

The present invention also contemplates the screening of compounds for their ability to modulate SEMA3B function in cells. Various cell lines can be utilized for such screening assays, including cells specifically engineered for this purpose. For example, for substances that may activate SEMA3B transcription, reporter cell lines using the SEMA3B promoter operationally linked to DNA segment encoding a screenable marker protein may prove most useful.

Depending on the assay, culture may be required. The cell may be examined using any of a number of different physiologic assays, as discussed above for inhibition of cancer cell phenotypes. Alternatively, molecular analysis may be performed, for example, looking at protein expression, mRNA expression (including differential display of whole cell or polyA RNA) and others.

4. In Vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the function of a particular compound (e.g., enzyme, receptor, hormone) or cell (e.g., growth, tumorigenicity, survival), or instead a broader indication such as behavior, anemia, immune response, etc.

The present invention provides methods of screening for a candidate substance that can increase the expression of SEMA3B in cells. Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal. inhalation or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

VIII. Therapeutic Methods

The present invention provides at least three distinct primary therapies for cancer. First, in accordance with the inventors' observations, a protein based therapy may be applied. This may involve the use of purified or semi-purified SEMA3B polypeptide. Alternatively, given that SEMA3B is a secreted protein, one may simply obtain the medium in which SEMA3B-expressing cells are grown. Provision of either composition to patients, as described below, will effect a therapeutic effect (e.g., inhibition of tumor formation, growth or metastasis, tumor regression, tumor cell death). In a distinct embodiment, gene therapy using a SEMA3B-encoding DNA sequence may be conducted. Various vectors for gene transfer, and methods for introduction of such vectors into cells, are described elsewhere in this document. A third embodiment, involves the provision of one or more drugs which increase expression or activity of SEMA3B. These may be small molecules that stabilize SEMA3B, that mimic the activity of SEMA3B, or that alter methylation patterns in SEMA3B transcriptional control regions, thereby facilitating increased transcription. Examples of such methylation modulators are 5-azacytidine and various histone deacetylase inhibitors, such as trichostatin A, trapoxin B, MS 275-27, m-carboxycinnamic acid bis-hydroxamide, depudecin, oxamflatin, apicidin, suberoylanilide hydroxamic acid, Scriptaid, pyroxamide, 2-amino-8-oxo-9,10-epoxy-decanoyl, 3-(4-aroyl-1 H-pyrrol-2-yl)-N-hydroxy-2-propenamide and FR901228.

The present invention finds principal use in lung cancers and mesotheliomas. However, various other cancers may also benefit from SEMA3B therapies, such as breast cancer, prostate cancer, ovarian cancer, brain cancer, liver cancer, prostate cancer, cervical cancer, colon cancer, renal cancer, skin cancer, head & neck cancer, bone cancer, esophageal cancer, bladder cancer, uterine cancer, lymphatic cancer, stomach cancer, pancreatic cancer and testicular cancer. While cancers that lack SEMA3B activity will be obvious targets for therapy, overexpression of SEMA3B in cancers that have normal or reduced levels of SEMA3B also is contemplated.

SEMA3B protein, gene or drug therapy may be provided more than one time, and they may be provided together as part of the same therapy regimen. For example, one may provide alternating doses of SEMA3B protein, vector or drug, or one may provide repeated dosings in a mono-therapy.

A. Pharmaceutical Composition and Routes of Administration

Pharmaceutical compositions of the present invention comprise an effective amount of a SEMA3B polypeptide or expression construct dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The pharmaceutical compositions of the present invention may comprise different types of carriers depending on whether they are to be administered in solid, liquid or aerosol form, and whether it needs to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, locally, regional to a tumor site, by inhalation (e.g., aerosol inhalation), injection, infusion, continuous infusion, localized perfusion, bathing target cells directly, via catheter, via lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments, the compositions may be prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a flavoring agent, a dye, a preservative, or combinations thereof.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area. In particular embodiments, prolonged absorption of an injectable composition can be brought about by the use in the compositions of agents delaying absorption, such as, for example, aluminum monostearate, gelatin or combinations thereof.

The composition should also be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

B. Combination Therapies

In order to increase the effectiveness of SEMA3B polypeptide or gene therapy, it may be desirable to combine such compositions with other agents effective in the treatment of cancer. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these agents would be provided in a combined amount effective to kill or inhibit proliferation of the cell. This process may involve contacting the cells with the SEMA3B polypeptide or expression construct and the agent at the same time. This may be achieved by contacting the cell with a single composition or pharmacological formulation that includes both agents, or by contacting the cell with two distinct compositions or formulations, at the same time, wherein one composition includes the expression construct and the other includes the second agent.

Alternatively, the SEMA3B therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 hr of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, SEMA3B protein or gene therapy is "A" and the secondary agent is "B":

```
A/B/A  B/A/B  B/B/A  A/A/B  A/B/B  B/A/A  A/B/B/B
B/A/B/B       B/B/B/A       B/B/A/B       A/A/B/B       A/B/A/B
A/B/B/A       B/B/A/A       B/A/B/A       B/A/A/B       A/A/A/B
B/A/A/A       A/B/A/A       A/A/B/A
```

It is expected that the treatment cycles would be repeated as necessary. The following sections describe various therapies for use in combination with the present invention.

1. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, navelbine, gencitibine, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, tyrosine kinase inhibitors, VEG-F inhibitors, vincristin, vinblastin and methotrexate, or any analog or derivative variant of the foregoing compounds.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

3. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with SEMA3B therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

4. Genes

In yet another embodiment, the secondary treatment is a gene therapy in which a non-SEMA3B expression construct is administered before, after, or at the same time a SEMA3B polypeptide or expression construct. Where a SEMA3B gene therapy is used, delivery may comprise use of a vector encoding SEMA3B in conjunction with a second vector encoding one of the following gene products. Alternatively, a single vector encoding both genes may be used. A variety of secondary gene therapy proteins are envisioned within the invention, some of which are described below.

i. Inducers of Cellular Proliferation

The proteins that induce cellular proliferation further fall into various categories dependent on function. The commonality of all of these proteins is their ability to regulate cellular proliferation. For example, a form of PDGF, the sis proto-oncogene, is a secreted growth factor. Oncogenes rarely arise from genes encoding growth factors, and at the present, sis is the only known naturally-occurring oncogenic growth factor. In one embodiment of the present invention, it is contemplated that antisense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

ii. Inhibitors of Cellular Proliferation

The tumor suppressors function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue.

Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDKs. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $p15^{INK4}$, $p18^{INK4}$, p19, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Okamoto et al., 1994; Nobori et al., 1994; Orlow et al., 1994; Arap et al., 1995). Restoration of wild-type $p16^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p73, FHIT, FUS-1, CACNA2D2, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

iii. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

5. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue. The SEMA3B therapies disclosed herein also be used to render an inoperative tumor operative.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

6. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

IX. Diagnostic Methods

The present invention also provides for methods of diagnosis. It is well known that mutations occur in the 3p chromosome region in cancers. However, previous work does not provide a definitive demonstration that SEMA3B is, in fact, a tumor suppressor gene (TSG). With the information provided herein, it is now clear that SEMA3B is a bona fide TSG. As such, the present invention focuses diagnostic methods on SEMA3B to determine with it is mutated, or its expression is reduced, either of which can indicate that an individual is at risk for or suffers from cancer.

A. Immunologic Methods

In one embodiment, the present invention concerns immunodetection of SEMA3B for the prognosis or diagnosis of cancer. SEMA3B antibodies prepared in accordance with the present invention (described above) may be employed to detect the amount of SEMA3B in a sample. Alternatively, the antibodies may be directed to particular epitopes that are altered in cancerous tissues, either by mutation of residues required for binding of an antibody, or through loss of secondary or tertiary structure in discontinuous epitopes. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev, 1999; Gulbis and Galand, 1993; De Jager et al., 1993; Nakamura et al., 1987, each incorporated herein by reference.

In general, the methods include obtaining a sample suspected of containing SEMA3B protein and contacting the sample with a first anti-SEMA3B antibody in accordance with the present invention, under conditions effective to allow the formation of immunocomplexes. The antibody may be linked to a solid support, such as in the form of a column matrix, plate or dipstick. The unwanted components of the sample are washed away, leaving the SEMA3B antigen immunocomplexed to the immobilized antibody.

The immunobinding methods also include methods for quantifying the amount of a SEMA3B in a sample. Here, one would obtain a sample suspected of containing SEMA3B, contact the sample with an antibody SEMA3B, and then quantify the amount of immune complexes formed under the specific conditions. Quantification may be by use of labels, from which radioactive or fluorescent emissions are measured.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, SEMA3B antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand-binding arrangement, as is known in the art.

As stated above, the SEMA3B antibody employed in the detection may be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

1. ELISAs

As detailed above, immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and/or western blotting, dot blotting, FACS analyses, and the like may also be used.

In one exemplary ELISA, the anti-SEMA3B antibodies of the invention are immobilized onto a selected surface exhibiting protein affinity, such as a well in a polystyrene microtiter plate. Then, a test composition containing the SEMA3B protein antigen, such as a clinical sample, is added to the wells. After binding and washing to remove non-specifically bound immune complexes, the bound SEMA3B antigen may be detected. Detection is generally achieved by the addition of another anti-SEMA3B antibody that is linked to a detectable label. This type of ELISA is a simple "sandwich ELISA." Detection may also be achieved by the addition of a second unlabeled anti-SEMA3B antibody, followed by the addition of a third antibody that has binding affinity for the second antibody, with the third antibody being linked to a detectable label.

In another exemplary ELISA, the samples containing SEMA3B antigen are immobilized onto the well surface and then contacted with the anti-SEMA3B antibodies of the invention. After binding and washing to remove non-specifically bound immune complexes, the bound anti-SEMA3B antibodies are detected. Where the initial anti-SEMA3B antibodies are linked to a detectable label, the immune complexes may be detected directly. Again, the immune complexes may be detected using a second antibody that has binding affinity for the first anti-SEMA3B antibody, with the second antibody being linked to a detectable label.

Another ELISA in which SEMA3B polypeptides are immobilized involves the use of antibody competition in the detection. In this ELISA, labeled antibodies against SEMA3B are added to the wells, allowed to bind, and detected by means of their label. The amount of SEMA3B in an unknown sample is then determined by mixing the sample with the labeled antibodies against SEMA3B before and during incubation with coated wells. The presence of SEMA3B in the sample acts to reduce the amount of antibody against SEMA3B available for binding to the well, and thus reduces the ultimate signal.

Irrespective of the format employed, ELISAs have certain features in common, such as coating, incubating and binding, washing to remove non-specifically bound species, and detecting the bound immune complexes. In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

2. Immunohistochemistry

The antibodies of the present invention may also be used in conjunction with both fresh-frozen and formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

3. Immunodetection Kits

In still further embodiments, the present invention concerns immunodetection kits for use with the immunodetection methods described above. SEMA3B antibodies will preferably be included in the kit. The immunodetection kits will thus comprise, in suitable container means, a first antibody that binds to a wild-type or mutant protein, and optionally, an immunodetection reagent.

In preferred embodiments, monoclonal antibodies will be used. In certain embodiments, the SEMA3B antibody may be pre-bound to a solid support, such as a column matrix, dipstick or well of a microtitre plate.

The immunodetection reagents of the kit may take any one of a variety of forms, including those detectable labels that are associated with and/or linked to the given antibody. Detectable labels that are associated with and/or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present invention.

The kits may further comprise a suitably aliquoted composition of the wild-type or mutant SEMA3B polypeptide, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present invention will also typically include a means for containing the antibody, antigen, and any other reagent containers in close confinement for commercial sale. Such containers may include injection and blow-molded plastic containers into which the desired vials are retained.

B. Genetic Methods

In a second diagnostic embodiment, one may examine SEMA3B nucleic acid sequences. These nucleic acid sequences may be genomic sequences, or they may be transcribed sequences, i.e., mRNAs. The nucleic acids may be purified and separated, as in Southern and Northern blots, or they may be examined in situ, such as in immunohistochemistry. A wide variety of techniques may be applied to the genetic diagnosis of cancer, as discussed below.

1. Hybridization

An almost universal aspect of genetic diagnoses is hybridization of nucleic acid sequences. Various probes or primers of between 13 and 100 nucleotides, preferably between 17 and 100 nucleotides in length, or up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In specific embodiments, one may desire to employ a fluorescent label or an enzyme tag such as urease, alkaline phosphatase or peroxidase, instead of radioactive or other environmentally undesirable reagents. In the case of enzyme tags, calorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772.

DNA arrays and gene chip technology are particular solid phase applications. These materials provide a means of rapidly screening a large number of DNA samples for their ability to hybridize to a variety of DNA probes immobilized on a solid substrate. Specifically contemplated are chip-based DNA technologies such as those described by Hacia et al. (1996) and Shoemaker et al. (1996). These techniques involve quantitative methods for analyzing large numbers of genes rapidly and accurately. The technology capitalizes on the complementary binding properties of single-stranded DNA to screen DNA samples by hybridization. Pease et al. (1994); Fodor et al. (1991).

Basically, a DNA array or gene chip consists of a solid substrate upon which an array of single-stranded DNA molecules have been attached. For screening, the chip or array is contacted with a single-stranded DNA sample which is allowed to hybridize under stringent conditions. The chip or array is then scanned to determine which probes have hybridized. In a particular embodiment of the instant invention, a gene chip or DNA array would comprise probes specific for SEMA3B chromosomal or mRNA mutations evidencing the development of a neoplastic or preneoplastic phenotype. In the context of this embodiment, such probes could include synthesized oligonucleotides, cDNA, genomic DNA, yeast artificial chromosomes (YACs), bacterial artificial chromosomes (BACs), chromosomal markers or other constructs a person of ordinary skill would recognize as adequate to demonstrate a genetic change.

A variety of gene chip or DNA array formats are described in the art, for example U.S. Pat. Nos. 5,861,242 and 5,578,832 which are expressly incorporated herein by reference. A means for applying the disclosed methods to the construction of such a chip or array would be clear to one of ordinary skill in the art. In brief, the basic structure of a gene chip or array comprises: (1) an excitation source; (2) an array of probes; (3) a sampling element; (4) a detector; and (5) a signal amplification/treatment system. A chip may also include a support for immobilizing the probe.

In particular embodiments, a target nucleic acid may be tagged or labeled with a substance that emits a detectable signal, for example, luminescence. The target nucleic acid may be immobilized onto the integrated microchip that also supports a phototransducer and related detection circuitry. Alternatively, a gene probe may be immobilized onto a membrane or filter which is then attached to the microchip or to the detector surface itself. In a further embodiment, the immobilized probe may be tagged or labeled with a substance that emits a detectable or altered signal when combined with the target nucleic acid. The tagged or labeled species may be fluorescent, phosphorescent, or otherwise luminescent, or it may emit Raman energy or it may absorb energy. When the probes selectively bind to a targeted species, a signal is generated that is detected by the chip. The signal may then be processed in several ways, depending on the nature of the signal.

The DNA probes may be directly or indirectly immobilized onto a transducer detection surface to ensure optimal contact and maximum detection. The ability to directly synthesize on or attach polynucleotide probes to solid substrates is well known in the art. See U.S. Pat. Nos. 5,837,832 and 5,837,860, both of which are expressly incorporated by reference. A variety of methods have been utilized to either permanently or removably attach the probes to the substrate. Exemplary methods include: the immobilization of biotinylated nucleic acid molecules to avidin/streptavidin coated supports (Holmstrom, 1993), the direct covalent attachment of short, 5'-phosphorylated primers to chemically modified polystyrene plates (Rasmussen et al., 1991), or the precoating of the polystyrene or glass solid phases with poly-L-Lys or poly L-Lys, Phe, followed by the covalent attachment of either amino- or sulfhydryl-modified oligonucleotides using bi-functional crosslinking reagents (Running et al., 1990; Newton et al., 1993). When immobilized onto a substrate, the probes are stabilized and therefore may be used repeatedly. In general terms, hybridization is performed on an immobilized nucleic acid target or a probe molecule is attached to a solid surface such as nitrocellulose, nylon membrane or glass. Numerous other matrix materials may be used, including reinforced nitrocellulose membrane, activated quartz, activated glass, polyvinylidene difluoride (PVDF) membrane, polystyrene substrates, polyacrylamide-based substrate, other polymers such as poly(vinyl chloride), poly(methyl methacrylate), poly (dimethyl siloxane), photopolymers (which contain photoreactive species such as nitrenes, carbenes and ketyl radicals capable of forming covalent links with target molecules.

Binding of the probe to a selected support may be accomplished by any of several means. For example, DNA is commonly bound to glass by first silanizing the glass surface, then activating with carbodimide or glutaraldehyde. Alternative procedures may use reagents such as 3-glycidoxypropyltrimethoxysilane (GOP) or aminopropyltrimethoxysilane (APTS) with DNA linked via amino linkers incorporated either at the 3' or 5' end of the molecule during DNA synthesis. DNA may be bound directly to membranes using ultraviolet radiation. With nitrocellous membranes, the DNA probes are spotted onto the membranes. A UV light source (Stratalinker,™ Stratagene, La Jolla, Calif.) is used to irradiate DNA spots and induce cross-linking. An alternative method for cross-linking involves baking the spotted membranes at 80° C. for two hours in vacuum.

Specific DNA probes may first be immobilized onto a membrane and then attached to a membrane in contact with a transducer detection surface. This method avoids binding the probe onto the transducer and may be desirable for large-scale production. Membranes particularly suitable for this application include nitrocellulose membrane (e.g., from BioRad, Hercules, Calif.) or polyvinylidene difluoride (PVDF) (Bio-Rad, Hercules, Calif.) or nylon membrane (Zeta-Probe, Bio-Rad) or polystyrene base substrates (DNA.BIND™ Costar, Cambridge, Mass.).

2. Amplification of Nucleic Acids

Nucleic acids in samples often are present in small amounts. In order to increase the amount of material for testing, one may use sample DNA or RNA as a template for amplification. In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from 10 to 20 or 30 bases in length, but longer sequences can be employed. Primers may be provided in double-stranded and/or single-stranded form, although the single-stranded form is preferred.

Pairs of primers designed to selectively hybridize to nucleic acids corresponding to SEQ ID NOS:2 or 3 are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety. A reverse transcriptase PCR™ amplification procedure may be performed to quantify the amount of mRNA amplified. Methods of reverse transcribing RNA into cDNA are well known (see Sambrook et al., 2000). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Alternative methods for amplification of target nucleic acid sequences that may be used in the practice of the present invention are disclosed in U.S. Pat. Nos. 5,843,650, 5,846,709, 5,846,783, 5,849,497, 5,849,546, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

3. Detection of Nucleic Acids

Following any preprocessing of the nucleic acids (e.g., amplification), it may be desirable to separate the nucleic acids from other materials. In one embodiment, DNA or RNA can be separated by agarose, agarose-acrylamide or polyacrylamide gel electrophoresis using standard methods (Sambrook et al., 2000). Separated nucleic acids may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the nucleic acids are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of nucleic acids, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2000). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Other Assays

Other methods for genetic screening may be used within the scope of the present invention, for example, to detect mutations in genomic DNA, cDNA and/or RNA samples. Southern analysis of DNA, Northern analysis of RNA is well known to those of skill in the art. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

5. Immunochemistry

The diagnostics of present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections.

Permanent-sections may be prepared by a similar method involving rehydration of the 50 mg sample in a plastic microfuge tube; pelleting; resuspending in 10% formalin for 4 hr fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

6. Kits

All the essential materials and reagents required for detecting SEMA3B nucleotide sequences may be assembled together in a kit. This generally will comprise a probe or primers designed to hybridize specifically to individual nucleic acids of interest in the practice of the present invention, including those derived from SEQ ID NOS: 2 and 3. Also included may be enzymes suitable for amplifying nucleic acids, including various polymerases (reverse transcriptase, Taq, etc.), deoxynucleotides and buffers to provide the necessary reaction mixture for amplification. Such kits may also include enzymes and other reagents suitable for detection of specific nucleic acids or amplification products. Such kits generally will comprise, in suitable means, distinct containers for each individual reagent or enzyme as well as for each probe or primer pair.

X. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Figure 1B:
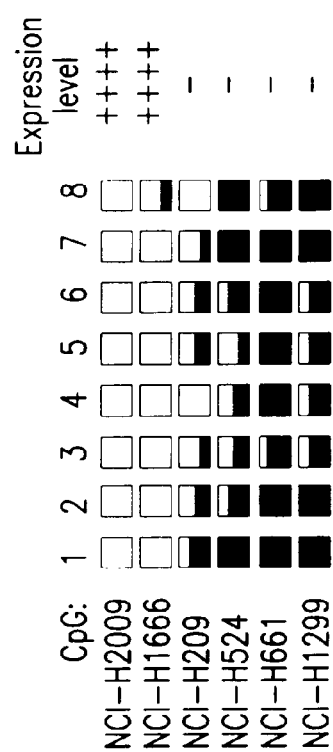

Analysis of CpG Methylation of the SEMA3B 5′-region. Genomic DNAs from lung cancer cell lines not expressing SEMA3B (NCI-H209, H524, H1299, H661), or expressing SEMA3B (H2009, H1666) (Sekido et al., 1996), were modified by sodium bisulfite treatment as described (Clark et al., 1994). Treated DNAs were PCR amplified with Primer M2AS (5′-TAACCCTAAAAATATACCCA-3′-SEQ ID NO:4) and Primer MS 1(5′-TATTTTAGTAGTTTAGGGTG-3′-SEQ ID NO:5) targeting a 269 bp sequence with multiple CpG sites immediately 5′ of the SEMA3B ATG. PCR cycling conditions consisted of 12 min, 95° C., followed by 40 cycles of 30 sec denaturation at 94° C., 30 sec annealing at 50° C., 30 sec extension at 72° C., with final extension at 72° C. for 10 min. The inventors re-amplified and sequenced the PCR product to obtain CpG methylation levels (FIGS. 1A-1B).

Analysis of Primary Lung Cancer Samples for SEMA3B Mutations. Forty-six primary lung tumors (9 SCLCs, 37 NSCLCs selected pathologically to contain ≧90% tumor tissue) and corresponding noncancerous tissue were obtained from the National Cancer Center Hospital (Tokyo, Japan), and genomic DNA prepared (Sakamoto et al., 1986). Seventeen genomic DNA fragments covering the entire coding region of SEMA3B were amplified by PCR with SEMA3B-specific oligonucleotide primers using exon/intron information from cDNA (U28369) and genomic (U73167) sequences, subjected to single stranded conformation polymorphism analysis, and abnormal bands sequenced.

Cell Lines. Lung cancer cell lines (Sekido et al., 1996; Phelps et al., 1996), were propagated in RPMI-1640 medium (Life Technologies, Inc., GIBCO BRL, Gaithersburg, Md.) supplemented with 10% fetal bovine serum (R10 medium). Normal human bronchial/tracheal epithelial cells (NHBE) (Clonetics, San Diego, Calif.) were propagated in Clonetics Growth Medium.

Expression Plasmids. Expression plasmids pcDNA3-SEMA3B (pCB 11, pSEMA3B) and pcDNA3-SEMA3B-antisense (pCB14, pSEMA3B-Antisense) (Sekido et al., 1996), and site-directed mutagenesis (Stratagene, La Jolla, Calif.) were used to make the mutant SEMA3B constructs (pSEMA3B-R348C, pSEMA3B-D397H, pSEMA3B-T415I, pSEMA3B-D561N) containing lung cancer single amino acid missense mutations (Sekido et al., 1996). A SEMA3F pcDNA3 expression construct (pSEMA3F) was also made. All constructs had their sequences confirmed through the PCR manipulated regions and all produced appropriately sized peptides detected in Western blotting by specific anti-SEMA3B or -SEMA3F antibodies after transfection.

Transfection and Colony Formation Assays. Transfections with DMRIE-C reagent (GIBCO Life Technologies, Inc.) used 2 μg of each plasmid per 10-cm dish containing $5 \times 10^5$ cells seeded 24 hr before transfection. Transfections were terminated at 5 hr, and 48 hr post-transfection, $5 \times 10^4$ transfected cells were seeded and maintained in R10 supplemented with 800 μg/ml G 418 (GIBCO Life Technologies, Inc.). Surviving colonies were counted 12-21 days later after staining with methylene blue.

Antibodies and Western Blot Analysis. The peptides corresponding to amino acid residues Thr 732 to Trp 749 of human SEMA3B (U28369) and Pro 722 to Lys 742 of SEMA3F (U38276) were synthesized and three rabbits immunized with each peptide (Alpha Diagnostic, San Antonio, Tex.). SEMA3B antisera were purified on immunoaffinity columns in which the peptide was covalently linked to Amino Link column (Pierce, Rockford, Ill.). Anti-NP1 and NP2 rabbit polyclonal antibodies were provided by Dr. A. Kolodkin. Cellular proteins were extracted from $10^6$ cells with 40 μl of lysis buffer (40 mM HEPES-NaOH, pH 7.4, 1% Nonidet P-40, 0.5% sodium deoxycholate, 0.1% sodium dodecyl sulfate, 150 mM NaCl, and 10 μg/ml aprotinin). Fifty μg of total protein per lane was separated on a 8% sodium dodecyl sulfate (SDS)/polyacrylamide gel and electroblotted to nitrocellulose membranes (Bio-Rad). After blocking with 5% nonfat dry milk and 0.1% Tween™ 20 in Tris-buffered saline, membranes were incubated at 37° C. for 2 hr with anti-NP1, anti-NP2 (Giger et al., 1998), anti-SEMA3B or anti-SEMA3F antibodies. The membranes were then developed with peroxidase-labeled anti-rabbit IgG (Amersham, Buckinghamshire, United Kingdom) by SuperSignal™ chemiluminescence substrate (Pierce, Rockford, Ill.). Equal loading of protein was confirmed after detection by staining the membrane with amido black 10B (Sigma).

Cell Cycle Analysis. Cells were harvested 48 hr after the transfection, fixed with 50% ethanol, treated with 5 mg/ml RNAse A (Roche), stained with 50 µg/ml propidium iodide, and analyzed by flow cytometry for DNA synthesis and cell cycle status (FACSCaliber instrument, Becton Dickinson, San Jose, Calif., with CellQuest software.

TUNEL and Caspase-3 Apoptosis Assays. Cells were fixed 24 hr after the transfection with 4% paraformaldehyde (Sigma) solution in PBS for 1 hr at room temperature, treated with 0.3% $H_2O_2$-methanol solution, then permeabilized with 0.1% Triton X-100$^R$ in 0.1% sodium citrate solution for 2 min on ice. The terminal deoxynucleotidyl transferase-mediated dUTP with a fluorescein tag nick end labeling (TUNEL) assay (Boehringer Mannheim) was carried out following the manufacture's instruction. Caspase-3 activity was measured with an Apoalert Caspase-3 Colorimetric kits (CloneTech). $5 \times 10^5$ cells were transfected with empty or SEMA3B plasmids by lipofection. After 20 hr, cell lysates were prepared and pre-incubated with or without the caspase inhibitor DEVD-fmk (CloneTech) for 30 min. Then, DEVD-pNA, the caspase-3 substrate, was added to the samples, incubated for 1 hr, and product measured at 400 nm.

Example 2

Results

Methylation Status of CpG Sites in SEMA3B Non-Expressing Lung Cancers. The inventors determined the CpG methylation status in the 5'-region of SEMA3B by sequencing sodium bisulfite modified DNA from four lung cancer cell lines not expressing SEMA3B, as well as two lung cancer lines expressing SEMA3B (FIGS. 1A-1B). All of the SEMA3B non-expressing tumor cell lines exhibited methylation of almost all CpG dinucleotides in this region. The two tumor cell lines that did express SEMA3B were either not methylated at these CpG sites or else showed a single CpG site with a mixed methylation pattern.

Additional Mutations Found in SEMA3B in Primary Lung Tumors. Genomic DNA from 46 primary lung tumors was examined for mutations in SEMA3B by PCR-SSCP analysis and direct DNA sequencing. An acquired mutation in SEMA3B (nucleotide G1916A substitution leading to Asp561Asn amino acid change in the semaphorin domain of SEMA3B) was detected in 1 of 9 primary SCLCs (but not the normal tissue), and germline changes Thr415Ile, and a G to A substitution at the intron side of the exon 15/intron boundary were found in one NSCLC each. All three were associated with loss of the wild-type alleles in tumors. As discussed below, T415I and Asp561 Asn lead to loss of SEMA3B growth suppressing function.

Figure 2:
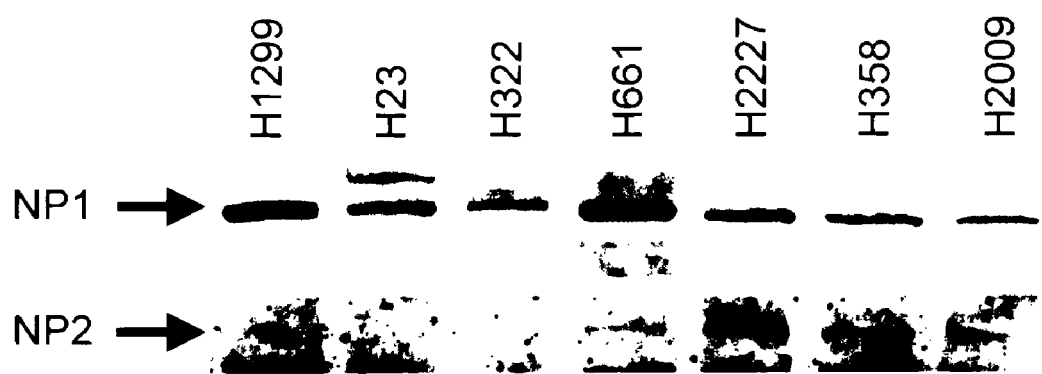
FIG. 2—Expression of neuropilin peptides in lung cancer cell lines by Western blotting (50 µg total cell lysate per lane). NCI-H1299, H23 and H322 express NP1 but not NP2 while H661, H2227, H358 and H2009 express both NP1 and NP2. Not shown are: SCLC lines expressing NP1 and NP2 NCI-H187, H209, H345, H378, H524, H526, H740, H865, H889, H1045, H1092, H1238, H1514, H1618, H1672, H2141, H2171, H2227; NSCLC lines expressing NP1 and NP2 H358, H838, H1437, H1792, H2009, H2077, H661, H2106, and H28 (mesothelioma). Lung cancer lines expressing NP1 but not NP2 are H1666, H460, and H2052 (mesothelioma).

Expression of Neuropilins in Lung Cancer Cell Lines. Because SEMA3 family members act through neuropilin receptors (and plexin co-receptors) (Tamagnone et al., 1999; Comoglio et al., 1999), the inventors examined the expression of NP1 and NP2 proteins in 18 SCLC, 14 NSCLC, and 2 mesothelioma cell lines, in which the expression of SEMA3B and SEMA3F mRNAs were also known (FIG. 2) (Sekido et al., 1996). NP1 was strongly expressed in all 34 cancer cell lines while NP2 was expressed to varying degrees in all SCLCs, 9 NSCLCs and 1 mesothelioma. The inventors found no correlation of expression patterns of SEMA3B, SEMA3F and the neuropilins.

Figure 3A:
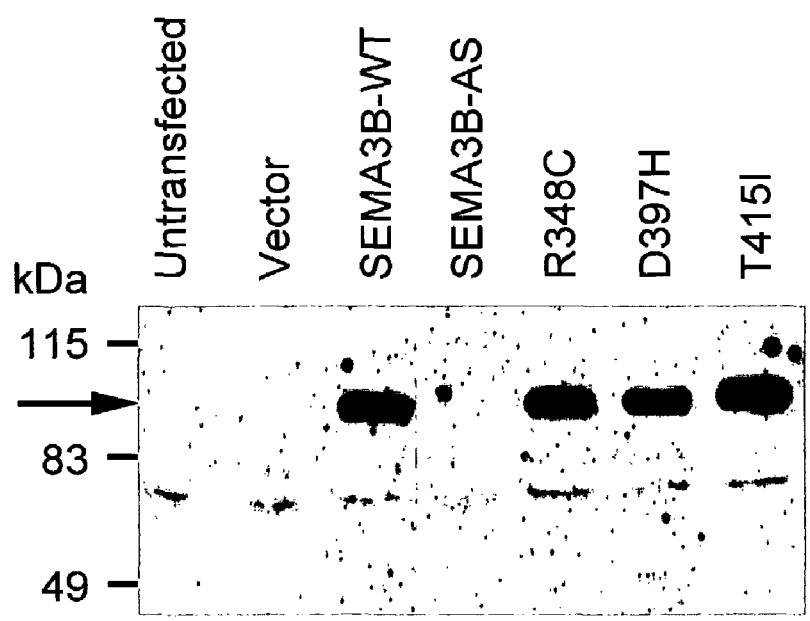
FIGS. 3A-3D—Effect of exogenous expression of SEMA3B and SEMA3F on the colony formation of H1299 NSCLC cells.
Figure 3B:
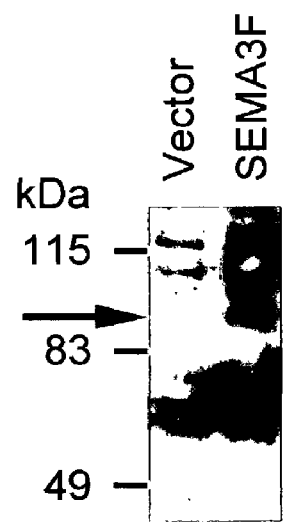
Figure 3C:
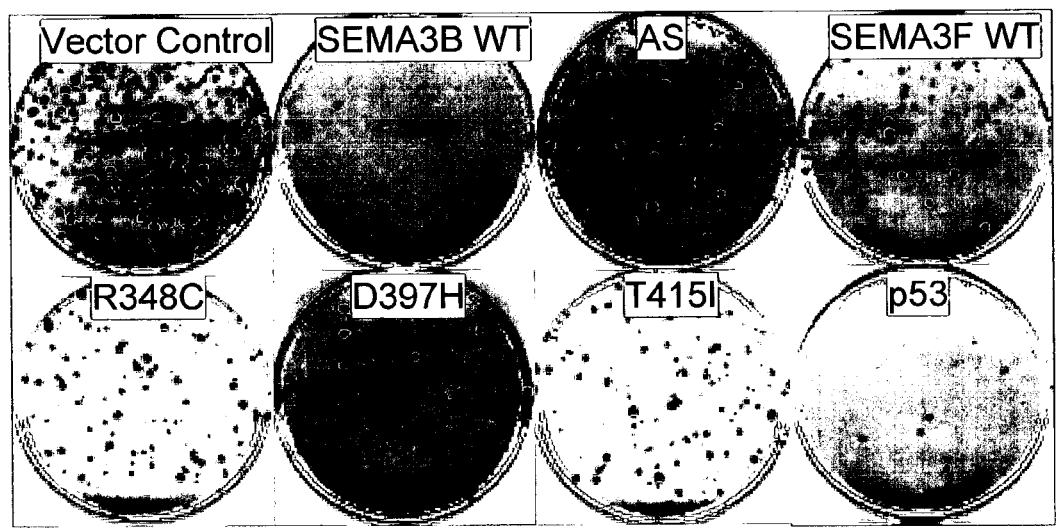
Figure 3D:
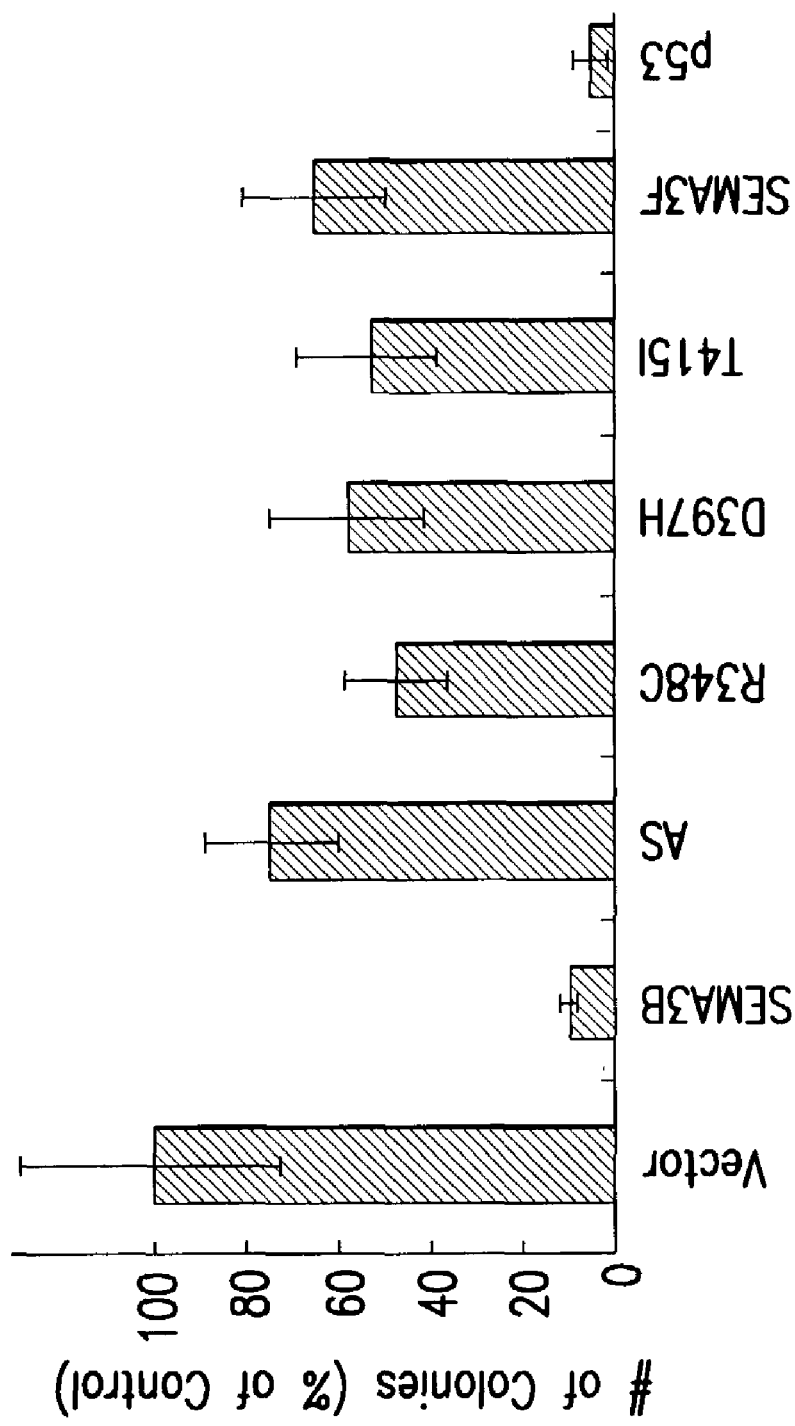

Inhibition of Colony Formation by SEMA3B in Lung Cancer Cell Lines. To test for the growth suppressive effect of ectopically expressed semaphorins, we performed colony formation assays selecting for the neo gene carried by our expression plasmids. Plasmids containing the full open reading frame of SEMA3B, anti-sense SEMA3B, the full open reading frame of SEMA3F and 4 SEMA3B constructs carrying lung cancer associated missense mutations were transfected into NSCLC NCI-H1299 cells which do not express endogenous SEMA3B or SEMA3F (Sekido et al., 1996). A positive control was wild-type p53 known to inhibit the growth and induce apoptosis of H1299 cells which contain a homozygous deletion of p53 (Chen et al., 1993). The wild-type SEMA3B and SEMA3F and mutant SEMA3B expression constructs all produced equivalent amounts of protein after transient transfection detected using affinity purified anti-SEMA3B or anti-SEMA3F antibodies (FIGS. 3A and 3B). Forty-eight hours after transfection, cells were selected with geneticin (G418) and resistant colonies developing 12 days later were stained. As expected, the wild-type p53 control dramatically suppressed colony formation (FIGS. 3C and 3D). In addition, the number of G418-resistant colonies after transfection with wild-type SEMA3B was reduced 90% compared to transfection with the control vector in five independent studies using three independent plasmid DNA preparations (FIGS. 3C and 3D). By contrast, four separate SEMA3B missense mutations had lost most of this colony suppressing activity despite robust protein expression (FIGS. 3C and 3D). As a further control, SEMA3B was moved from pcDNA3 to the pcDNA3.1 vector, and the same degree of suppression of colony formation was observed. The inventors also tested the growth suppressive effect of SEMA3F and found the number of colonies after transfection with SEMA3F was only slightly different (70±17%) than the vector control (FIGS. 3C and 3D). The numbers of colonies were also reduced after transfection with SEMA3B into many other NSCLC lines while little reduction was found in NSCLC line NCI-H23 (Table 4). The growth suppressive effect was seen in lung cancer lines both expressing and not expressing NP2, and in two lung cancers (H2009 and H358) expressing endogenous mRNA for SEMA3B (Table 4). In the case of H358, the expressed SEMA3B mRNA contains a D397H mutation which, as shown above, has very reduced growth suppressing activity.

TABLE 4

G418 resistant colony formation after transfection of a SEMA3B-neo expression plasmid into lung cancer cell lines with various SEMA3B, NP1 and NP2 expression patterns.

| NCI Lung Cancer Cell Lines | Expression of G418 Resistant Colony Formation* | | | |
|---|---|---|---|---|
| | SEMA3B | Npn1 | Npn2 | (% of vector control transfections) |
| H23(NSCLC) | − | + | − | 71 ± 5 |
| H1299(NSCLC) | − | + | − | 10 ± 1 |
| H2227(SCLC) | − | + | + | 10 ± 4 |
| H661(NSCLC) | − | + | + | 4 ± 4 |
| H322(NSCLC) | − | + | − | 3 ± 1 |
| H2009(NSCLC) | ++++ | + | + | 1 ± 1 |
| H358(NSCLC) | ++ | + | + | 0 ± 0 |

*Values are the mean ± SD of 3 separate studies each calculated from counting colonies on triplicate plates. In each case the pcDNA3.1 (neo) vector control transfected number of G418 resistant colonies was set at 100%. SEMA3B expression from Sekido (1996). Note H358 carries a D397H SEMA3B mutation.

Figure 4A:
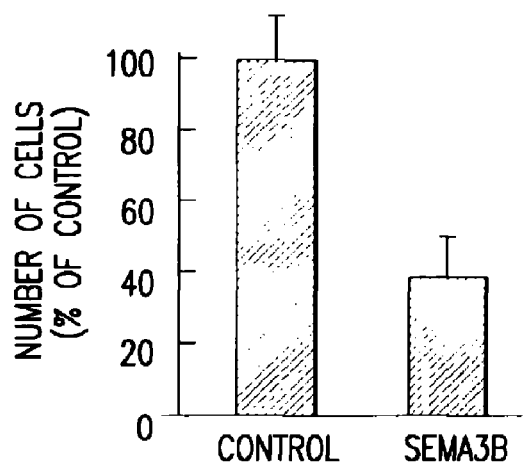
FIGS. 4A-4D—SEMA3B transfection induces apoptosis in H1299 NSCLC cells.
Figure 4C:
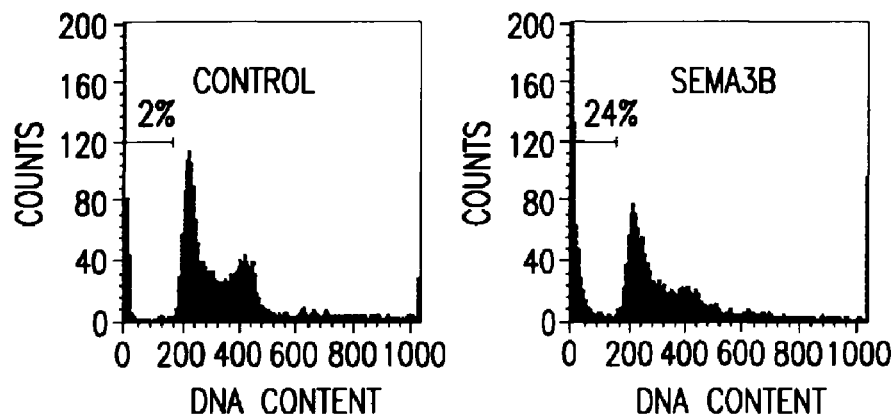
Figure 4D:
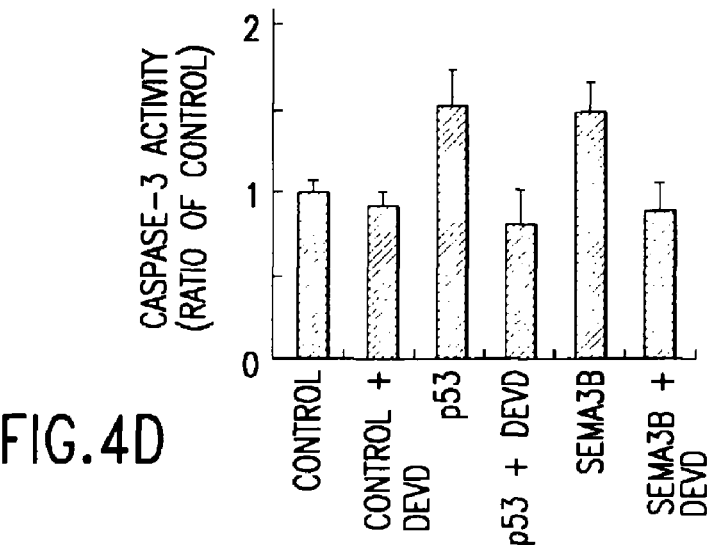
Figure 4B:
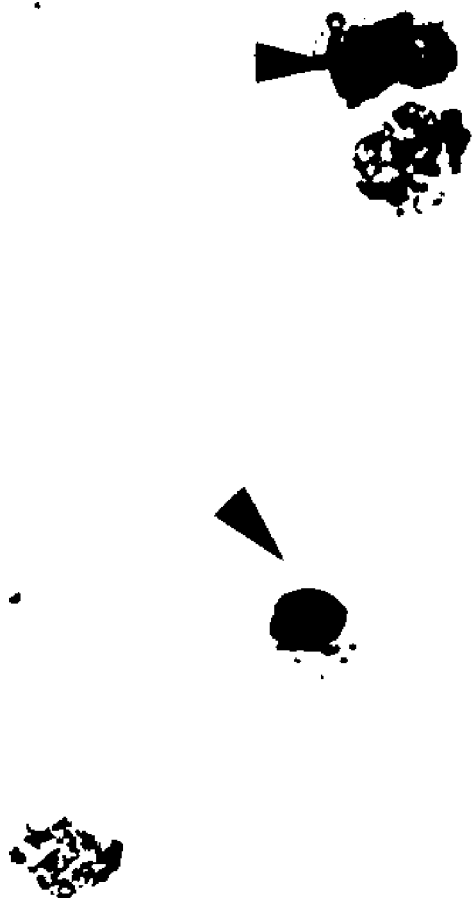

Induction of Apoptosis by Exogenous Expression of SEMA3B. When the wild-type SEMA3B expression plasmid was transfected into H1299 cells, the number of surviving cells was decreased at 48 hr after transfection compared to the control plasmid (FIG. 4A). The amount of this decrease was impressive because the transfection efficiency for the overall population was ~30%. Thus, it is likely a "bystander" effect may be active, potentially mediated by secretion of SEMA3B from transfected cells (see below). This decrease in tumor cell number was associated with appearance of TUNEL positive cells (FIG. 4B), and a 10-fold increase (2 to 24%) of cells with sub-G1 content DNA (FIG. 4C) compared to the control vector, indicating that growth suppression by SEMA3B was due to induction of apoptosis. Transfection of the mutant SEMA3B constructs did not result in apoptosis detected by TUNEL assay (not shown). The inventors did not use an epitope-tagged version of SEMA3B in these studies because other studies showed that a SEMA3B C-terminal FLAG tagged construct was inactive in tumor growth suppression despite conferring similar levels of SEMA2B protein on the transfected. The caspase-3 activity was significantly increased (P<0.05) after wild-type p53 and SEMA3B transfection, and the activity was blocked in both cases by caspase-3 inhibitor DEVD-fmk indicating caspase involvement in SEMA3B induced apoptosis (FIG. 4D).

Figure 5A:
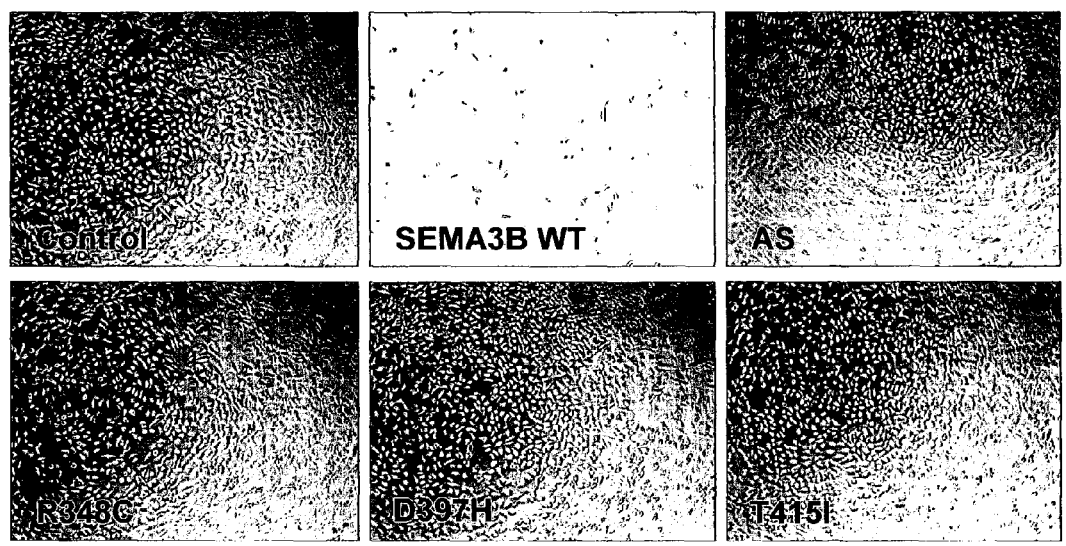
FIGS. 5A-5C—The effect of COS-7 condition medium transfected with SEMA3B expression plasmids on H1299 NSCLC cells.

Growth Suppression by the Conditioned Medium from COS-7 Cells Transfected with SEMA3B. Since SEMA3B is a secreted protein, and lung cancers express NP receptors, the inventors analyzed the effect of conditioned medium harvested from COS-7 cells transfected with SEMA3B on H1299 lung cancer cells. The growth rate of H1299 cells treated with conditioned medium from COS-7 cells transfected with SEMA3B, was reduced compared to conditioned medium vector control transfected COS-7 cells, or conditioned medium harvested after transfection with SEMA3B-Antisense, or mutant SEMA3B constructs (FIG. 5). This lung cancer growth suppressing effect was not found in conditioned medium from SEMA3F transfected COS-7 cells. To confirm the growth suppressive effect of SEMA3B transfected CO S-7 conditioned medium, this assay was performed in several other lung cancer cell lines which have various expression patterns of SEMA3B, NP1 and NP2 and growth inhibition of 30-60% was seen compared to vector control transfected COS-7 cell conditioned medium (Table 5). By contrast, the growth rate of normal human bronchial epithelial cells (NHBE) treated with SEMA3B COS-7 conditioned medium was not significantly different from treatment with vector control transfected COS-7 control medium (Table 5). It should be noted that while NSCLC NCI-H23 colony formation was resistant to transfection induced expression of SEMA3B, this tumor line did show growth inhibition to SEMA3B COS-7 cell condition medium (Table 5).

TABLE 5

Lung cancer cell line growth after exposure to conditioned medium from COS-7 cells transfected with SEMA3B.

| NCI Lung Cancer Cell Lines | Growth Inhibition* |
| --- | --- |
| H1299 | 90 ± 3 |
| H358 | 62 ± 10 |
| H661 | 56 ± 13 |
| H23 | 55 ± 12 |
| H322 | 37 ± 16 |
| H2009 | 36 ± 12 |
| H2227 | 31 ± 6 |
| NHBE | 11 ± 10 |

Figure 5B:
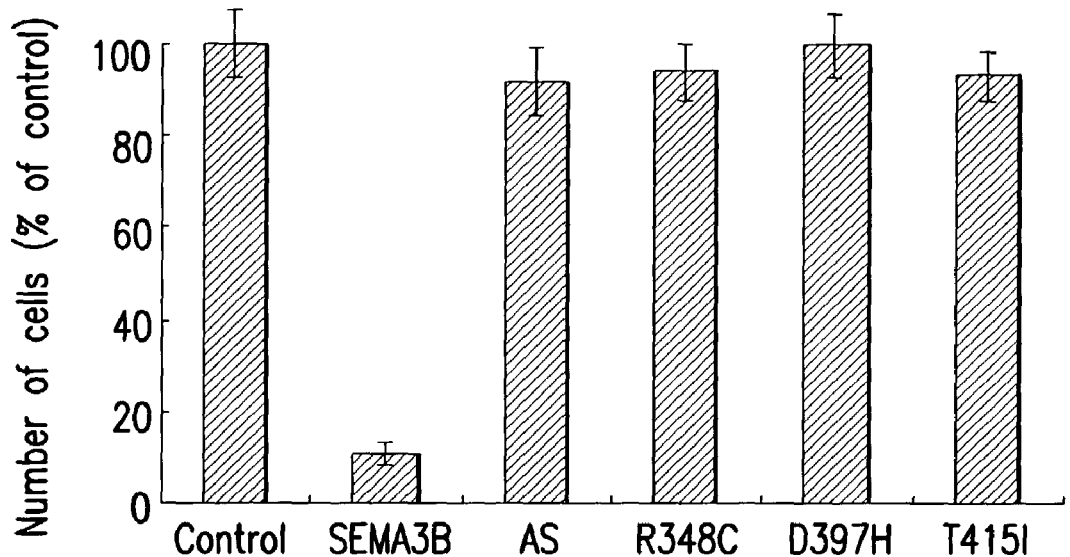
Figure 5C:
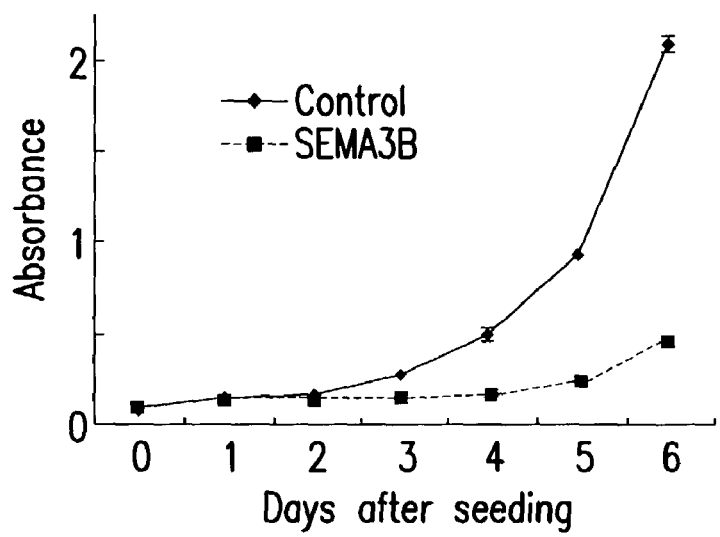

*The studies were performed as described in the legend to FIG. 5B with cell counts performed at day 4. The values are the mean ± SD of 3 separate studies with triplicate wells for cell counting in each study. Vector control transfected COS-7 cell condition medium was applied to the replicate cell cultures and cell numbers at day 4 were set as showing 0% growth inhibition. NHBE, normal human bronchial/tracheal epithelial cell cultures (Clonetics).

Figure 6:
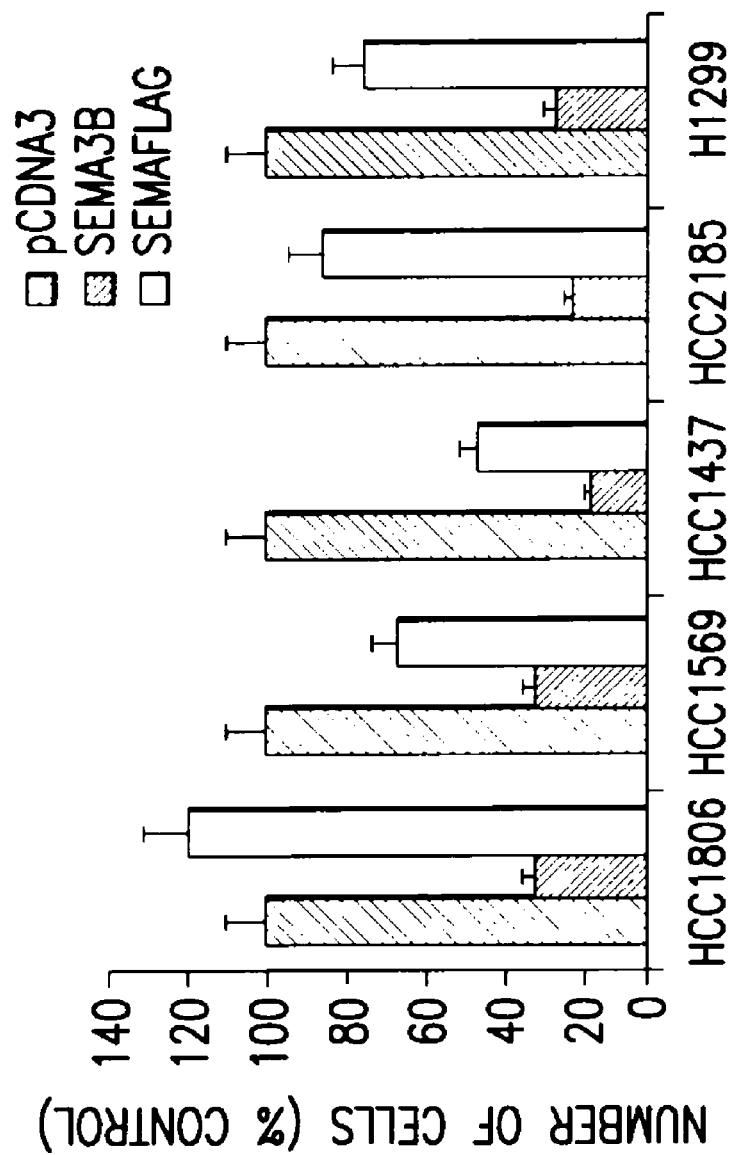
FIG. 6—COS7 conditioned media assay. HCC1806, HCC1569, HCC1437 and HCC2185 are breast cancer cell lines. COS7 cells were transfected with $pcDNA_3$, pSEMA3B and pSEMA3B-Flag. After 24 hr breast cancer cells were incubated with various COS7 conditioned media for 4-5 days and cell numbers were determined. Note the decrease in cell growth with tumor cells treated with SEMA3B conditioned medium compared to empty vector or the SEMA3B-Flag construct conditioned medium. Previous studies had shown that adding the Flag tag caused a loss in SEMA3B growth suppressing activity (Tomizawa et al., 2001).

Breast cancer cells have their growth inhibited by SEMA3B-conditioned media. Breast cancer is the second leading cause of death in women in the United States. Early detection of breast cancer has become an important link to increased survival and this detection is related to the declining mortality of breast cancer in the Western World. Chromosome 3p21.3 allele loss is observed in breast cancer and this allele loss indicates the presence of one or more tumor suppressor genes in this chromosomal region for breast cancer. As discussed above, SEMA3B is part of the 3p21.3 region where tumor suppressor genes can undergo promoter methylation and deletion. Studies were conducted using COS7 cells transfected with SEMA3B, with conditioned medium containing secreted SEMA3B collected after 48 hr. This material was then used to study the effect of SEMA3B on the growth of breast cancer cells (FIG. 6). SEMA3B-Flag (which the inventors have shown has lost considerable activity) and empty vector were used as controls for these studies. The inventors observed a 70-85% decreased in breast cancer cell growth in the presence of SEMA3B-conditioned COS7 media for different breast cancer cell lines (HCC1806, HCC1569, HCC1437 and HCC2185). H1299 lung cancer cells were used as a positive control for these studies. The breast cancer cells showed similar decrease in growth with the SEMA3B-conditioned media compared to H1299 cells, while SEMA3BFLAG media was much less active.

Figure 7:
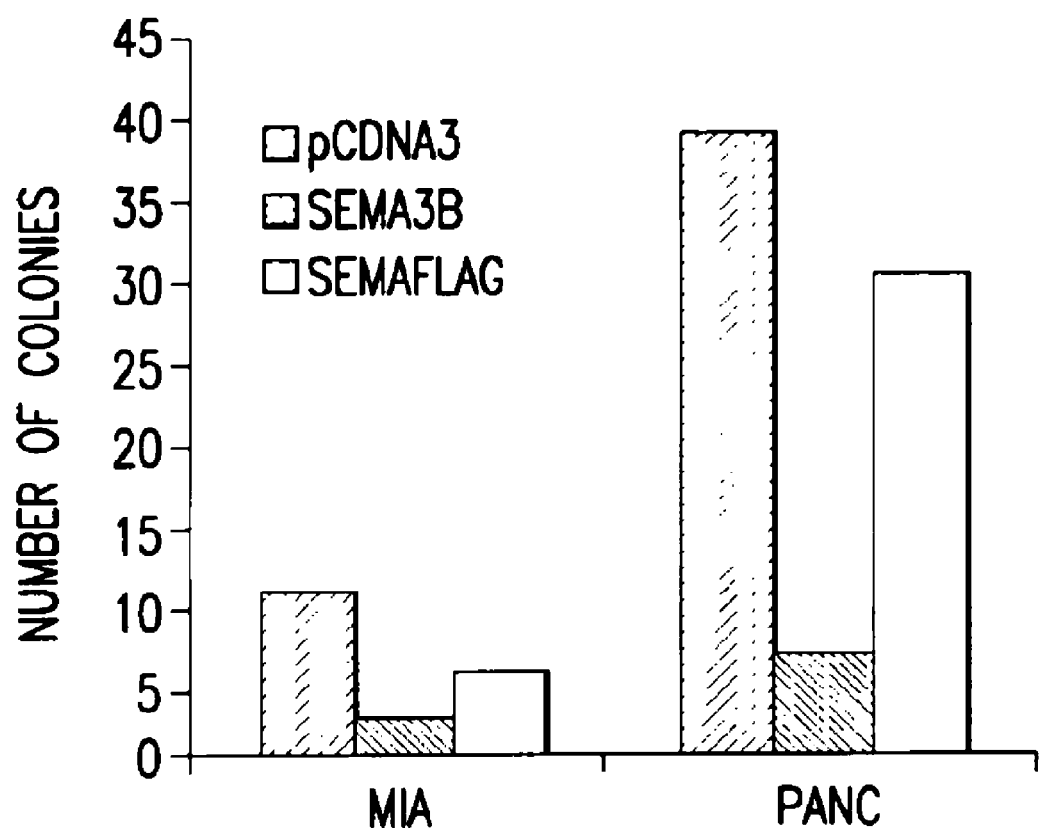
FIG. 7—Liquid colony formation assays. MIA and PANC are pancreatic cancer cell lines. Cells were transfected with pcDNA$_3$, pSEMA3B and pSEMA3B-Flag. After 48 hr pancreatic cancer cells were counted and re-seeded and selected with G418 for 14-21 days. Note the decrease in colony formation with tumor cells transfected with SEMA3B compared to empty vector or the SEMA3B-Flag vector.

Pancreatic cancer cell growth is inhibited by SEMA3B-conditioned media. Cancer of the pancreas is the fifth leading cause of cancer death in the United States. This year approximately 28,000 Americans will die from cancer of the pancreas. The disease is not only common, but it is also extremely difficult to treat. Cancer of the pancreas has been called "the challenge of the twenty-first century." Pancreatic endocrine tumors arise from neuroendocrine cells in and around the pancreas. Many of these tumors have deletions in the 3p14.2-3p21 (Nikiforova, 1999). A liquid colony formation assay was performed by transfecting cells with SEMA3B and SEMA3B-Flag as a negative control. Colonies were counted after 14 days of seeding. Data in pancreatic cancer cells showed that SEMA3B decreases the number of colonies (FIG. 7).

SEMA3B and vascular endothelial growth factor 165 (VEGF165) extert antagonistic effects on the survival and apoptosis of non-small cell lung cancer cells. Both SEMA3B and SEMA3F mediate their activities by binding to neuropilin-1 and -2 (NP-1 and NP-2). The NP-1 and NP-2 receptors also bind angiogenic factors of the VEGF family, such as VEGF165 and P1GF. The NP-1 and NP-2 receptors are expressed in a variety of cells, including breast, lung and prostate carcinomas, all of which are known to express a substantial amount of VEGF165. Recent research has shown an inhibitory effect by SEMA3A in the motility, survival and proliferation of endothelial cells (Miao, 1999; Bagnard, 2001). However, VEGF165 abolishes the effect induced by SEMA3A, suggesting a competition between VEGF165 and SEMA3A for NPs.

Figure 8:
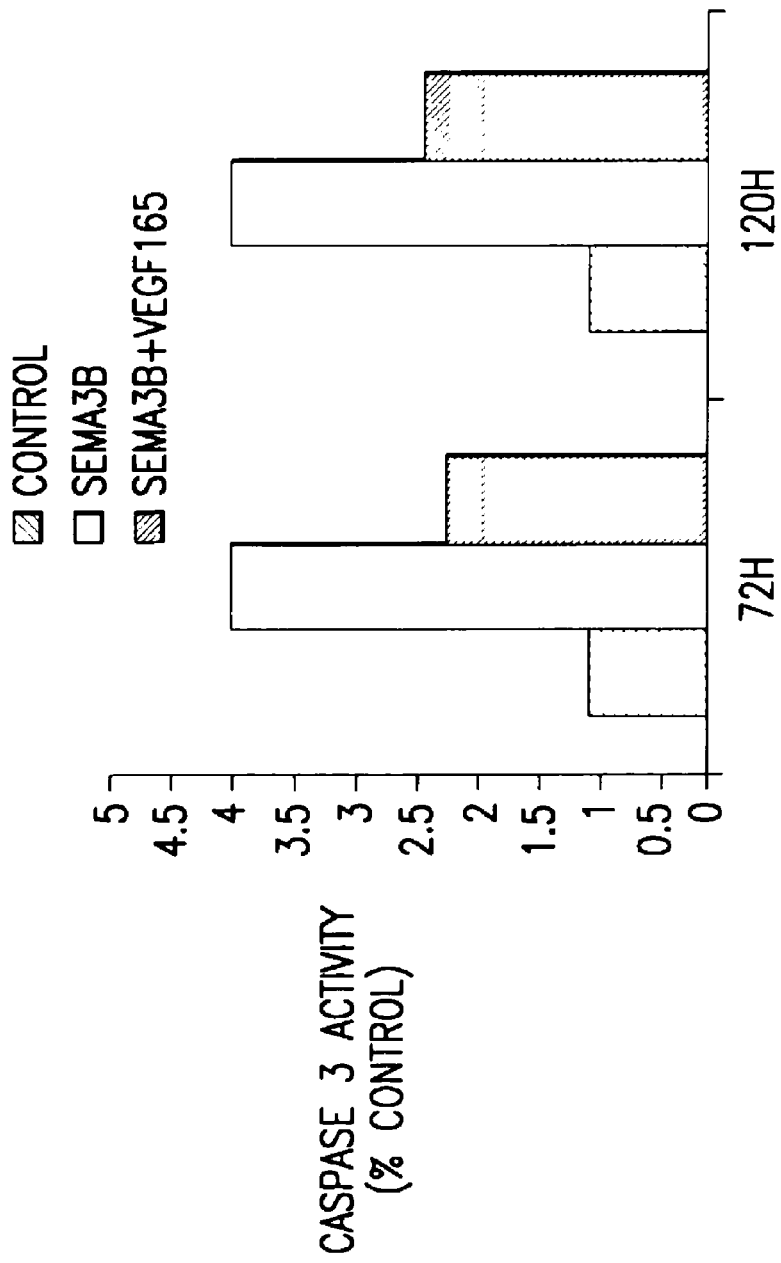
FIG. 8—Apoptosis assays in lung cancer NCI-H1299 cells. A. Sema3B showed an increase in caspase 3 activity that is decrease by 50% when co treatment with VEGF165. Nuclear staining with AROR/ETBR showed a 75% in death apoptotic cells when treated with SEMA3B and only 8% in the presence of VEGF165.
Figure 9:
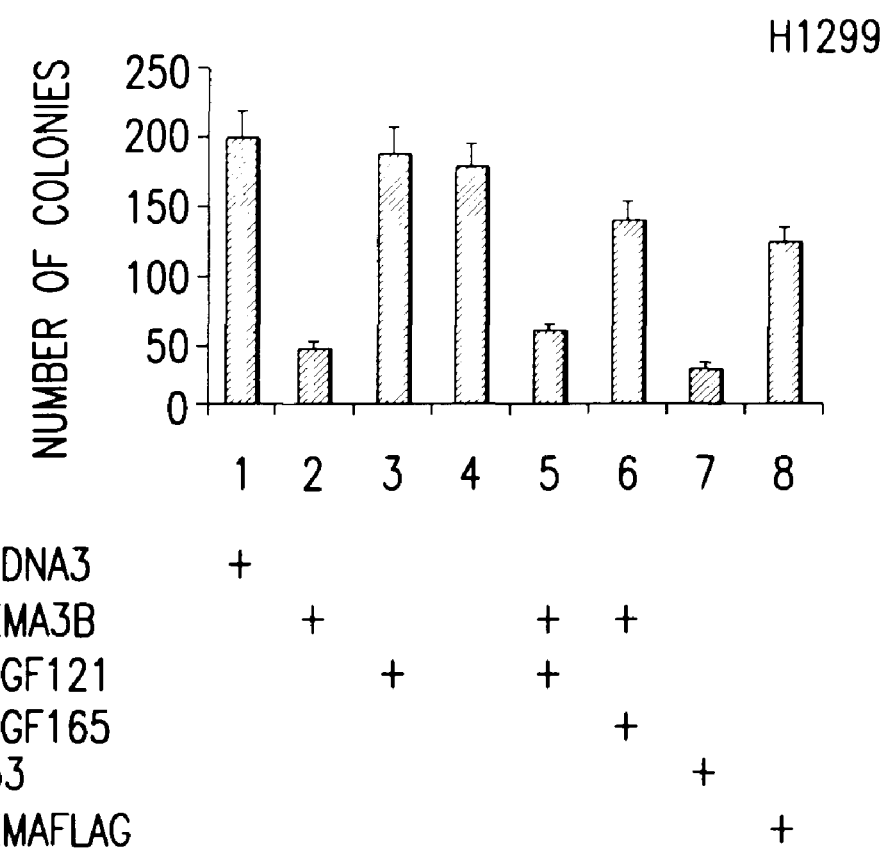
FIG. 9—Colony formation assay in NCI-H1299 cells. Cells were transfected with pcDNA$_3$, pSEMA3B, VEGF165, VEGF121, p53, pSEMA3B-Flag, or various combinations of these vectors. After 48 hours cancer cells were counted and viable cells re-seeded and selected with G418 for 14-21 days when colonies were counted. (Lanes 1, pcDNA3; 2, SEMA3B; 3, VEGF121; 4, mock transfection; 5, SEMA3B and VEGF121; 6, SEMA3B and VEGF165; 7, p53; 8, SEMA3BFLAG. Note the decrease in colony formation with tumor cells transfected SEMA3B is blocked by VEGF165 and not VEGF121.
Figure 10:
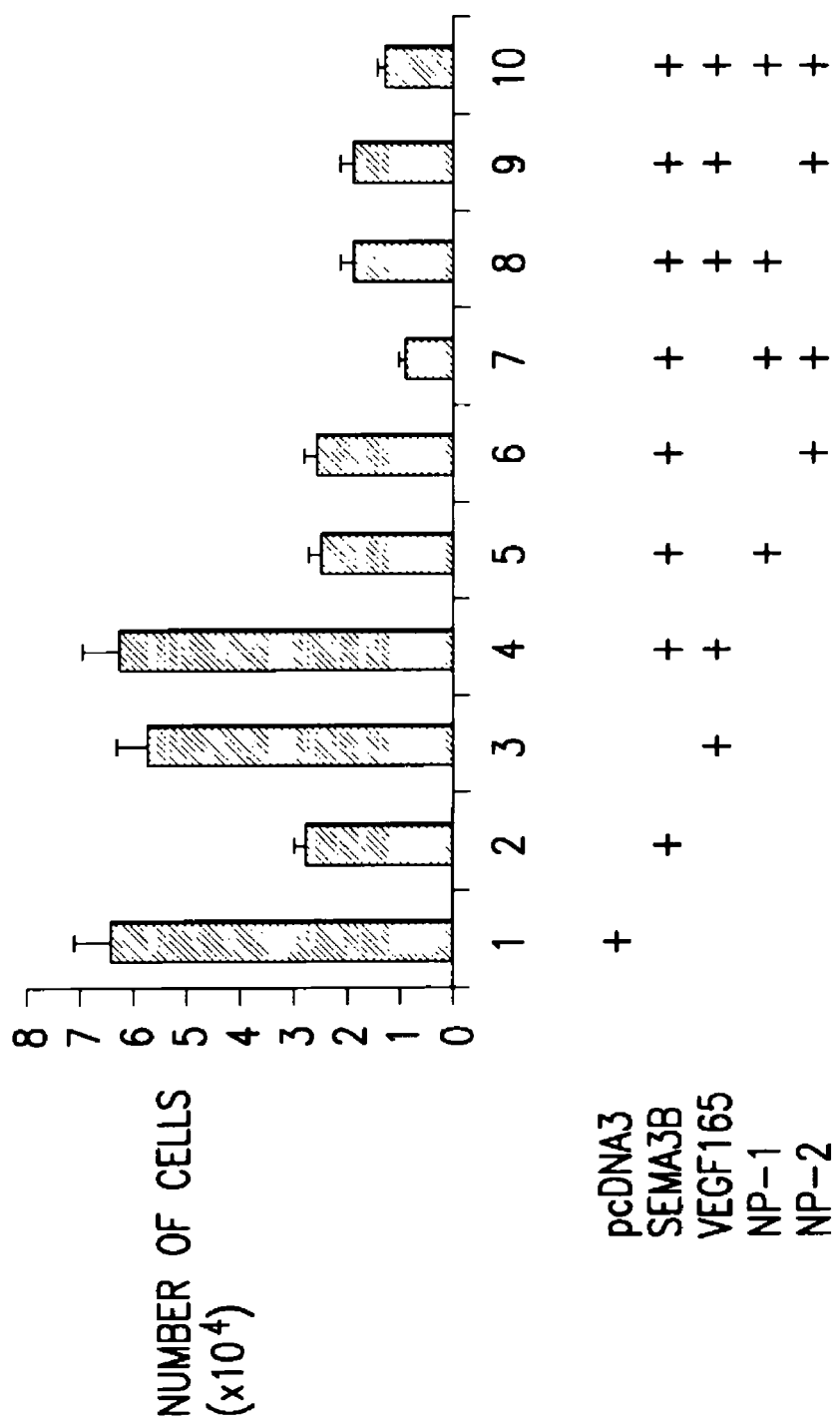
FIG. 10—VEGF165 abolishment of SEMA3B growth suppression was block by anti-NP-1 and NP-2. Cells were treated simultaneous with the different ligands (SEMA3B and VEGF165) and anti-NP-1 and NP-2. Cells were counted a week later.

Recently, the inventors and others have described tumor suppressor activity of SEMA3B in non-small cell lung cancer (NSCLC) and ovarian cancer cells (Tomizawa, 2001; Tse, 2002). The inventors found that transfection of various lung cancer cell lines with the plasmid encoding SEMA3B causes caspase-3-dependent apoptosis and severely restricts proliferation of these cells as well as their clonogenic potential. SEMA3B-treated cells, but not control-treated cells, showed an increase in active caspase-3 and visible chromatin condensation using acridine orange and ethidium bromide staining (AROR/ETBR) (FIG. 8). The inventors found that VEGF165, which has been previously shown to act as a survival factor for endothelial and breast cancer cells, abolished or significantly decreased the apoptotic effect of SEMA3B. Cotransfection of VEGF165 with SEMA3B, reversed SEMA3B anti-proliferative activity by more than 50% in colony formation assays (FIG. 9). In contrast to VEGF165, the VEGF isoform VEGF121, a VEGF variant that lacks binding to heparin or NP-1 and NP-2 receptors, had no effect on SEMA3B growth suppressing activities (FIG. 9). The inventors were able to show these effects were occurring through neuropilin receptors as anti-NP-1 and NP-2 antibodies blocked the inhibitory effect of SEMA3B as well as the survival effect (anti-SEMA3B effect) of VEGF165 (FIG. 10). These results lead to the hypothesis that VEGF165 acts as an autocrine survival factor for lung cancer and SEMA3B mediates its tumor suppressing effects, at least in part, by blocking this VEGF autocrine activity.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

XI. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,683,195
U.S. Pat. No. 4,683,202
U.S. Pat. No. 4,800,159
U.S. Pat. No. 4,816,567
U.S. Pat. No. 4,867,973
U.S. Pat. No. 4,946,773
U.S. Pat. No. 5,252,479
U.S. Pat. No. 5,279,721
U.S. Pat. No. 5,565,332
U.S. Pat. No. 5,578,832
U.S. Pat. No. 5,672,344
U.S. Pat. No. 5,837,832
U.S. Pat. No. 5,837,860
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,483
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,770
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,242
U.S. Pat. No. 5,861,244
U.S. Pat. No. 5,863,732
U.S. Pat. No. 5,863,753
U.S. Pat. No. 5,866,331
U.S. Pat. No. 5,866,337
U.S. Pat. No. 5,866,366
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,916,776
U.S. Pat. No. 5,919,626
U.S. Pat. No. 5,919,630
U.S. Pat. No. 5,922,574
U.S. Pat. No. 5,925,517
U.S. Pat. No. 5,925,525
U.S. Pat. No. 5,925,565
U.S. Pat. No. 5,928,862
U.S. Pat. No. 5,928,869
U.S. Pat. No. 5,928,870
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,819
U.S. Pat. No. 5,935,825
U.S. Pat. No. 5,939,291
U.S. Pat. No. 5,942,391
U.S. Pat. No. 5,994,136
U.S. Pat. No. 6,013,516
Abbondanzo, "Paraffin immunohistochemistry as an adjunct to hematopathology," *Ann Diagn Pathol*, 3(5):318-327, 1999.
Allred, Bustamante, Daniel, Gaskill, Cruz Jr., "Immunocytochemical analysis of estrogen receptors in human breast carcinomas. Evaluation of 130 cases and review of the literature regarding concordance with biochemical assay and clinical relevance," *Arch Surg*, 125(1):107-13, 1990.
Antibodies: A Laboratory Manual, Cold Spring Harbor Laboratory, Cold Spring Harbor Press, Cold Spring Harbor, N.Y., 1988.
Arap et al., *Cancer Res.*, 55(6):1351-1354, 1995.
Ausubel et al., In: *Current Protocols in Molecular Biology*, John, Wiley and Sons, Inc, New York, 1994.
Bachelder et al., *Cancer Res.* 61, 5736-40, 2001.
Bagnard, *J. Neurosci.* 21(10):3332-4121, 2001.
Bahnemann et al. *Abs. Pap. ACS*, 180:5. 1980.

Baichwal and Sugden, In: *Gene Transfer*, Kucherlapati (ed.), New York, Plenum Press, 117-148, 1986.
Bakhshi et al., *Cell*, 41(3):899-906, 1985.
Batterson and Roizman, *J. Virol.*, 46(2):371-377, 1983.
Baylin et al., *Adv. Cancer Res.* 72:141-196, 1998.
Behar et al., *Proc. Natl. Acad. Sci. USA*, 96:13501-13505, 1999.
Bellus, *J. Macromol. Sci. Pure Appl. Chem.*, A31(1):1355-1376, 1994.
Benvenisty and Neshif, *Proc. Natl. Acad. Sci. USA*, 83(24):9551-9555, 1986.
Berns and Bohensky, *Adv. Virus Res.*, 32:243-306, 1987.
Berns and Giraud, *Curr. Top Microbiol. Immunol.*, 218:1-23, 1996.
Berns, *Microbiol. Rev.*, 54(3):316-329, 1990.
Blomer et al., *J. Virol.*, 71(9):6641-6649, 1997.
Brambilla et al., *Am. J. Pathol.* 156, 939-950, 2000.
Brown et al., *Immunol Ser,* 53:69-82, 1990.
Burbee et al., *J. Natl. Cancer Inst.* 93, 691-699, 2001.
Caldas et al., *Nat. Genet.*, 8(1):27-32, 1994.
Campbell, In: *Monoclonal Antibody Technology, Laboratory Techniques in Biochemistry and Molecular Biology*, Burden and Von Knippenberg (Eds.), Elseview, Amsterdam, 13:71-74; 75-83, 1984.
Chandler et al., *Proc. Natl. Acad. Sci. USA,* 94(8):3596-3601, 1997.
Chen et al., *Oncogene.* 8:2159-2166, 1993.
Cheng, Jhanwar, Klein, Bell, Lee, Altomare, Nobori, Olopade, Buckler, Testa Jr., "p16 alterations and deletion mapping of 9p21-p22 in malignant mesothelioma," *Cancer Res.*, 54(21):5547-5551, 1994.
Christensen et al., *Cancer Res.*, 58:1238-1244, 1998.
Clark et al., *Nucleic Acids Res.*, 22:2990-2997, 1994.
Cleary and Sklar, *Proc. Natl. Acad. Sci. USA*, (21):7439-7443, 1985.
Cleary et al., *J. Exp. Med.*, 164(1):315-320, 1986.
Coffin, In: *Virology*, Fields et al., eds., Raven Press, NY, 1437-1500, 1990.
Comoglio et al., *Exp. Cell Res.*, 253, 88-99, 1999.
Dammann et al., *Nat. Genet.*, 25, 315-319, 2000.
De Jager et al., *Semin. Nucl. Med.*, 23(2):165-179, 1993.
DeLuca et al., *J. Virol.*, 56(2):558-570, 1985.
Doolittle and Ben-Zeev, *Methods Mol. Biol.*, 109:215-237, 1999.
Dubensky et al., *Proc. Natl. Acad. Sci. USA,* 81:7529-7533, 1984.
Elroy-Stein et al., *Proc. Natl. Acad. Sci. USA,* 86(16):6126-30, 1989.
Fodor et al., *Biochemistry,* 30(33):8102-8108, 1991.
Gagliardini and Fankhauser, *Mol. Cell. Neurosci.*, 14, 301-316, 1999.
Gagnon et al., *Proc. Natl. Acad. Sci. USA,* 97:2573-2578, 2000.
GB Application 2 202 328
Ghosh and Bachhawat, In: *Liver Diseases, Targeted Diagnosis and Therapy Using Specific Receptors and Ligands*. Wu et al., eds., Marcel Dekker, New York, 87-104, 1991.
Giger et al., *Neuron.*, 21:1079-1092, 1998.
Glorioso et al., *Mol. Biotechnol.*, 4(1):87-99, 1995.
Goding, In: *Monoclonal Antibodies: Principles and Practice,* 2d ed., Academic Press, Orlando, Fla., pp. 60-61, and 71-74, 1986.
Gomez-Foix et al., *J. Biol. Chem.*, 267:25129-25134, 1992.
Graham and Prevec, *Biotechnology,* 20:363-390, 1992.
Graham et al., *J. Gen. Virol,* 36:59-72, 1977.
Grunhaus et al., *Seminar in Virology,* 200(2):535-546, 1992.
Gu, *J. Biol. Chem.* 277, 2002.
Gulbis and Galand, *Hum. Pathol.*, 24(12):1271-85, 1993.
Hacia et al., *Nature Genet.*, 14:441-449, 1996.
Herz and Gerard, *Proc. Natl. Acad. Sci. USA*, 90:2812-2816, 1993.
Holland and Holland, *J. Biol. Chem.*, 255(6):2596-605, 1980.
Hollstein et al., *Science*, 253(5015):49-53, 1991.
Holmstrom et al., *Anal. Biochem.* 209:278-283, 1993.
Hones and Roizman, *J. Virol.*, 16(5):1308-1326, 1975.
Hones and Roizman, *J. Virol.*, 14(1):8-19, 1974.
Hussussian et al., *Nat. Genet.*, 8(1):15-21, 1994.
Innis et al., *Proc. Natl. Acad. Sci. USA,* 85(24):9436-9440, 1988.
Inouye and Inouye, *Nucleic Acids Res.*, 13: 3101-3109, 1985.
Ito et al., *Mech. Dev.,* 97, 35-45, 2000.
Kamb et al., *Nat. Genet.*, 8(1):23-2, 1994.
Kaneda et al., *Science,* 243:375-378, 1989.
Kato et al., *J. Biol. Chem.*, 266:3361-3364, 1991.
Kearns et al, *Gene Ther.*, 3(9):748-755, 1996.
Kerr et al., *Br. J. Cancer,* 26(4):239-257, 1972.
Kotin and Berns, *Virology,* 170(2):460-467, 1989.
Kotin et al., *Genomics,* 10(3):831-4, 1991.
Kotin et al., *Proc. Natl. Acad. Sci. USA,* 87(6):2211-2215, 1990.
Larsson and Litwin, *Dev. Biol. Standard.*, 66:385-390, 1987.
Le Gal La Salle et al., *Science,* 259:988-990, 1993.
Levrero et al, *Gene,* 101: 195-202, 1991.
Macejak and Sarnow, *Nature,* 353:90-94, 1991.
Maniatis, et al., In: *Molecular Cloning*, A Laboratory Manual, Cold Spring Harbor Press, Cold Spring Harbor, N.Y., 1989.
Mann et al., *Cell,* 33:153-159, 1983.
Martin-Satue and Blanco, *J. Surg. Oncol.,* 72, 18-23, 1999.
Miao, Lee, Lin, Soker, Klagsbrun, *Faseb. J.*, 14:2532-2539, 2000.
Miao et al., *J. Cell Biol.,* 146:233-242, 1999.
Mizrahi, *Process Biochem.,* 9-12, 1983.
Mizukami et al., *Virology,* 217(1):124-130, 1996.
Nakamura et al., *J. Neurobiol.*, 44:219-29, 2000.
Nakamura et al., In: *Handbook of Experimental Immunology* (4$^{th}$ Ed.), Weir, Herzenberg, Blackwell, Herzenberg, (eds). 1:27, Blackwell Scientific Publ., Oxford, 1987.
Naldini et al., *Science,* 272(5259):263-267, 1996.
Newton et al., *Nucl. Acids Res.,* 21:1155-1162, 1993.
Nicolas and Rubinstein, In: *Vectors: A survey of molecular cloning vectors and their uses*, Rodriguez and Denhardt, eds., Stoneham: Butterworth, 494-513, 1988.
Nicolau et al., *Methods Enzymol.*, 149:157-176, 1987.
Nikiforova, *Clin. Endocrinol.* (Oxf), 51, 1999.
Nilsson and Mosbach, *Dev. Biol. Standard.,* 66:183-193, 1987.
Nobori et al., *Nature,* 368(6473):753-756, 1994.
Okamoto et al., *Proc. Natl. Acad. Sci. USA,* 1(23):11045-11049, 1994.
Orlow et al., *Cancer Res.*, 54(11):2848-2851, 1994.
Ostrove et al., *Virology,* 113(2):521-33, 1981.
Paskind et al., *Virology,* 67:242-248, 1975.
PCT Application PCT/US00/14350
PCT Application PCT/US89/01025
PCT Application PCT/US99/05781
Pease et al., *Proc. Natl. Acad. Sci. USA,* 91:5022-5026, 1994.
Pelletier and Sonenberg, *Dev. Biol. Standard.,* 66:3-12, 1985.
Phelps et al., *J. Cell Biochem.*, 24:32-91, 1996.
Phillips et al., In: *Large Scale Mammalian Cell Culture* (Feder and Tolbert eds.), Academic Press, Orlando, Fla., U.S.A., 1985.
Ponnazhagan et al., *J. Gen. Virol.*, 77(Pt6):1111-1122, 1996.
Ponnazhagan et al., *J. Virol.*, 71(4):3098-3104, 1997.

Post et al., *Cell,* 24(2):555-565, 1981.
Ragot et al., *Nature,* 361:647-650, 1993.
Raper, *Curr. Opin. Neurobiol.,* 10, 88-94, 2000.
Rasmussen et al., *Anal. Biochem.,* 198:138-142, 1991.
Remington's Pharmaceutical Sciences, 18th Ed. Mack Printing Company, pp. 1289-1329, 1990.
Rich et al., *Hum. Gene Ther.,* 4:461-476, 1993.
Ridgeway, In: Vectors: *A survey of molecular cloning vectors and their uses*, Rodriguez and Denhardt (eds.), Stoneham: Butterworth, 467-492, 1988.
Rosenfeld et al., *Science,* 252:431-434, 1991.
Rosenfeld et al., *Cell,* 68:143-155, 1992.
Roux et al., *Proc. Natl. Acad. Sci. USA,* 86:9079-9083, 1989.
Roy et al., *Development,* 127:755-67, 2000.
Running et al., *BioTechniques,* 8:276-277, 1990.
Sakamoto et al, *Proc. Natl. Acad. Sci. USA,* 83:3997-4001, 1986.
Sambrook et. al., In: *Molecular Cloning: A Laboratory Manual,* 2d Ed., Cold Spring Harbor Laboratory Press, Cold Spring Harbor, N.Y., 2000.
Samulski et al., *EMBO J,* 10:3941-3950, 1991.
Sekido et al., *Proc. Natl. Acad. Sci. USA,* 93:4120-4125, 1996.
Serrano et al., *Science,* 267(5195):249-252, 1995.
Serrano et al, *Nature,* 366:704-707, 1993.
Shirvan et al, *J. Neurochem.,* 73:961-71, 1999.
Shoemaker et al., *Nature Genetics,* 14:450-456, 1996.
Smith and Moss, *Gene,* 25(1):21-8, 1983.
Stratford-Perricaudet and Perricaudet, In: *Human Gene Transfer,* Eds, Cohen-Haguenauer and Boiron, John Libbey Eurotext, France, pp. 51-61, 1991.
Stratford-Perricaudet et al., *Hum. Gene. Ther.,* 1:241-256, 1990.
Tamagnone and Comoglio, *Trends Cell. Biol.,* 10, 377-83, 2000.
Tamagnone et al., *Cell,* 99:71-80, 1999.
Temin, In: *Gene Transfer,* Kucherlapati (ed.), New York: Plenum Press, pp. 149-188, 1986.
Todd et al., *Oncogen,* 13, 2387-96, 1996.
Tomizawa et al., *Proc. Natl. Acad. Sci. USA,* 98:12954, 2001.
Tse, *Cancer Res.,* 62:542, 2002.
Tsujimoto and Croce, *Proc. Natl. Acad. Sci. USA,* 83(14):5214-5218, 1986.
Tsujimoto et al., *Science,* 228(4706):1440-1443, 1985.
van Wezel, *Nature,* 216:64-65, 1967.
Wang et al., In: *Animal Cell Technology: Basic & Applied Aspects,* S. Kaminogawa et al, (eds), 5:463-469, Kluwer Academic Publishers, Netherlands, 1993.
Wang et al., *Proc. Jap. Soc. Anim. Cell Tech.,* 1994.
Wang et al., *J. Reconstruc. Microsurg.,* 9(1):39-48, 1992.
Weinberg, *Science,* 254(5035):1138-1146, 1991.
Wistuba et al., *Cancer Res.,* 60:1949-60, 2000.
WO 84/03564
WO 90/07641
WO 94/17178
Wong et al., *Gene,* 10:87-94, 1980.
Wu and Wu, *Adv. Drug Delivery Rev.,* 12:159-167, 1993.
Xiang et al., *Genomics* 32, 39-48, 1996.
Yamada et al., *Proc. Natl. Acad. Sci. USA,* 94:14713-14718, 1997.
Zufferey et al., *Nat. Biotechnol.,* 15(9):871-875, 1997.

What is claimed is:

1. A method for inhibiting the proliferation of or killing of a lung cancer cell comprising contacting said lung cancer cell with a semaphorin3B (SEMA3B) polypeptide comprising the sequence of SEQ ID NO:1, wherein said polypeptide is produced from a viral expression construct comprising a nucleic acid segment encoding SEMA3B under the control of promoter heterologous to the nucleic acid segment encoding SEMA3B, wherein said viral expression construct has been introduced into said lung cancer cell, and wherein expression of SEMA3B inhibits the proliferation of or kills said lung cancer cell.

2. The method of claim 1, wherein said lung cancer cell is killed.

3. The method of claim 2, wherein said lung cancer cell is killed by apoptotic cell death.

4. The method of claim 1, wherein said viral expression construct is selected from the group consisting of adenovirus, retrovirus, adeno-associated virus, herpesvirus, vaccinia virus and polyoma virus.

5. The method of claim 1, wherein said promoter is a constitutive promoter.

6. The method of claim 1, wherein said promoter is an inducible promoter.

7. The method of claim 1, wherein said promoter is a tissue preferential promoter.

8. The method of claim 1, wherein said expression construct further comprises an origin of replication.

9. The method of claim 1, wherein said expression construct further comprises a polyadenylation signal.

10. The method of claim 1, wherein said expression construct further comprises a selectable marker gene.

11. The method of claim 1, further comprising treating said cell with one or more additional anti-proliferative treatments.

* * * * *

UNITED STATES PATENT AND TRADEMARK OFFICE
CERTIFICATE OF CORRECTION

PATENT NO. : 7,781,413 B2
APPLICATION NO. : 10/285351
DATED : August 24, 2010
INVENTOR(S) : John Minna et al.

Page 1 of 1

It is certified that error appears in the above-identified patent and that said Letters Patent is hereby corrected as shown below:

In column 1, lines 8-10, delete paragraph and insert
--This invention was made with government support under grant numbers CA71618 and CA70907 awarded by the National Institutes of Health. The government has certain rights in the invention.--.

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

Page 1 of 1

PATENT NO. : 7,781,413 B2
APPLICATION NO. : 10/285351
DATED : August 24, 2010
INVENTOR(S) : John Minna et al.

It is certified that error appears in the above-identified patent and that said Letters Patent is hereby corrected as shown below:

In title page, item (73) Assignee, line 3, insert
--The Government of the United States of America as represented by the Secretary of the Department of Health and Human Services, Rockville, MD (US)--.

Signed and Sealed this
Fifteenth Day of March, 2011

David J. Kappos
*Director of the United States Patent and Trademark Office*

SEQUENCE LISTING

<160> NUMBER OF SEQ ID NOS: 6

<210> SEQ ID NO 1
<211> LENGTH: 749
<212> TYPE: PRT
<213> ORGANISM: Homo sapiens

<400> SEQUENCE: 1

```
Met Gly Arg Ala Gly Ala Ala Val Ile Pro Gly Leu Ala Leu Leu
 1               5                  10                  15

Trp Ala Val Gly Leu Gly Ser Ala Ala Pro Ser Pro Arg Leu Arg
                20                  25                  30

Leu Ser Phe Gln Glu Leu Gln Ala Trp His Gly Leu Gln Thr Phe Ser
            35                  40                  45

Leu Glu Arg Thr Cys Cys Tyr Gln Ala Leu Leu Val Asp Glu Glu Arg
        50                  55                  60

Gly Arg Leu Phe Val Gly Ala Glu Asn His Val Ala Ser Leu Asn Leu
    65                  70                  75                  80

Asp Asn Ile Ser Lys Arg Ala Lys Lys Leu Ala Trp Pro Ala Pro Val
                    85                  90                  95

Glu Trp Arg Glu Glu Cys Asn Trp Ala Gly Lys Asp Ile Gly Thr Glu
                100                 105                 110

Cys Met Asn Phe Val Lys Leu Leu His Ala Tyr Asn Arg Thr His Leu
            115                 120                 125

Leu Ala Cys Gly Thr Gly Ala Phe His Pro Thr Cys Ala Phe Val Glu
        130                 135                 140
```

-continued

```
Val Gly His Arg Ala Glu Glu Pro Val Leu Arg Leu Asp Pro Gly Arg
145                 150                 155                 160

Ile Glu Asp Gly Lys Gly Lys Ser Pro Tyr Asp Pro Arg His Arg Ala
            165                 170                 175

Ala Ser Val Leu Val Gly Glu Glu Leu Tyr Ser Gly Val Ala Ala Asp
        180                 185                 190

Leu Met Gly Arg Asp Phe Thr Ile Phe Arg Ser Leu Gly Gln Arg Pro
            195                 200                 205

Ser Leu Arg Thr Glu Pro His Asp Ser Arg Trp Leu Asn Glu Pro Lys
        210                 215                 220

Phe Val Lys Val Phe Trp Ile Pro Glu Ser Glu Asn Pro Asp Asp Asp
225                 230                 235                 240

Lys Ile Tyr Phe Phe Phe Arg Glu Thr Ala Val Glu Ala Ala Pro Ala
            245                 250                 255

Leu Gly Arg Leu Ser Val Ser Arg Val Gly Gln Ile Cys Arg Asn Asp
        260                 265                 270

Val Gly Gly Gln Arg Ser Leu Val Asn Lys Trp Thr Thr Phe Leu Lys
    275                 280                 285

Ala Arg Leu Val Cys Ser Val Pro Gly Val Glu Gly Asp Thr His Phe
290                 295                 300

Asp Gln Leu Gln Asp Val Phe Leu Leu Ser Ser Arg Asp His Arg Thr
305                 310                 315                 320

Pro Leu Leu Tyr Ala Val Phe Ser Thr Ser Ser Ser Ile Phe Gln Gly
            325                 330                 335

Ser Ala Val Cys Val Tyr Ser Met Asn Asp Val Arg Arg Ala Phe Leu
        340                 345                 350

Gly Pro Phe Ala His Lys Glu Gly Pro Met His Gln Trp Val Ser Tyr
        355                 360                 365

Gln Gly Arg Val Pro Tyr Pro Arg Pro Gly Met Cys Pro Ser Lys Thr
    370                 375                 380

Phe Gly Thr Phe Ser Ser Thr Lys Asp Phe Pro Asp Asp Val Ile Gln
385                 390                 395                 400

Phe Ala Arg Asn His Pro Leu Met Tyr Asn Ser Val Leu Pro Thr Gly
            405                 410                 415

Gly Arg Pro Leu Phe Leu Gln Val Gly Ala Asn Tyr Thr Phe Thr Gln
        420                 425                 430

Ile Ala Ala Asp Arg Val Ala Ala Asp Gly His Tyr Asp Val Leu
        435                 440                 445

Phe Ile Gly Thr Asp Val Gly Thr Val Leu Lys Val Ile Ser Val Pro
450                 455                 460

Lys Gly Ser Arg Pro Ser Ala Glu Gly Leu Leu Leu Glu Glu Leu His
465                 470                 475                 480

Val Phe Glu Asp Ser Ala Ala Val Thr Ser Met Gln Ile Ser Ser Lys
            485                 490                 495

Arg His Gln Leu Tyr Val Ala Ser Arg Ser Ala Val Ala Gln Ile Ala
        500                 505                 510

Leu His Arg Cys Ala Ala His Gly Arg Val Cys Thr Glu Cys Cys Leu
    515                 520                 525

Ala Arg Asp Pro Tyr Cys Ala Trp Asp Gly Val Ala Cys Thr Arg Phe
530                 535                 540

Gln Pro Ser Ala Lys Arg Arg Phe Arg Arg Gln Asp Val Arg Asn Gly
545                 550                 555                 560
```

```
Asp Pro Ser Thr Leu Cys Ser Gly Asp Ser Ser Arg Pro Ala Leu Leu
                565                 570                 575

Glu His Lys Val Phe Gly Val Glu Gly Ser Ser Ala Phe Leu Glu Cys
            580                 585                 590

Glu Pro Arg Ser Leu Gln Ala Arg Val Glu Trp Thr Phe Gln Arg Ala
        595                 600                 605

Gly Val Thr Ala His Thr Gln Val Leu Ala Glu Glu Arg Thr Glu Arg
    610                 615                 620

Thr Ala Arg Gly Leu Leu Leu Arg Arg Leu Arg Arg Asp Ser Gly
625                 630                 635                 640

Val Tyr Leu Cys Ala Ala Val Glu Gln Gly Phe Thr Gln Pro Leu Arg
                645                 650                 655

Arg Leu Ser Leu His Val Leu Ser Ala Thr Gln Ala Glu Arg Leu Ala
            660                 665                 670

Arg Ala Glu Glu Ala Pro Ala Pro Pro Gly Pro Lys Leu Trp
        675                 680                 685

Tyr Arg Asp Phe Leu Gln Leu Val Glu Pro Gly Gly Gly Ser Ala
    690                 695                 700

Asn Ser Leu Arg Met Cys Arg Pro Gln Pro Ala Leu Gln Ser Leu Pro
705                 710                 715                 720

Leu Glu Ser Arg Arg Lys Gly Arg Asn Arg Arg Thr His Ala Pro Glu
                725                 730                 735

Pro Arg Ala Glu Arg Gly Pro Arg Ser Ala Thr His Trp
        740                 745

<210> SEQ ID NO 2
<211> LENGTH: 2919
<212> TYPE: DNA
<213> ORGANISM: Homo sapiens

<400> SEQUENCE: 2
tctgtgattg tggccaggcg gggcaccctc ggaggggagg gttcggaagt ggaatgcgac      60 ccccagcct  ctttcccta  ggggctgtaa  tctgatccct  ggggactccc  ccctagcct   120 cccgccctcg cccctcactgc tgactcctct tccagatcct ggggcagagt ccagggcagc   180
tcaaggctcc tccacacaca cacccgctga accctgagca ccctgagctg ctgagatggg   240
gcgggccggg gctgccgccg tgatcccggg cctggccctg tctgggcag  tggggctggg   300 gagtgccgcc cccagccccc cacgccttcg gctctccttc caagagctcc aggcctggca   360
tggtctccag actttcagcc tggagcgaac ctgctgctac caggccttgc tggtggatga   420
ggagcgtgga cgcctgtttg tgggtgccga gaaccatgtg gcctccctca acctggacaa   480
catcagcaag cgggccaaga agctggcctg gccggcccct gtggaatggc gagaggagtg   540
caactgggca gggaaggaca ttggtactga gtgcatgaac ttcgtgaagt tgctgcatgc   600
ctacaaccgc acccatttgc tggcctgtgg cacgggagcc ttccacccaa cctgtgcctt   660
tgtggaagtg ggccaccggg cagaggagcc cgtcctccgg ctggaccag gaaggataga   720 ggatggcaag gggaagagtc cttatgaccc caggcatcgg gctgcctccg tgctggtggg   780
ggaggagcta tactcagggg tggcagcaga cctcatggga cgagacttta ccatctttcg   840
cagcctaggg caacgtccaa gtctccgaac agagccacac gactcccgct ggctcaatga   900
gcccaagttt gtcaaggtat tttggatccc ggagagcgag aacccagacg acgacaaaat   960
ctacttcttc tttcgtgaga cggcggtaga ggcggcgccg gcactgggac gcctgtccgt  1020
gtcccgcgtt ggccagatct gccggaacga cgtgggcggc cagcgcagcc tggtcaacaa  1080
```

-continued

| | | | | |
|---|---|---|---|---|
| gtggacgacg | ttcctgaagg | cgcggctggt | gtgctcggtg | cccggcgtcg agggcgacac | 1140 |
| ccacttcgat | cagctccagg | atgtgtttct | gttgtcctcg | cgggaccacc ggaccccgct | 1200 |
| gctctatgcc | gtcttctcca | cgtccagcag | catcttccag | ggctctgcgg tgtgcgtgta | 1260 |
| cagcatgaac | gacgtgcgcc | gggccttctt | gggaccettt | gcacacaagg aggggccat | 1320 |
| gcaccagtgg | gtgtcatacc | agggtcgcgt | ccctacccg | cggccaggca tgtgccccag | 1380 |
| caagaccttt | ggcaccttca | gttccaccaa | ggacttccca | gacgatgtca tccagtttgc | 1440 |
| gcggaaccac | ccctcatgt | acaactctgt | cctgcccact | gggggcgcc ctcttttcct | 1500 |
| acaagttgga | gccaattaca | ccttcactca | aattgccgcg | gaccggggttg cagccgctga | 1560 |
| cggacactat | gacgtcctct | tcattggcac | agacgttggc | acggtgctga aggtgatctc | 1620 |
| ggtccccaag | gcagtaggc | ccagcgcaga | ggggctgctc | ctggaggagc tgcacgtgtt | 1680 |
| tgaggactcg | gccgctgtca | ccagcatgca | aatttcttcc | aagaggcacc agctgtacgt | 1740 |
| agcctcgcgg | agcgcggtgg | cccagatcgc | gttgcaccgc | tgcgctgccc acggccgcgt | 1800 |
| ctgcaccgaa | tgctgtctgg | cgcgtgaccc | ctactgcgcc | tgggacgggg tcgcgtgcac | 1860 |
| gcgcttccag | cccagtgcca | agaggcggtt | ccggcggcaa | gacgtaagga atggcgaccc | 1920 |
| cagcacgttg | tgctccggag | actcgtctcg | tcccgcgctg | ctggaacaca aggtgttcgg | 1980 |
| cgtggagggc | agcagcgcct | ttctggagtg | tgagccccgc | tcgctgcagg cgcgcgtgga | 2040 |
| gtggactttc | cagcgcgcag | gggtgacagc | ccacacccag | gtgctggcag aggagcgcac | 2100 |
| cgagcgcacc | gccccggggac | tactgctgcg | caggctgcgg | cgccgggact cgggcgtgta | 2160 |
| cttgtgcgcc | gccgtcgagc | agggctttac | gcaaccgctg | cgtcgcctgt cgctgcacgt | 2220 |
| gttgagtgct | acgcaggccg | aacgactggc | gcgggccgag | gaggctgcgc ccgccgcgcc | 2280 |
| gccgggcccc | aaactctggt | accgggactt | tctgcagctg | gtggagccgg cggaggtgg | 2340 |
| cagcgcgaac | tccctgcgca | tgtgccgccc | gcagcctgcg | ctgcagtcac tgccctgga | 2400 |
| gtcgcggaga | aagggccgta | accggaggac | ccacgcccct | gagcctcgcg ctgagcgggg | 2460 |
| gccgcgcagc | gcaacgcact | ggtgaccaga | ctgtccccac | gccgggaacc aagcaggaga | 2520 |
| cgacaggcga | gagaggagcc | agacagaccc | tgaaaagaag | gacgggttgg ggccgggcac | 2580 |
| attggggtc | accggccgat | ggagacacca | accgacaggc | cctggctgag ggcagctgcg | 2640 |
| cgggcttatt | tattaacagg | ataacccttg | aatgtagcag | ccccgggagg gcggcacagg | 2700 |
| tcgggcgcag | gattcagccg | gagggaaggg | acggggaagc | cgagctccag agcaacgacc | 2760 |
| agggccgagg | aggtgcctgg | agtgcccacc | ctggagaca | gaccccacct ccttgggtag | 2820 |
| tgagcagtga | gcagaaagct | gtgaacaggc | tgggctgctg | gaggtggggc gaggcaggcc | 2880 |
| gactgtacta | aagtaacgca | ataaacgcat | tatcagcca | | 2919 |

<210> SEQ ID NO 3
<211> LENGTH: 36534
<212> TYPE: DNA
<213> ORGANISM: Homo sapiens

<400> SEQUENCE: 3

| | | | | |
|---|---|---|---|---|
| gatccatccg | cctcggcctc | ccaaagtgct | gggattacag | gcgtgagcca ccgcgcccgg | 60 |
| cccccaacct | tggacatttt | tcatccattc | attcatcctt | ttttttttt tttttttgag | 120 |
| acggagtctt | gctctgtcac | ccaggctgga | gtgcagggc | aagatctcag ctcctgcacc | 180 |
| ctccaccttc | cggattcaag | tgattctcct | gcctcagcct | cccaagtagt tgggattaca | 240 |
| ggcatgccat | caacatgtct | ggctaatttt | tgtattttta | gtagaaatgg ggtttcacca | 300 |

```
tgttggccag gctggtctcg aactcctgac ttcaggtgat cctcccacct cagcctccca    360
aagtgctggg attacaggta tgagccaccg cgcctggcgc atgggcacat ccattgagtg    420
tgcacttggt gccaagttct gtgccaggca caggcaattc aacatttatt ggaatgatgt    480
agtccctgtc tgcatggaat tcataggcta gaggaggaag cagtttgcct ctggtcccat    540
ggccagagca gccccaggtg aaggttatga attatttgtc ccatctaatg gtgttccagc    600
agtctgccac atggtgggaa ggaggcccca cagagctgtg ctgtctcctt cccaggatga    660
gctggagcac agcctggggg agagtgcggc caggggggca gctggagtgg tgctctgggt    720
gagctgggaa aatacaagaa ccaaggtgag cttaggcctg gcatgagggt gggggtgggg    780
gaggggtggg gccattaagc tgacggggta gaccctgact tacccttttct acctgcaaag    840 tcctggctga ccagcaggtg agtgcctcag tgccctgggt gggtccatac atggccatgg    900
tgtccctgac gctatcctcc cttcccacct aggaatcatg tcaggccatc aaggagtata    960
tggacactac actggggccc ttcatcctga acgtgaccag tggggccctt ctctgcagtc   1020
aagccctgtg ctccggccat ggccgctgtg tccgccgcac cagccacccc aaagccctcc   1080
tcctccttaa ccctgccagt ttctccatcc agctcacgcc tggtggtggg ccctgagcc    1140 tgcggggtgc cctctcactt gaagatcagg cacagatggc tgtggagttc aaatgtcgat   1200
gctaccctgg ctggcaggca ccgtggtgtg agcggaagag catgtggtga ttggccacac   1260
actgagttgc acatattgag aacctaatgc actctgggtc tggccagggc ttcctcaaat   1320
acatgcacag tcatacaagt catggtcaca gtaaagagta cactcagcca ctgtcacagg   1380
catattccct gcacacacat gcatacttac agactggaat agtggcataa ggagttagaa   1440
ccacagcaga caccattcat tccatgtcca tatgcatcta cttggcaagg tcatagacaa   1500
ttcctccaga gacactgagc cagtctttga actgcagcaa tcacaaaggc tgacattcac   1560
tgagtgccta ctctttgcca atccccgtgc taagcgtttt atgtggactt attcattcct   1620
cacaatgagg ctatgaggaa actgagtcac tcacattgag agtaagcacg ttgcccaagg   1680
ttgcacagca agaaaaggga gaagttgaga ttcaaaccca ggctgtctag ctccgggggt   1740
acagcccttg cactcctact gagtttgtgg taaccagccc tgcacgaccc ctgaatctgc   1800
tgagaggcac cagtccagca aataaagcag tcatgattta cttagctgtt tactgagcgc   1860
ctaaaatgtc caggccccgg tatccaaagg gcacaggaaa ggcttgtcac tctcaccaga   1920
tctgacgtca gtctaagggc ggctgcttcc cagggtgggg cccaaatttc aagaggaagc   1980
cccacctgat cggaccgttt ccaagctgtc ctggggcagg aggccggcgg gaaccgaagc   2040
tagacttgtc agagcctggg gcggggctgg cggaggcaga gccagctgga ggcgggcct   2100 gcgcctggct gaagtgacgt gctgggctgg ggcagggcct ggaagaagcc aaatcgaggc   2160
gggacctaag ctgtgacgca aggagaagga ggagggggcct gtatgggggcc gggtggggag   2220 gaggcggact caaatggaga tggggtgggg ctcagcaggg gcggagccag ggtagagact   2280
gagtcggcgc ctggcgggtg ttgtgacgcg caaaccaggg gcgggttcta gcggcgacg    2340 cgcgggtgct gggaggcctt agaacgccgt ggcgtgccgc aggacgcgac ggctgcagaa   2400
catccgccgc accgctgggg gccaacgttg tcggaccgag gagtccgagg tggcgactga   2460
gtgagatacc cagctgtgcg gagctaggac gcggaacatc ccagaggcca gcatcaacat   2520
gtcagtaccg cacccttccc atttgctgcc tgtaggtcca ccccgcgcgt gcggtcccca   2580
agtggccatg ccaccctgca cgccctcccc gcgtcagtcg ttcgtttcca gaccatgccg   2640
agccacacct gcccacagag tcgagctctc gaagtcctca ttcccaaaag ctccacagcc   2700
```

```
tgtgacccac taggagggag ggggaaaccg aggcccggga gagacggaga agccactctc    2760
tgaggacccc ggagccccgc ccacagtggg tgggtcggc actgaagggg ttaaggccgc     2820
ggggaagccc cgggctcagc cctaggggcg gatcctgggg cttcctccct ctagaccaaa    2880
gggtgcggct gctgcagagg tggctgatgc aggtgagggg cttacagccc tgtgaatggt    2940
gtgggaggtg aggggagggg ggtgcctgtt actgaccagt gtttaattgg cctcaagctc    3000
aggagaggta aggggagcca ggaggccccc tctggagcag gtgagtagaa ggaggggct     3060 cagctgcccg cccacgacta gaaaacccc agcatagacc tgccggacgg caggaccttg    3120
gttaagatgg gaaaacagta gggtttgggc acaggaggtc tgggccccca acctggtgac    3180
cgttggacac cctgtggata taggaaggaa gctgtggtcc ttatctaggg tgcctgcgaa    3240
actcaagcca gtgggaacc aagcctgcag aggcaatact gctgtgtgac tgtgggccag     3300
gcccagtgct ggtgctgctg gggccccatc tgaggagaca gttgggtcta tatccaaagt    3360
gtcctgagat gggcagagtt gggaaggggg ccatgggctc caggtgggga aggcagtcaa    3420
gacaggccaa agctcagcct gatgggtgca tgagtggggc cccaggatcc actaaggcag    3480
tgggcatagc ccaggtagtt gaaaaggctg ggagctggag gagactcgga acataggag     3540 aagaaaggga caggaagact cccgggcagt ttttcctatg gagggaacct tgggtaggtt    3600
tgagcagggg gtatagtgtc tgctttgcat cttctatccc atgccctagt ggtggactag    3660
gaggactact ggaagacaga aggccagcaa gtagattggg tcggctgttt tatagacctg    3720
gtggttacag acccctgtg aggggaggtc ctgaggagga caaatttgta gccagagcag     3780
gctggggcca ggactcctag gttctgcccc agccttaagc agctcatcca tcactcccag    3840
cctccctcca atgtggggta gacacctgga tctatctgcc ctgctctata ggggatgggt    3900
ctcttccagg tcacctgtgc tatcaggtga gtgtgggaca aagtgcagcc caccactccc    3960
cagttccagt atgcatggtc cccctgcac tctgtcagcc cttccctgct ccaaccccac     4020
cctccctcct ggcacagccc agcatggctg ttatctacag gaggagagcc actgtggtct    4080
gaagagatgc tactgcctgg agactgggt cttaacctcc agcctggcac tgagccacct    4140
gcaacctagc agcaggtgac cttggctccc agcctgactc agctgaacct ggatcctgtg    4200
cataggcaag agctgactct gagccctggc ccagccaagc tgaccctac actgaccct    4260 acacaccgga tggagctgat cctgagtacc agccagctg agctgactct ggatcctgcg    4320
tgccagccaa agctgcccct ggattccaca tgccaaccag agatgacctt caatcctggt    4380
ccaactgagc ttaccctgga tcctgaacac cagccagagg agaccccagc tcctagcctg    4440
gctgagttga ccctggagcc tgtgcaccgc cgacccgagc tcctggatgc ttgtgctgac    4500
ctcatcaatg atcagtggcc ccgcagccgc acctcccgcc tgcactccct gggccagtcc    4560
tcagatgcct tccccctctg cctgatgctg ctaagccccc accccacact tgaagcagca    4620
cccgttgtgg tgggccatgc ccgcctgtca cgggtgctga accagcccca gagcctctta    4680
gtggagacag tggtggtggc ccgggccctg aggggccgtg gctttggccg ccgcctcatg    4740
gagggcctga ggtctttgc tcgggcccgg ggcttccgca gctgcatct caccacccat     4800 gaccaggtgc acttctatac ccacctgggc taccagctgg gtgagcctgt gcagggcctg    4860
gtcttccacc gcagacggct gcctgccacc ctgcttaatg ccttcccac agcccctct     4920 ccccggccac ccaggaaggc cccaaacctg actgcccaag ctgccccaag gggtcccaag    4980
ggacctccat tgccaccacc ccctcccta cctgagtgcc tgaccatctc accccagtt     5040 ccatcagggc ccccttcaaa aagcctgctg gagacacaat atcaaaatgt gagggggcgc    5100
```

```
cccatattct ggatggaaaa agacatctga ggccatccag ggcaaggaac tgtctttctg   5160
gttcaataga ctgccccgac agtctacaag cctcagccca ctgaccatac ctcagcccct   5220
agcccctggg gggcagcttt aacctgggca tgtttcctgg gtaccagtgg ggccaggagg   5280
tggctctggc tcagagccgt cagtgtggct gaataaaggc tctcttgggt atggctgtga   5340
cagtttattt gttgatcccc ctaccctcac ctctcacctc ttctgcaggt cccttatccc   5400
tgcagaagtc tccagatcca ccttggccct gaggccattg atgggaggat gcctgtcctt   5460
tgcctttacc ccccacctgg ctcaggagac agggtggctg ttttcttccc cattcactca   5520
ttaccattca ctgagcacct actgtgtgtc aagccctgga cgggacatag gcaatgggta   5580
actagacaaa caggcataca gtagcaggat ccatgtggca caggggaggt acagaggctt   5640
tgggaaccca agtgacttca ctccacctgg ggatccagga gacctcccag ggcagtgatg   5700
tcacagcaga gacctgagtg ctaggtagga attaaaccag gcaggtgagg aggtgggagc   5760
tgactgttct tggaagaggg aacaaggtgg gcagaggaaa aaggggact tgtgacagtt   5820
gtgggaggac acagtggtgt attgacaaag acggaacatg ggagggaatg taccctcagc   5880
tcactgtaaa gcccgctttg gtgtgcacct gccactcgat gcccggggca tcatagccag   5940
cttgcggtgt ggctgcttta aaaggcccaa gagacccctg gggaaacatg ctttccccag   6000
ctcctcctgt aaggatgggg aggagctggg ggagctttcc tggctttccc tgccatgtgg   6060
aaggtgtggc catagctgcg gactctaagc ttacacccc ctctctcctg caggtttcca   6120
tccttgggga atgaccacgc aactgggccc agccctggtg ctgggggtgg ccctgtgcct   6180
gggttgtggc cagcccctac cacaggtccc tgaacgcccc ttctctgtgc tgtggaatgt   6240
accctcagca cactgtgagg cccgcttgg tgtgcacctg ccactcaatg ctctgggcat   6300
catagccaac cgtggccagc attttcacgg tcagaacatg accattttct acaagaacca   6360
actcggcctc tatccctact ttggacccag gggcacagct cacaatgggg gcatccccca   6420
ggctttgccc cttgaccgcc acctggcact ggctgcctac cagatccacc acagcctgag   6480
acctggcttt gctggcccag cagtgctgga ttgggaggag tggtgtccac tctgggctgg   6540
gaactggggc cgccgccgag cttatcaggc agcctcttgg gcttgggcac agcaggtatt   6600
ccctgacctg gaccctcagg agcagctcta caaggcctat actggctttg agcaggcggc   6660
ccgtgcactg atggaggata cgctgcgggt ggcccaggca ctacggcccc atggactctg   6720
gggcttctat cactacccag cctgtggcaa tggctggcat agtatggctt ccaactatac   6780
cggccgctgc catgcagcca cccttgcccg caacactcaa ctgcattggc tctgggccgc   6840
ctccagtgcc ctcttcccca gcatctacct cccacccagg ctgccacctg cccaccacca   6900
ggcctttgtc cgacatcgcc tggaggaggc cttccgtgtg gccttgttg ggcaccgaca   6960
tccccctgcct gtcctggcct atgtccgcct cacacaccgg agatctggga ggttcctgtc   7020
ccaggtaagt ggaagctgag gtctaggggt ctgagtcagg aggtatgcc ctgttctagg   7080
aaggtcccag gagaagacct tgcctagggg ttggtcctaa tctaggcgtt ctcagcggaa   7140
ggccctgtcc tggagcatct gatgaggag gcatggcttt gcctggaag atgttgaggg   7200
gtagggaggc ccagcctttg gagtgctggc ctgagggag atattctgag tggaaggcct   7260
gagaagccac tcagagactc gatacaaagg ggccctactt gggctgggtg agtgtctcac   7320
acctataatc ccagtacttt gggagcctga gatggaagga ttccttgagg ccaagagttc   7380
gagaccagcc tggcaacat agtgagaccc caacctctac caaaaaaaca tttgagacag   7440
agtcttgctc tgttgcccag gctggagtgc agtggcacca tctcagctca ctgcggcctt   7500
```

```
cacttcctgg ttctagtgat cctcccacct aagcctcctc ccgaatagct ggactacaga    7560
tgcataccac cacacccagc taatttttat attttttgtag agatggggtt ttgtcatgtt    7620
gcccaggctg gtattgaact cctgggctca agtgattctc ccgcttttgc ctcccaaagt    7680
gtgggattac aggtgtgagc cactgtgccc agcctaaaaa attattagcc aggtgttatg    7740
cacctgtagt cccagctgct tgggaggctg aggtgggagg attacttgat cccaggagtt    7800
caaggctgca gtgagctatg atcatgccac tgcactccag cctggatgac agagtaaaac    7860
cccgcctcta aaccaaacc aaactagaga gtccctactg tagagttaga atcagattgt    7920
gacagtgaac cagaagagtt tcttgaatgt ggatgtgtgc ccacatggat ctggccagcc    7980
cagcactggc ttagcagctc tctgcctcca ggatgacctt gtgcagtcca ttggtgtgag    8040
tgcagcacta ggggcagccg gcgtggtgct ctgggggggac ctgagcctct ccagctctga    8100
ggtgatcatt gccctttga gcctgccatg tagcacatgc tggggtccca gggtggggga    8160
cggccatgtc aagattatag agcaggcata ttgacacata tcttcccttc tcctcaggag    8220
gagtgctggc atctccatga ctacctggtg gacaccttgg gccctatgt gatcaatgtg    8280 accagggcag cgatggcctg cagtcaccag cggtgccatg gccacgggcg ctgtgcccgg    8340
cgagatccag gacagatgga agcctttcta cacctgtggc cagacggcag ccttggagat    8400
tggaagtcct tcagctgcca ctgttactgg ggctgggctg gccccacctg ccaggagccc    8460
aggcctgggc ctaaagaagc agtataaagc cagggcccct gccactgcct cttcttttcc    8520
ctgctgccca ttttccagtc ctggaactac tctgtcccac tcttgctcta ttcagtttac    8580
agtcaaccct cccaagcaca caccccgctt cccttggaat ccctgagggg tagaagggc     8640 cagaaaaaac gcttataaaa ccagaggccc tctgagatca tgtgagtcct ccatggcaag    8700
gaagcagttc cagggagagt caggttccag ctagttaggg ctgccagcct agggctttgt    8760
gcctacacct cactaagccc atggagaggt cacagatggg ccgtgcacgg gcagatgggc    8820
cccaaaaaat cttggcgaag gtcggtaaag tgctaagctg ttgtctgcac tctttcatca    8880
taaagtcact tttttccact gcctgaggtt tggctgttgc tcctgttatc ccaagctcta    8940
agcccttccc atggtcccca gacccaggca ggggtaggtc tcgtctggag tgtcccgctg    9000
ccaagtgccc tgagaagcca gtcctgcctt ggtgctccac tgagggacgc ttcggagtta    9060
accaccgtgc acttgttccc gacgcggggc tggggcgcgc gcagggcatt gtgggtgcat    9120
agttcagcca gcgcgtcgtc ggctggtggg ccccaggcgt ggactaccat tcccatggtg    9180
ctctacgcgc agctagccgc cgtcgcctgc gcgctcaggc ctctgggatt agtagtttta    9240
gcctcgtgga tgtgggcctg aatcggatgg cctggaactc gccttcccgg cgacctgttt    9300
ggcagggcgg ggcgcctcgc gaagatggtg gcgcgcgtgg cgtgtggctc ccgtcgtctg    9360
gccaagtctc agcgcagcgc accggccggc gtctcgttgg cctggagccc acacccaccg    9420
ggtccctgac cccgcgcccc ccgcgcccgg ttcccggcat gcctcgcgcc cgtaagggca    9480
acacgctccg gaagggtggt cagcgccgtg gaggaggtga gtggggtggg gggcgcggga    9540
cagctgtatg agcggcgggc gggggtcctg ctggatcccc ttggttgttc tcgagggccc    9600
tgggtgggga acccctcgg ccagccccac gcagcttccc ataactctac cgaggctggc     9660
acgtgcccca gcagtcattg gccacgtgcg tgcccaactt gagctcgctg cccactgcct    9720
gttgggagtc cgcgctccca gcggtgaccc ggccagcccc tccgggcctc agttgcctgc    9780 tgggtgggaca aactcaccgg acagggcagg aagccagtcc tcttgccaaa ccctgatcct   9840
ttcctggact ggtcaaggaa gttggcggga gtcctggcct gctccggtga agagagggag   9900
```

-continued

```
ggggctctgt tgggaagcta cctggttagg gccttggcag cttggcaggc ctgactccac      9960
aaggtagctg agtatcctgg agcctgaggc agtcttggga ctcgcttatc agcttagacc     10020
aggagcctat cttaatgcgt taaacacata tgtttactct gctgggatgg ggtgcctacc     10080
acgcacaaat ttatttattt ttattcttga gggggaaggg aggagggccg ggcacaggaa     10140
ggaggaaaat acctaggcac aactttaaac tggtcaccac catggtgggt tttgggtggg     10200
ggacatctaa tagggtgtgg aacatgttca ctgagtggtg tcagcccag acttaggact      10260 cagggaggcc tgggggggaag tgcttctggg tgagtcctga gaggatggag aagagagcaa    10320
gttgtacaaa gacctggcag ctggaggac cccagcgcag tggagtgaat gagggaaggc      10380
tgggctgctc cggcaggtag aatagtaaga taaaatggga gcaggctggg cgtggtggct     10440
cacacctgta atcccagcac tttgggaggc caaggcaggc agatcacctg aggccaggag     10500
ttcgagacca gcctgaccaa catggagaaa ccctatctac taaaaataca aaattagctg     10560
ggtgtggtgt cgtatgcctg taatcccagc tactcgggag gctgaggcag gagaatcact     10620
ggaacccggg aggcagaggt cgcagtgagc cgagatggcg tcattgcact ccagcctggg     10680
caacaagagc aaaactctgt ctcaaaaaaa aaaaaaaaa aaaaaggtgg cggggagcag      10740
aggccagtgc gcaggctgga cttgtcctg cagatgaggg gtgtgagtag ttcttagaag      10800
tagggccagc ctggtgatca caccctgtcc aaaactctgc cacagcagcc aaccttgcca     10860
atgtcagccc ttggccctgg acagacccca cacacaggag tgcaccagcc ctactgaact     10920
gacccttggc tttggttttt catctctgag agggacacca ttctatcttt tgggattatg     10980
aggtcgagtg aggtaccccc agccatccct catcagtaga ggcaagttga gtgtcctatt     11040
ccaccttctc caggtgcccg gagcagtgcc caagctgact cgggttccag tgacgatgag     11100
gcagccagtg aggcccgcag caccgccagt gaatgcccca gccttctcag caccactgca     11160
gaggacagcc ttggtgagag cgggtggaag tttgacaggg gcttggtgag ggctccatgg     11220
gctgaggaca agaagcggtg ctgaccaggt ggccttgcag ggggggatgt cgtggatgag     11280
cagggccagc aggaagacct tgaggaaaag ctgaaggagt atgtggactg tctcacagac     11340
aagaggtacc cctggctgcc agccaactcc tacacccagc tccaagtgtg atcaagggag     11400
ggctggccca tatgaccccc cttctcgacc tcccccagtg ccaagacccg gcagggtgct     11460
cttgagagcc tgcgcctggc cctagcgtcc cgcctactcc ccgacttctt gctggagcgc     11520
cgcctcacgc tagccgatgc cctggaaaag tgcctcaaga aaggttggac ctgggggtgt     11580
gtgggagact taaactgggc agacactggc ccttgctgca tgggctgact ggaaagcatc     11640
ccacagggaa gggcgaggaa caagccctgg ctgctgctgt gctaggcctg ctctgcgtgc     11700
agctgggccc tggacctaag ggtgaggagc tgtttcacag cctgcagcct ctgctggtct     11760
ctgtgctcag tgacagcaca gctagccctg ctgcccggct ccacgtgagt gtgcctgtgc     11820
cccatgaaac ccttcctgca ccttatccct cagcagagtg tgggttccc ctatcttca      11880 gcctccttta ctctgagggg agtgagctcc agggctggga acccaggttc acccgctgac     11940
cgtggcattg cattgcccctt ctcccaacag tgtgcttctg cccttggcct gggctgctac    12000
gtggctgccg ctgacatcca ggtgaggggt ctttgggcac aggtggtaga gcatctaggg    12060
ctgtaactct gcctctgagc tcccctgcct ctctgtgctc ctaggacctg gtctcttgcc     12120
ttgcctgctt agaaagtgtt ttcagccggt tctatggctt gggggggcagc tccacaagtc    12180 ctgtggttcc tgccagcctg cacggcctgc tctctgctgc cctgcaggcc tgggcattgc    12240
tgctcaccat ctgccctagc acccaaatca gccacatcct tgacaggtag ggtggctgt     12300
```

```
ccactgggag ggggagggga tctcaaagag gcccccaagc cacacatata gctcagcctg   12360 cccccttccct aggcagctgc cccggctgcc ccagctcttg tccagtgaaa gtgtgaacct   12420
gcggatcgct gccggtgaaa ccattgcact gctctttgag cttgcccggg accttgaggt   12480
gcgagggaca aggatggggg gtgcttggtg acaccacctg cccatcacag gctggatgca   12540
gggggtgcca cacaaaacag aacagcttta ggtcattatg cagaggaggt ggccccaaaa   12600
cagatttatc tcctagatgt catgatgggt gccctcagca gtggtgtcct ggcctgacag   12660
aggccaagga ggggtcaaag gggccaggca gagaagagag ggtctctcag tgaaaggagg   12720
ggtttgggca gtgccctgtt cagagccagc agagctcaag catctaccac acaccctcca   12780
atgctcccat tgcaggagga gtttgtttac gaggacatgg aggccctctg cagtgtcctg   12840
cgcactctgg ccactgacag taacaagtac cgtgccaagg ctgatcgtcg gcgccagcgc   12900
tctactttcc gcgccgtgct gcactccgtg gaggtgtgtg tgagaacata tgtgtcctag   12960
caagggtgca cccccaggca tagcagccaa gcccagttgt gttggcacct ctaccctgca   13020 ggcggtgaa tgcgaagaag agatagtgcg cttcggcttt gaggtgctct acatggacag   13080
ctgggctcgg caccggatct acgctgcctt caaggaagtg ctgggttcgg gcatgcacca   13140
ccacctccag gtgcggggac ggacagggag gggacatctg gtgtggttgc ttcagtctgg   13200
cctgagctca ctgccctctg cccccagaa caatgagcta ctccgtgaca tctttggcct   13260
gggccctgtg ctgttgctgg atgccactgc cctgaaggcc tgcaaggttc cacgctttga   13320
gaaggtttgc acccttgggc acctttctct tccccctatt cccatttcct ggaggcctgg   13380
aattctgtag aggccggaag aggaccccca gcccttccc ttcccagctc cccagggtgt   13440
cactctctgt ccccactcta gcacctgtac aatgctgctg ccttcaaagc ccggaccaag   13500
gctcgaagcc gtgtgcggga caagcgggca gacatcctgt gaagcaggac ctgctgaaga   13560
ggagactttc tatgcccttg gtccgtattt ttaacagaag acagtgcaac aactggtctc   13620
caccagtatt tgtcacttta ttttttttaa tgacaaaacc aaaaacagac atggggtggg   13680
tagctggggg cccggacact tgggaccctg accccttggt ccctgcactc agccctgtgg   13740
ccccttcctg tcctgtctca ggccaggcta aatatgtgcc ttcctcaggg ctgtggggca   13800
ggcactaggg ggccttccc ttcctttcct ttctcaggcc ttgctccccc aggatgaccc   13860
actcttaggg gggtggtggc atctggacaa atgccaccac agcaggtggg gtggcaaagc   13920
tacctggaat ggatttgtgt gctgattttt aaggattatt acagataatt aaacagaacg   13980
gtcagccttc tgtggtctta acccctgggt attttctgt tctccctccc catctactat   14040
cccaggcttg ggcccaactg gtcttccacg atgtcacctt tgccctccaa ggcagtcttc   14100
cccaggtggt gcctctcccc ctactcagag cccagcctgt ctttaagagc tgaggctgga   14160
ccctcactgg gagccctggc agagtttggg tgattgctat gggggcagct atttctagac   14220
ttcagaacct gccatctggg gtggccagag agtgttgaca ggcacaggga ggagccagga   14280
ggctggtgcc ccttcccctg accttgggcc acccaaagcg aggctttggc accagaggct   14340
tggctaggcc tggcttgaag agatcaggag agggaggcag ccattaagtt aacaacaggt   14400
tcttgtacaa aaatctcacc aaggaaatag tgtagatgtg gcagccagca gtagggaagg   14460
agagacctgc ccatagccac tttattcccc caccaacaca caccccagg ccccagatcc   14520 aaatggcatc tcagctgggt gcttgggcct cactggagtt gagcctccga agctggctga   14580
ggctggccaa gcgagttg agtagtgtct cctcctgcgt gcggagcgtg tgtgccagga   14640
tgcgcaggga ttcactctgc agcactgtga atgggaagtg ggggatcatc agaccatgtg   14700
```

```
ccaccccgtg acccctgcag acccagccca ggaccagggg cagccacggg cctcccgccc    14760
catccttcac tgctgcagca tctgcagtta ctccttccag ctgcacagaa gggcctccca    14820
gtccccactg ccttgctttc cattcctact agcaccctat gcgtccatac cgctcaggta    14880
gacagccagg agtgcgagca ctaggcaagt gagcaccagc agcgcgagca gcagcaggaa    14940
ccctcctcgt ctgtacacag ggctgcagcc agcctgggca cacagtgacg gcggcaaaac    15000
gcccagcagc tcatcccacg gtcgtgcctc ttcagttaga taggggcgca gtgtgcctgc    15060
tgggtggatg ggacattggg agggtggtgg gtgcacctgc tttcgtcccc tcccccagca    15120
catcatccac cccactgtcc ccactcacct ccactatgta ggtcgctgat ggactccacc    15180
tggtgcaggc atacctcatg cacgtggttg ggggccaatg gccccctgct cctctggctg    15240
ggcatcattg gcgccacgga gtctgcaggg gcagcgcagg ctgatttagc cagtggtggg    15300
tcaaccccct tccttctacc aggtggcttc aggcagcaag gacttgcgga tgatagggat    15360
agtgggacat ttggttccaa atcccctaaa actgactcag gaattaccct tgatttggat    15420
ccaggatgat cccagaccct tacaggctta ttctgtatac aggagcaaca ggtacatttg    15480
atttgttttcc ttccaagcac cccagggact cactcaggca ttcctctgcc tgcttatttc    15540
tagcagttta tcagccttga atgctaaacc tgcagcaaat ggaattcagt cctgcctctt    15600
ttgtcagttc tccctgcaga cccaatgcct ggcatcttct ggtcagaaag ccctattgta    15660
gccactctgg tgcctttccc tcctggcctt ggttctgtgt ttgttaacat actcagtgtg    15720
actctgctgt acatgtgtga accctgctgt tttcattcaa catttactgt tggggagacc    15780
cttctttgtt atactgttgc acatgcctct gaggtctctc ccttcacaca tctccctgag    15840
gctgcctggg catctaggtt gtttgcagtc cccgccccc tttttttttt gagacggagt    15900
ttcgctcttg ttgcccaggc tggagcgcaa tggcgcgatc ttggctcacc gctgcagttc    15960
ccttttgaaa ttaacccca ggacatccac cgttgaatat gaaggttttt tcccaatttc    16020
ctgatagttt aattcccaga agtggaatta ctggatccaa gagcagggat ttttgtttgt    16080
ttgtttgttt tttgagatgg agtctccctg tattgcccag gctggagtgc tatgtcgtga    16140
tctcgcctca ctgcaccttc cacctcctgg gttcaagcga ttctcctgca tcagcctcct    16200
gagtagctgg gattacaggc gtgtgccacc acgcccagct aattttttgta ttttttggtag    16260
agatgaggat tcaccatgtt ggccaggctg gtctggaact cctgacctca agtgatctgc    16320
ccgcctcggc cttccaaagt cctggcattt acaggcatga ccactgcat ttggtcgttt    16380
tttgttttgg tttgttttt ttaagatgga gtctccctct gtcgcccagg ctggagtgca    16440
atggcaagat ctcggctcac tgcaacctct gcctcccggg ttcaatcagt tctctgcctc    16500
agcctcctga gtagctggga ttacaggcgc cttccaccac acccagctac ttttatatt    16560
tttagtggag atggggtttc accatcttgg ccaggctagt cttgaaccc tgaccttgtg    16620
atccaccac ctcggcctcc caaagtgctg ggatttacag gcgtgagcca ccgtgcccgg    16680
cctgttttt tgttttgag acagagtctt gctctgttgc ccaggctgga gtgcagtggc    16740
gcaatcttgg ctcattgcaa cctccactc ctgggttcaa gtgattctcc tgtttcagcc    16800
tcccaagtag ctgggattac agatgtgtgc caccacgccc tgctaattt tgtatttca    16860
gtagaaacca ggtttcacca tgctggctag gctggtctca aactcctgac tcaagtgat    16920
ccgcccgcct cagactccca aagtgctggg attacaggcg tgagccatcg cgcctggcct    16980
gagattttg ttttgttttt gagacagatt cttactcttt cacccaggct ggagttcagt    17040
ggagtgatca cagttcaccg cagcctccac ctcctgggct caggtgatcc tcctgcatca    17100
```

-continued

```
gccttcccag tagctgggac tacaggcatg cactaccatg cccagttaat ttttttttgta    17160 ttttttgtag agacagggtt ttactatgtt gcccaggctg gtctcgagct cctggtctca    17220
agagatccat cctgcttggc ctctcaaaat gctgggatta caggtgtgag ccaccatgcc    17280
cggcctgatt tttttttaaag ctattaccaa actgtcctcc agaagcactg tccacagctc    17340
ccccgcaggg tataatattg ccaccattag gcatccccat aggaaaaaaa ttatatttac    17400
atgcacacgt gcacacatat atttgctaac ttgagagatg agaaatggtc tttcttattt    17460
tattgggttt cttagcctag ggagtgtgac taatacgtgt gtggcgcttt ttttttttt    17520 ttttttttg agacagtctt gctgtgttgc ccaggctgga gtgcagtggt gcgatctcag    17580
ctcactgcaa cctccacctc ccaggttcaa gcaattctcg tgcttcagcc tcccaagtag    17640
ctgggactac aggcacctgc caccatgcct ggctaatttt tgtatttttta gtagagacca    17700 ggttttgcca tgttggccag gctggtctca aactcctgac ctcaagtgat ccacccgcct    17760
tggcctccca aagtgctggg attataggcg caagccacca tgcccagctg tgtgtggctt    17820
cttaattatc aatttgaagc ctctgcccat ttagtcactt gggtctgtgt acttttcttt    17880
tgattttaat tatgtacttt cacactcatt gaagttttg cttttttgttt gtttgtttga    17940 gacagagtct ctgttgccct ggctggagtg cagtggcacg atctgggctc actgcaacct    18000
ccgcctcccg ggttcaaggg tttctcctac ctcaccctcc ttagtagcta gcactacagg    18060
tgtgcaccac cacacccctgc aaattttttt tttttttttt ttttttgaga tggagtctcg    18120
ctctgccgcc caggctggag tgcagtggca cgatctcggc tcactgcaag ctccgcctcc    18180
caggttcgtg ccattctcct gcctcagcct cccaagtagc tgggactaca ggcgtccgct    18240
gccatgcccg ctaatttttt tgtattttta gtagagatgg ggtttcacca tgttagccag    18300
gatagtctcg atctcctaac cttgtgatcc gtctgcctca gcctcccaaa gttctgggat    18360
tacaggtgtg aaccaccgcg cccggccaat ttttgtattt tttgataaag atggggtttc    18420
accttcttgg ccaggctggt cttgaactcc tgacctcagg taatccaccc gcctcagcct    18480
cccaaagtgc tgggattata ggcgtgagcc atcgcaccca gccggtgttt cgtttgtttg    18540 tttgttttg agacagaatc tccctctctt gccatgctgg agtgcagtgg cgcaatctca    18600
gctcactgca acctccgcct cccaggttca accgattctc ctgccttagc ctcccgagtg    18660
gctggaacta caggcacgtg ccaccacgcc tggctaattt ttgtattttt agtagagacg    18720
gggtttcacc atgttggcca ggatggtctc gatctcttga cctcgtgatc tgctcacctc    18780
agcctcccaa agtgctggga ttacaggcat gagccaccat gcctggcctt ttgttgtct    18840 gttttttttg agacagagtc ttactgtgtc acccagactg gagtacagtg gcatgatctc    18900
agctcactgc aacttctgcc tcctgggttc aagtgatttt cctgcctcgt ctccccagta    18960
gctgggatta caggcacgtg ccaccatgcc cagctaattt ttgcattttt agtacagctg    19020
gggtttcacc attttggcca cgctggtctt gaactcctga cctcaagtca tctgcccatc    19080
ttgtcctccc aaagtgctgg gtttacaggc atgagccacc gtacctggcc aatatttaat    19140
tatattttct tctagttgtt ctttaacttg atgtctaaaa atcctggtcc agatgccaag    19200
agctccagat acccacctgg aagctgataa cagtagggaa gagcattgag gggacacctc    19260
cagataggag caagggtggc cttgcactct gggactgtca ttctcaggac agtaactcaa    19320
cctccatgat ttacttgaaa ctgcctcttg acgtgctcaa aagcaagtac aacaaaaaca    19380
agcaagtgct gccagtcatt atgtctgggt ggtgggttga aggtcatatt aaattctctc    19440
tttgggccgg gcactgtggc tcatgcctgt aatcccagca ctttgggagg ccaaggcagg    19500
```

```
aggatcattt gagtctaaga gtttgaaacc agccagggca acgtagggag accccatctc   19560
tacaaaaaaa tcaaagatta gggccgggca tggtggctca cacctgtaat cccagcactt   19620
tgggaggctg aggtgggcgg atcacgaggt caggagttca agatcagcct ggtcaacatg   19680
gtgaaacccc atctgtacta aaaatacaaa aaattagccg ggcatggtga tgggcgcctg   19740
tagtcccagc tactcaggag gctgaaggca ggagaatagc ttgaaccag gaggcggagc    19800 ttgcagtgat ccaagctcaa gccactgcac tccagcctgg cgacagagc tagacctcgt    19860 ctcaaaaaac aaaaaagtaa ttaaagatta gtttggtgtg gtggcatgct tctgtggtcc   19920
cagcttctca ggaggctgag gtgggagggt tgcttgagtc caggaagtca aggctgcagt   19980
gagctgtgat catgccattg tactccagcc tgggcaacag agtgagaccc tatctccaaa   20040 aaaaaaaaa aaaaaaaaaa aattccctgc tgccgggcgc agtggctcac acctataatc    20100
ccagcacttt gggaggccaa ggcaagtgga tcacaaggtc aggagtttga ccagcctg     20160 gccaatatgg tgaaacccg tctctaccaa aaatatttaa aaattagcca ggtatggtgg    20220
caggcgcctg tagtcccagc tacttgggag gctgagacag gagaatcact tgaacctggg   20280
aggcagaggt tgcagtgagc agagatcgtg ccactgcact ccacccgggg cgacagagca   20340
agactccgtc tcagaaaaaa aaaaaaaaaa aagggccggg cgcagtggcc catgcctgta   20400
atcccagcac tttggaaggc cgaggtgggc aggtcacgag gtcaggagat cgagaccatc   20460
ctggctaaca cagtgaaacc ccgtctctac taaaaaattc aaaacaaaaa ttagctgggc   20520
atggtggctg cgcctgtag tcccagctac tcgggaggct gaggcaggag aatggcatga    20580
acccgggagg cagagcttgc aatgagccaa gatcgtgcca ctgcactcca gcctgggcga   20640
cagagcaaga ctctgtctca aaaaaaaaa aaaatttccc tctttgtact ttgttgtgct    20700
tttctcacac tttctaaatt gaatgtgaat tgtttattac aggaaaaaca cacagtaaat   20760
gttattgtta agatcccaaa agagggtagg cacagtggct tatgcctcta atcccagcac   20820
tttgaaaggc caaggtggct ggccgggcgc ggtagctcac acctgtaatc ccagcacttt   20880
gggaggccga agtgggtgga tcacgaggtc agaagatcga gaccatgccg gctaacacag   20940
tgaaacccca tctctactaa aaatacaaaa aattagccag gcgtagtggc gggctcctgt   21000
agtcccagct actcaggagg ctgaggcagg agaatggcgt gaacccggaa ggcggagctt   21060
gcagtgagct gagatcgcgc cactgcactc cagcctgggc gacagagcga gactccatct   21120
caaaaaaaaa aaaaaagaa aagaaaggcc aaggtgggag gattggattg gttgaggcca    21180
ggagttcaag accaggagag cccttctcta cacacacaca tgcatgaaag taaacatttc   21240
cccctaccag gggcaaggcc cctctcctgc aatgttgaaa atgttggcag tggctcacgc   21300
ctgtaatccc aacaatttgg gaggccaagg tgggtggatc acctgaggtc aggagtttga   21360
gaccagcctg gccaacacgg tgaaaccttg tctctactaa aaatacaaaa attagccggg   21420
catggtagca catgcctgta atcccagcta cttgggagcc tgacagga gaatagcttg     21480 aatctgggag gcagaggttg cagtgagccg agaccgcacc actgcactcc agcctgggtg   21540
acaaaaaaaa aaaagttga ggccaggcgc ggtggctcac ccctgtaatc ccaacacttt    21600
gggaggctga ggtgggtggc ttacgaggtc aggagttcaa gaccagcctg gccaagatgg   21660 tgaaccccg tctctactaa aaatacaaaa attagctagg catggtggca ggcgcctgta    21720
atcccagcta cttgggaggc tgaggcagag aattgcttga atctgggagg cggaggttgc   21780
agtgagccga gatcacgcca ctgtactccg gcctgggtga cagagcgaga ttccatctca   21840
aaaaaaaaaa aaaagttgaa aatgtgataa gaggagcttg ctagctgggc catgctctgt   21900
```

```
catgggccat aacatggagc catggagcag acagtcctac gtcctggcca gtactggacc   21960
tgtagcttcc tagattcctg ctgccctggc ccctctgagc atcagtactt cttatatgca   22020
gtggtgcagt taggtgagtg gccaccaagc tcttgactag ctgagtctct gtctgaccag   22080
gccaagggac ccccaaccct aggcagttgg ggatatttag acccaagtca ggggaggcca   22140
gaggcctaac tacttttcag tccatgggac aggtacccaa atgctttctg aaccactac   22200 ccaccccaat cccagcttcc ttccttaaga gctgaaccgg ccaggcagct gaccggatgc   22260
ccacacccac ctgagcacag cctgtagttg acccactcct aactgggtag cttctcccat   22320
ccctccttga tgtccccagc aggggaaact gaagcagggc ctgaggtgac aaggggctcc   22380
aggcatggca ggcttttcct ccctgcacag ggggcaggtc cttttactgg agctggagca   22440
tgaaaatggg taactaacta ctcaagacag tgaggtcagt gggacagagg gtgggtctct   22500
ccatggtcca caaggtcaca ggactgaggc cttgccctcc ctcatggtca ccctctccta   22560
ccttcttggg tctcctcagg catggcaagc agtgggcagt cggggccaa tgatggcatc   22620 cagtagcagg actggacaaa tgcagcagtg gctcctttgt gagcccaggg aaggcctggc   22680
tgcctcccag ccttggccta aaataggcct gagctcagcc cactgggcta tatttagagg   22740
gggcagccct cagccatggg aaggggcaga gtgatccacg tgggccagcc tgaactatct   22800
acctggtgag ggagccagcc aggagcctgc ctccactagt ccaggtgccc agggaccttc   22860
aaggggaagc acacctcccc catacatcca gaatggccac tccaggctca gcaaggcccc   22920
atgtggcagc caagacagac aaaggaagcc tgtgcatctc tatttggcca cccctctacc   22980
cctgcagact cctacccaca gcccagtcat ctctcctccc agcaaacaca gcagcctcca   23040
ctgcatgacc tgctagcaca caatgctatt gttgtgtgtg tcttatagag ggtgatggac   23100
aactgaatcc caatgccatg agggctctga tagcttcaca agtgggcaga tacaccaaca   23160
gcacccatgc tggccagtgg gtggacctag gttggaggct ggttcatttg ttactaagct   23220
tgcaacctta ggtaaagggt ctcccctctc tgaactcagt ttgctcatgt gtaaagtcgg   23280
aataacagtg gctcctccct ggcagtgtac actgagaaca acatctggag catttagcac   23340
aatccacggt tttggtcttc ccctgctccc atctccacaa gggcagacag gtcccataag   23400
gttgtgtaag gatgcgcatc actgcttacc ttgaaaggag gaggtggtcc agcttccagc   23460
tttccctctg tggttggatc cctgtgccct tccttcccag tgggggcaaa gcaagactgt   23520
gggctctact tcctacacac ctcaaacctg tcactccgtt gtctcacact ggcctccctg   23580
atgttcctca aagtcaacaa gcttgttacc acctcagggg cttggtggtg gctgttccct   23640
cctggaatgc tctgctccca gatagccctg tggccagccc cgtcttgtca gcgaactcaa   23700
atgccacccc ttcagtgagg ccttctgtgt acattctttt ccacatcacc cagttttctt   23760
ttctttgaga cagagtctcg ctctgttgcc caggctggag tgcagtgggg cgatctcggc   23820
tcactgcaac ctctgcctcc ctggttcaag caattatctt acctcagcct cctgagtagc   23880
tgggattaaa ggcgcgtgcc atcacaccca cctaagtttt gtatttttag tagagacagg   23940
gtttcaccat gttggtcagg ctggtcttga actcctgact tcatgatccg actgcttcgg   24000
cctcccaaaa tgctgggatt acaggcgtga gccactgcgc ccggtccagt tttattttct   24060
tcctagcact tagtcctgaa gttatattat gcacaatgta ccctgcgtgt cactattccc   24120
aaaggcccta cagaacctgt tcagtcacgc ggaaccacct tttttttttt tttttttttt   24180
ttttttggag tctcgctctg tcgcccaggc tggagtgcag cggcgagatc taggctcatt   24240
gcaacctcca cctcccaggt tcaagcaatt ctcctgcctc agcctcctga gtagctagga   24300
```

```
ttacaggcgc cgccaccac gcccgactaa ttttttgtat ttttagtaca gacgggttt    24360
caccgtgtta gccgggatgg tttccatctc ctgacctcgt gatccgtccg cctgggcctc    24420
cgaaagtgtt gggattacag gcgtgagcca ccgcgcctgg ccggaaccac ctttaatcct    24480
caccaggcaa ccttggacag gagaaactcg ggccctgaca ccgctagtaa ggtgcccaag    24540
accacatagc aaggccgagg actggggttt tctgctgggg ccattccagc tttggctgat    24600
aatgcgttta ttgcgttact ttagtacagt cggcctgcct cgcccacct ccagcagccc    24660
agcctgttca cagcttttctg ctcactgctc actacccaag gaggtggggt ctgtctccca    24720
gggtgggcac tccaggcacc tcctcggccc tggtcgttgc tctggagctc ggcttccccg    24780
tcccttccct ccggctgaat cctgcgcccg acctgtgccg ccctcccggg gctgctacat    24840
tcaagggtta tcctgttaat aaataagccc gcgcagctgc cctcagccag gcctgtcgg    24900
ttggtgtctc catcggccgg tgaccccaa tgtgcccggc cccaacccgt ccttctttc    24960
agggtctgtc tggctcctct ctcgcctgtc gtctcctgct tggttcccgg cgtggggaca    25020
gtctggtcac cagtgcgttg cgctgcgcgg ccccgctca gcgcgaggct caggggcgtg    25080
ggtcctccgg ttacgccct ttctccgcga ctccaggggc agtgactgca gcgcaggctg    25140
cgggcggcac atgcgcaggg agttcgcgct gccacctccg cccggctcca ccagctgcag    25200
aaagtcccgg taccagagtt tggggcccgg cggcgcggcg ggcgcagcct cctcggcccg    25260
cgccagtcgt tcggcctgcg tagcactcaa cacgtgcagc gacaggcgac gcagcggttg    25320
cgtaaagccc tgctcgacgg cggcgcacaa gtacacgccc gagtcccggc gccgcagcct    25380
gcgcagcagt agtccccggg cggtgcgctc ggtgcgctcc tctgccagca cctgcgggca    25440
gagggcagcg tgaggcgggg gtgtcgggcc gggaacaggg cttccgggcc ctagcacgcg    25500
acggaagaag caaagagtca ttgggagccg aggtggagcg ggaaaggggt gcccgcaggc    25560
gcacatttta aggctgagtg tttgggagct ggtggtcttc aagggagaat ccgaaagagg    25620
cggggtttac atgaacttgg tgggggggtgg tcagggacct taatgggagg gtcgagggcg    25680
ggtcttctcc ttgattcagg ggaggcgggt cgggagcccc gttggacgca atggggcctc    25740
agcagcttgt ggagtgcagg tgagggacca aactggacag ggcgggagt gggtctggtt    25800
ggacggggct tcgttgggta gggcgggggcc tctcctggat gcaggggtg ggacaggagc    25860
ctggcgggga gggcggagta aggctcacct gggtgtgggc tgtcacccct gcgcgctgga    25920
aagtccactc cacgcgcgcc tgcagcgagc ggggctcaca ctccagaaag gcgctgctgc    25980
cctccacgcc gaacaccttg tgttccagca gcgcgggacg agacgagtct tggggcgaga    26040
agaaagtcag atttaggcaa ggcagggcag gtgggggcgtc ttctgggct gagggtaggg    26100
gcagctgggc cactcacctc cggagcacaa cgtgctgggg tcgccattcc ttacgtcttg    26160
ccgccggaac cgcctgtggg gaacatccga tcttctgtga gccttctttt cagccccggg    26220
cagtgaaaga cccttcgcct ccctcccggc ggcccaaccc cgaccccgcc cacctcttgg    26280
cactgggctg gaagcgcgtg cacgcgaccc cgtcccaggc gcagtagggg tcacgcgcca    26340
gacagcattc ggtgcagacg cggccgtggg cagcgcagcg gtgcaacgcg atctgggcca    26400
ccgcgctccg cgaggctacg tacagctggt gctaggggc acgagggggct ctgggctgac    26460
cgagggcgac cccacgcctg cctcccatcg gtcaggatc ccttcttcca ctcgacagat    26520
gggaacactg aggtcttacg cctcaggtca cacagtctaa caaagccaga gcctgtactc    26580
aaacccggga ctgcaaacta ccaaaagggg ccagaggctt gggacgcgcc aggcacaagc    26640
tcagtccatc ccaccccgac ccccatcctg gtcactcacc ctcttggaag aaatttgcat    26700
```

```
gctggtgaca gcggccgagt cctgagaggg aggaggggcg acggggtcag ggcttagtgg    26760
ggtgggggg  tcccgggcga ctgggggtga ggcctcacct caaacacgtg cagctcctcc    26820
aggagcagcc cctctgcgct gggcctactg cccttgggga ccgagatcac cttcagcacc    26880
gtgccaacgt ctgcagggat gagaagggg aatgaccatt ggtgctcccg acagctggg     26940
gctagtgtct cctcgccttt gaggcgtcta ccctcagcat gtttggttg  tgaagagtgt   27000
ggactggaag agtgtgggt  gggcagcatc acagggtgg  agacacagcc caggaaagga   27060
tgtggagatg ggactgaaca gggagagctt ccatcagcag cccacagggc ctggctggga    27120
gcctggggt  cgctgtggag ggaccctgac ctgtgccaat gaagaggacg tcatagtgtc    27180
cgtcagcggc tgcaacccgg tccgcggcaa tttgagtgaa ggtgtaattg ctccaactt     27240
gtaggaaaag agggcgcccc ccagtgggca ggacagagtt gtacatgagg gggtggttcc    27300
gcgcaaactg gatgacatcg tctgggaagt ccttggtgga actgaaggtg ccaaaggtct    27360
tgctggggca ctggggtgg  gggaaaggga ggcacagcag ggatatagat atggggctt     27420
gataggcagc cctccatgcc cagcctctgg gaacatggag ggggatgggg acagaaccct    27480
gccctgagaa ttagagagga gatcagcctt gccctaggaa gtcagaggcg ggaaacaagc    27540
cttgtcttat gatggaaacg ttttcccacc cataactaaa ggaagaaacc acattcacca    27600
agaagacccc aggccaagtt ctcaaaccct tgaggctttg aagtgggttg tagcagaagt    27660
ccctgggcta cgaaccatgc ctggccgcgg gtaggggacg cgaccctggt atgacaccca    27720
ctggtgcatg ggcccctcct tgtgtgcaaa gggtcccaag aaggcccggc gcacgtcgtt    27780
catgctgtac acgcacaccg cagagccctg gaagatgctg ctggaggcga agaccagggc    27840
gaggtgaggg gccgggtgga gcccagcggc ccgccccggg cgctccctac ctcctgcccc    27900
tcacctggac gtggagaaga cggcatagag cagcggggtc cggtggtccc gcgaggacaa    27960
cagaaacaca tcctctgcgg ggaaggggcc tagctgggt  agggcgcaca gccccgctgc    28020
ggcggggct  cccggagtct gcgccgctgc cccctcccc  aaccccatac ccactcccgc    28080
actcacggag ctgatcgaag tgggtgtcgc cctcgacgcc gggcaccgag cacaccagcc    28140
gcgccttcag gaacgtcgtc cacttgttga ccaggctgcg ctggccgccc acgtcgttct    28200
gccgggacga tcaaagggga tgagggcgag accaggcag  gcaaaggggt  aggggcaggg   28260
tcgccgggtg tggcccaggg actcctcacc cggcagatct ggccaacgcg ggacacggac    28320
aggcgtccca gtgccggcgc cgcctctacc gccgtctcac gaaagaagaa gtagattttg    28380
tcgtcgtctg ggttctcgct ctccgggatc caaaatacct tgacaaactt gggctctgac    28440
cgcggcagga ggcatgggtc agcgggtcct ggccttgcct cctgatgcga acccacgcg     28500
ctgcttcccc ttcccgtagt gcgggcacag caccccggat cacagtgtct gaccacccaa    28560
cctctagcac catgtccagt tggcgctctg cgcggaccga atccaaagga tcagggcctg    28620
cgaggcaaga agcagccgcg aggggcagc  agagaccgtg ctacctggg  ggcgcaggc     28680
tgaagcccgg ctagcctccg atctcgcccc acacgtcgcc cagcaccttg ggctgggta     28740
ggagggagat gaggtaatct ggtttcacct tcactcatga atcttcctct ctagcataac    28800
cagatgctcc ccactcctgc ttcaaatcct tctgctgggt cccattgctc tttattatta    28860
ttattattat tattatttgt ttatttattt atttttgag  acagtctcgc tctgtcgccc    28920
aggctggagt gctcgatctc ggctcactgc aacctcagcc tcccaagtag ctgagattac    28980
agtcagagcc taccaccaca cctggctttt tttttttt   ttgagacgaa gtctcgctct    29040
attgcccagg ctggaatgca gtggcacagt ctccattcac tgcaacctcc gcctcctagg    29100
```

```
ttcaagcgat tctcctgcct cagcctcctg agtagctggg attacagatg cacaccatca  29160
tgccggacta atttttgtat atttagtaga gacggggtta caccatgttg gccaggctgg  29220
tctcaaatgc ctgaactcag gtgatccgcc cgcctcagcc tcccaaagtg ctgggattac  29280
aggtgcacac cactgcaccc ggccaatttt tgtattttt agtagagaca gggtttcacc   29340
atgttggcca ggctagtctc aaactcctgg cctcaagcga tttgcctgcc tccgcctccc  29400
aaagtgctga gattacaggt gtgagccact gtgcccacca gccatagcc cttatttaat   29460
ttttatttga tttagagaca gggtctgctc tgtcctgcag tggcagcatc atggctcact  29520
gcagcctcca actcctgggc tcaagtgatc cttccatctc agcctcctga ctagccagga  29580
ctacaggtgt gtgcatgcca ctgccccag ctaattttat tttattttt gtcttgcttt    29640
gtagcccagg ctggtatgaa actcctgtct tcaagcaatc tgtctgcctc agcctcccaa  29700
agtgctggga ttacaggtgc aagccattgt gcccagcccc catgactctt agaataaatg  29760
actctggccc ctgacagtcc aggcccctt ttcattgcta gctctgcaag tctattcctt   29820
tgcttgttct tgcatccagg cctttgcact agttgctccc tctgcctgga atgctccctc  29880
tgcctggaat gctcatccct aaattttgct ggctagctgt cttgtgcttg ggaattagct  29940
catactcccc tcagcacagc ggcttccttt acccaacccc ctccagccac ccagtctcct  30000
tttcccttcc tcccttgtct ctctctggcc tcaaggccat tggacttgat cttatcatgt  30060
atgtgatctg tgaactcaaa gaggtcacgg tcatacctgt cttgtctgtc tctgtgacgc  30120
cagtgcctga ttaaggaggg tatttggtaa gacctggcca cacccactgc tcacttactt  30180
tatgggcctt gcttggcacc tgccctgtgg gagggtgacg acctctaccc accaacccca  30240
ccagcctctc accattgagc cagcgggagt cgtgtggctc tgttcggaga cttggacgtt  30300
gccctaggct gcgaaagatg gtaaagtctc gtcccatgag gtctgctgcc accctgagt   30360
atagctcctc ccctgcagac agagcaaggg ccactcaggc aaatggaggg ctcttggggc  30420
aggagggcct ggggagctct gggagtgagt gaggttatgg gggattccct ggagctcttg  30480
ggggtcttgg gactttgtga ggttctagag tttctaaggg gttctcttgg ggccttagcc  30540
cttggactca cccaccagca cggaggcagc ccgatgcctg gggtcataag gactcttccc  30600
cttgccatcc tctatccttc ctgggtccag ccggaggacg ggctcctggg aggtgtggca  30660
agttgtgact accaggccct tcttaccctc ctgacctccc tccctgccta gatccggcct  30720
tacctctgcc cggtggccca cttccacaaa ggcacaggtt gggtggaagg ctcccgtgcc  30780
acaggccagc aaatgggtgc ggttgtaggc atgcagcaac ttcacgaagt tcatgcactc  30840
agtctagtag ggttggaggt gtgaggcttc ccccagggac gtagccttaa gaggtcccag  30900
ctcaccagtg gcatcctcac ccctccctct cttcggcatc agcccaggca agtactaaca  30960
tgggctacag gacctgggg gcccttgctg accagcccag gcctcacgag ggtgggtgtc   31020
tggggaagca caggcctgca aagcctccca tgactcagag gcaccccaga agaattacac  31080
gagcccccac cctgactcac caccccaga cctcagccac ctcgacctcc ctgccctcat   31140
cccagccaga acaggcaggc ctctgtttta gccctgccct gtctctgggg tgaggggctg  31200
accctcccca ctcccggccc gggcagctgg cactcacacc aatgtccttc cctgcccagt  31260
tgcactcctc tcgccattcc acaggggccg gccaggccag ctatcgggag gttgggggag  31320
aggggacaca ggtcaggaac ttgggatatt ctctacctca gggagccatt cctctgggtc  31380
tctccaggct ggagtggggt cccagggctc cttccctggg gagtgctggg gttgggagtc  31440
cctggcacct tcttggcccg cttgctgatg ttgtccaggt tgagggaggc cacatggttc  31500
```

-continued

```
tcggcaccca caaacaggcg tccacgctcc tcatccacca gcaaggcctg gtagcagcag    31560
gttcgctcca ggctgaaagt ctggagacca tgccaggcct ggagctctgc agggcaggac    31620
actgctgatg actcgccagc catgctggaa gcctccccca ggtcctgcct ggtggtgact    31680
ctatcggcca aggttgccat taggacctgg cctgtacaca tgtgagttta catgtgtgtg    31740
agtttacaca cgcaaaccca agcccaccca ggtgcacgtg tggagctgcc agggtaggtg    31800
gtacatcccc ccaggaagag gaaggcaggt tgaacttggg catgctcaga caggtggtgt    31860
ctccaggcgg gcgcactggg aggcaaggct tatggacacc agagtcctgg gggagactgg    31920
catgcaggga tggccagaac cccaactccc aaaagtcagg ctgagagttc ctttcctgcc    31980
actccaccac cagcctgagc tcagcagaac tgcctattca ctgccactgc caggggcca    32040 ccctcctata caggaggcat gagaagggg ctctgacttc cctgttgctc tgctgaagga    32100
gtatcgcctt gttgggggta ctgaacggaa cagagacaag gtctgttgct gtgggacag    32160 gaggggtctt cctgagaaag cacgaagaga atgtgggcag aggctggggg ctgaggcccg    32220
gacagggtta actggaggtg gcctgagagt gcccactaat cctaccagag tctggtgaca    32280
ggcacgcaca tggggcaaca gccaacacag agccctgg ccatacgggg acccttcct    32340 gcccacctca agctgggccc tcccgcctgc caggtgcacc taccttggaa ggagagccga    32400
aggcgtgggg gctggggcg gcactcccca gccccactgc ccagagcagg gccaggcccg    32460
ggatcacggc ggcagccccg gccgcccca tctcagcagc tcagggtgct cagggttcag    32520
cgggtgtgtg tgtggaggag ccttgagctg ccctggactc tgccccagga tctggaagag    32580
gagtcagcag tgagggcgag ggcgggaggc tagggggga gtccccaggg atcagattac    32640
agcccctagg ggaaagaggc tgggggtcg cattccactt ccgaaccctc ccctccgagg    32700
gtgccccgcc tggccacaat cacagacaca cccacgccac tgggcacacc ctcagggtca    32760
ccctgcactg gcaagcccgc ctcaccacgt caccttccc agtaatctcc tctcttgtat    32820
acacactcac agacattaat tcacaatgtg ccacccactt catgccagcc tagacctggg    32880
aggagggata ctgggagaca tagacaaggt ccccatgtga aagggacag agtgccaaca    32940 aggaatcaga tggatgcaga gggtgccaag tgcaatgagc aaaacaagcc agtcaaaaga    33000
gtgagagtga caggaggggg tcaggcctct ggaggtggca gtgtcccac agtcccgcag    33060 aaaaacacag agacactttt gaggctggag ccaagggtgt gggtgcctgt gaatgtgttt    33120
ccgagtgtcc ccttgtgatg tgcgcatgtg tgtagtgtgt atgtgcatgt gtgtgcacat    33180
ctatgtgcaa atatatagtg tgtcatattg cacatgtgtg gatatgggtt ggtgtgcaca    33240
cacatgtggc actgtgcaat ccatgcagta catatgtgtg atatgtgcat attttgcaca    33300
cagatgtgtt gcacatttgt gcatgtgcaa acgtgtgcac ccataagaat agacatgtct    33360
ctgggcatgc aagtgagcaa atccaactgc agcatcaatc actccattcc tcagagggag    33420
aagtgctacc caggagaccc aagacctggg cagaagcctc agcctctgac ttggggactg    33480
ctcccaaccc agctgaagca gcctctgcat ttgagcttga gggctctctc tccacacccc    33540
tgaggaatca aagaggggca aggtgaggca gcccttcatt tgcacccccag cctcctggcc    33600 tcgctgagct ggccttccct ctcaacgcct ccacagcctc tctgagcctc tcccttcact    33660
tctctcaccc cttgagttct tccccatctt tgagccccct cactctagga gccagacacc    33720 tcccctggc cctcagctgg ggcaaagacc tggctgctat gcccaccctc cttcccaggg    33780
gtcagctggg caggtgctgg acacaggagc ccagggagtg ggacaaggtt ccaggtggga    33840
ttaagcaagt ggagcagctg ctgaggcagg ttccaggccc ctccacccac actcctgccc    33900
```

```
agctcctggc cccatcccag gccaggaccc ccacctccct ccttccctcc gctgacactt    33960
gccgctgcct cttctcaggt tctagaggtc ttccaggcca cactggctg ccttctcaca     34020
ctccaccgag gacttccgca gcagcatctc tccactctgg ccccttccca ccctggggcc    34080
gctgggggacc ctctgacggc tcctttaaga agcagccccc gccccacca ggccagccac    34140
cgccccacgc accgcccgcc gtgccgtaaa gtttagaggg cggatcgggt gaccgggcag    34200
gcagccggga ccagctggag acggcagcca ggcgggagtg gaatgggcac aagggagggg    34260
ctggtaggga cgacccctcc catattgggc cttaaagcag aagggtgccc caggtggcgg    34320
tcccagaagc caggtggcca gccaaggcaa gggaggaaga aacccagct ccaggggctc     34380
agcaggcaaa gggaatcact gagtgggggc accaccgtg gactccaata tctcaacctc     34440
tccctccaca ggtggggagc tgtgggaaa gataatgggg agctcagctg ccacctcagt     34500
tcccagggac cggctggggt ggccgggcag ctggaggtca ggggaggggc tctcaactgg    34560
aggtcggatg ggccctcagg acccagtccc catccttcct caacacttgg gccacttagt    34620
acttcagtgg cctggccagc agtggcttct accatgacag ccagatagg gagggagagg     34680
agggcaggag aggggcagac gcaggaggag cagcaaatct cacttctgca ccacagggcg    34740
gggcccatct ggagtccgcc atcctggaca ggtagctttg catctctgct gagaggttgg    34800
ggggcagacc atgtgacctc ccttcctctg gcttctcttt ctaggttgga ggtgggagga    34860
acaaccccca ccaaacccag agccgaaaac tgagggagtt ttacagacag gacggagctc    34920
ctgcacctcg gagcctcagt tgggaatgac ctggggtctt gtcctgaagc tgagtctggt    34980
gaacgtgccc catttgtaac atgaggggta cttctctgga gggactgtat gttgacagtg    35040
gcagagtgga gccctgaagt ccacctgagt gaatatacca gggcttgaga atgggctttg    35100
atccttccat ccccgcaaaa ggcattttcc taccacctcc caaggctgat ggggcagtgt    35160
gggcatttca gtgttgcag ttctgttgcc cagccctgga tgcctccagc caagcaagga     35220
cagaggtggg gggcacatct ccaagtcccc tggaagtgga agtggggcta tgcccctcct    35280
tcctgagcct gaggacctgg tatacctggc ctggcctggc cagctggcag gtaaataaca    35340
ggggccagtg ggagccgcag ggcccttcag gagggcaagt ggaaggacag atccctgcct    35400
gggctcgtgg gcttcctgga tgtggccttt tcctactcca ggagtagctg cctctagcct    35460
tagaggacct gggcaggctc tcctggctcc atgcaagcag acaacattct ttggctgttt    35520
acagctttcc acccaagcag ccaggatcag caagtgcctc agaggctccc atccactccc    35580
actgtgcccc cataggccct cactgcctta tgttttttcca ggcccagggg ccctgtctct    35640
gtttcatcac cccgcacctt cctccacctg tgttcactct gggaaacggt atcagaaacc    35700
cccccgccac cgccattatc tttccaatag cctgggagtc aaccccagc caaaaggact     35760
agactgtctc tgtccccatt gagtgctgtg ccctgtcctc tgtcctctag atgtgtaccc    35820
tcccttgagt aggaatggag gtctccaggg atggaggtc aagttgtccc tgattccaca     35880
tggtcccctt tctgttcctc agccccaggt ccagtgtgcc aggccatggg taggggcccc    35940
catggaggtc agcactccag gagcaaggtc actgcctgtg ggtcacactg ggggctggaa    36000
ctcctcgagg attctggaat caggcagcct gagcctgagt ctcaacagaa tggggcaaac    36060
caggcaaggc agctggggtc ccttttcctg cctgtactcc tacccctggac ctctctcttt   36120
tgagggagct tccatgggca gagacctgcc tgggtccttg ctctggggct gcctgtcagt    36180
ggcatggcct accacggcct tggcttttcc ttctggaaaa acctggattg ttgtgccaaa    36240
tctcagcacc tgcctcccca cccctggcca ccagctgggc ctgccccttt gccctgcct     36300
```

-continued

```
ggactccggg tggtgtggtt ggggtgggac acccatctga ggaaggttgt ggcaaccctc    36360
ccagtgcagc ctggactgga tgggatcttg ggcgccccac tcacacctgc tttagtcatc    36420
agggcttgtg gctccaacgt cacaactctt ccttgttctg gccacgtagg taccaggtca    36480
tgctgcccag aggacttagg cacagtgggg gcaggcgtgg gcggccatag gatc          36534

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
taaccctaaa aatataccca                                                    20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
tattttagta gtttagggtg                                                    20

<210> SEQ ID NO 6
<211> LENGTH: 295
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
tgaccctgag ggtgtgccca gtgggtgggt gtgtctgtga ttgtggccag gcggggcacc       60
ctcggagggg agggttcgga agtggaatgc gaccccccag cctctttccc ctagggctg      120 taatctgatc cctggggact cccccctgc ctcccgccct cgccctcact gctgactcct      180
cttccagatc ctggggcaga gtccagggca gctcaaggct cctccacaca cacacgctga    240
accctgagca ccctgagctg ctgagatggg gcgggccggg gctgccgccg tgatc         295
```